US009273357B2

(12) United States Patent
Zavras

(10) Patent No.: US 9,273,357 B2
(45) Date of Patent: Mar. 1, 2016

(54) PHARMACOGENETIC TEST ANTI-RESORPTIVE THERAPY-ASSOCIATED OSTEONECROSIS OF THE JAW

(75) Inventor: Anthanasios Zavras, Dover, MA (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 13/439,540

(22) Filed: Apr. 4, 2012

(65) Prior Publication Data

US 2013/0071402 A1 Mar. 21, 2013

Related U.S. Application Data

(60) Provisional application No. 61/471,532, filed on Apr. 4, 2011.

(51) Int. Cl.
| | | |
|---|---|---|
| *C12Q 1/68* | (2006.01) | |
| *C07H 21/02* | (2006.01) | |
| *C07H 21/04* | (2006.01) | |

(52) U.S. Cl.
CPC ........ *C12Q 1/6883* (2013.01); *C12Q 2600/156* (2013.01); *C12Q 2600/172* (2013.01)

(58) Field of Classification Search
None
See application file for complete search history.

(56) References Cited

FOREIGN PATENT DOCUMENTS

| WO | WO 2009/064465 | 5/2009 |
|---|---|---|
| WO | WO 2009/116888 | 9/2009 |
| WO | WO 2010/005939 | 1/2010 |
| WO | WO 2010/033978 | 3/2010 |
| WO | WO 2010/076258 | 7/2010 |
| WO | WO 2010/099255 | 9/2010 |

OTHER PUBLICATIONS

The Free Dictionary, available via url: < thefreedictionary.com/determining>, printed on Mar. 3, 2014.*
Gagneux et al. Molecular Phylogenetics and Evolution. 2001. 18: 2-13.*
Halushka et al. Nature. Jul. 1999. 22: 239-247.*
Mummidi et al Journal of Biological Chemistry 2000 vol. 275 No. 25 pp. 18946-18961.*
NCBI SNP Database. National Center for Biotechnology Information, National Library of Medicine (Bethesda, MD, USA) ss117030021, rs17024608, Jan. 18, 2009.*
Karasik et al. J bone and Mineral Research. Jul. 2010. 25: 1555-1563.*
Affymetrix NetAffx, Genotyping Probeset Details for rs17024608, available via url: <affymetrix.com/analysis/netaffx/mappingfullrecord.affx?pk=Mendel_Sty:SNP_A-1956812>, printed on Jun. 10, 2014, pp. 1-2.*
International Search Report and Written Opinion for PCT/US2012/32150, dated Oct. 19, 2012 (Corresponds to U.S. Appl. No. 13/439,540).
Task Force on Bisphosphonate-Related Osteonecrosis of the Jaws, "American Association of Oral and Maxillofacial Surgeons (AAOMS) position paper on bisphosphonate-related osteonecrosis of the jaw—2009 Update", Can be found electronically at: http://www.aaoms.org/docs/position_papers/bronj_update.pdf (accessed last on Feb. 10, 2011).
Advisory Task force on Bisphosphonate-Related Ostenonecrosis of the Jaws, "American Association of Oral and Maxillofacial Surgeons position paper on bisphosphonat-related osteonecrosis of the jaws",*J. Oral Maxillofacial Surgeons*, 65(3):369-376 (2007).
Aghaloo, et al., "Periodontal disease and bisphosphonates induce osteonecrosis of the jaws in the rat", *J. Bone Miner. Res.*, 26(8):1871-1882 (2011).
Aghaloo, et al., "Osteonecrosis of the jaw in a patient on denosumab", *J. Oral Maxillofac. Surg.*, 68(5):959-963 (2010).
Ahmadi, et al., "A single-nucleotide polymorphism tagging set for human drug metabolism and transport", *Nature Genetics*, 37(1):84-89 (2005).
Andreassen, et al., "The effects of growth hormone on cortical and cancellous bone", *J. Musculoskelet Neuronal Interact.*, 2(1):49-58 (2001).
Botelho, et al., "Gene expression alterations in formalin-fixed, paraffin-embedded Barrett esophagus and esophageal adenocarcinoma tissues", *Cancer Biol. Ther.*, 10(2):172-179 (2010).
Calder, et al., "Apoptosis—a significant cause of bone cell death in osteonecrosis of the femoral head", *J. Bone Joint Surg. Br.*, 86B(8):1209-1213 (2004).
Canalis, et al., "Editorial: Inhibitory actions of glucocorticoids on skeletal growth. Is local insulin-like growth factor I to blame?", *Endocrinology*, 139(7):3041-3042 (1998).
Canalis, et al., "Skeletal growth factors", In: Robert Marcus, David Feldman, Jennifer Kelsey, Osteoporosis Academic Press, San Diego, CA, Chapter 8: 261-279 (1996).
Cartsos, et al., "Implications of bisphosphonate use in dentistry", *Analecta Periodontologica*, 20:181-195 (2009).
Centrella, et al., "Opposing effects by glucocorticoid and bone morphogenetic protein-2 in fetal rat bone cell cultures", *J. Cell. Biochem.*, 67(4):528-540 (1997).
Coate, et al., "Germline genetic variation, cancer outcome, and pharmacogenetics", *J. Clin. Oncol.*, 28(26):4029-4037 (2010).
Fournier, et al., "Bisphosphonates inhibit angiogenesis in vitro and testerone-stimulated vascular regrowth in the ventral prostate in castrated rats", *Cancer Research*, 62(22):6538-44 (2002).
Fritz, et al., "RNA-binding protein RBMS3 is expressed in activated hepatic stellate cells and liver fibrosis and increases expression of transcription factor Prx1", *J. Mol. Biol.*, 371(3):585-95 (2007).
Gordeladze, et al., "Pharmacological interference with transcriptional control of osteoblasts: A possible role for leptin and fatty acids in maintaining bone strength and body lean mass", *Current Pharmaceutical Design*, 7(4):275-290 (2001).
Hopwood, et al., Gene expression profile of the bone microenviroment in human fragility fracture bone, *Bone*, 44:87-101 (2009).
Ingle, et al., "Genome-wide associations and functional genomic studies of musculoskeletal adverse events in women receiving aromatase inhibitors", *Journal of Clinical Oncology*, 28(31):4674-4682 (2010).
http://www.illumina.com/science/icontroldb.ilmn. "Science/Illumina iControlDB", accessed online Nov. 29, 2012.
http://www.illumina.com/science/icontroldb.ilmn. "Illumina Genotyping Control Database Purpose Document", accessed online Nov. 29, 2012.
Kiel, et al., "Genome-wide association with bone mass and geometry in the Framingham heart study", *BMC Medical Genetics*, 8(Suppl. I):S14 (2007).
Low, et al., "Association study of genetic polymorphism in ABCC4 with cyclophosphamide-induced adverse drug reactions in breast cancer patients", *J. Hum. Genet.*, 54(10):564-71 (2009).

(Continued)

*Primary Examiner* — Carla Myers
(74) *Attorney, Agent, or Firm* — Baker Botts, LLP

(57) ABSTRACT

The present invention relates to methods and compositions for testing individuals to determine whether they are at increased risk of developing anti-resorptive therapy-associated osteonecrosis of the jaw.

Figure 2:
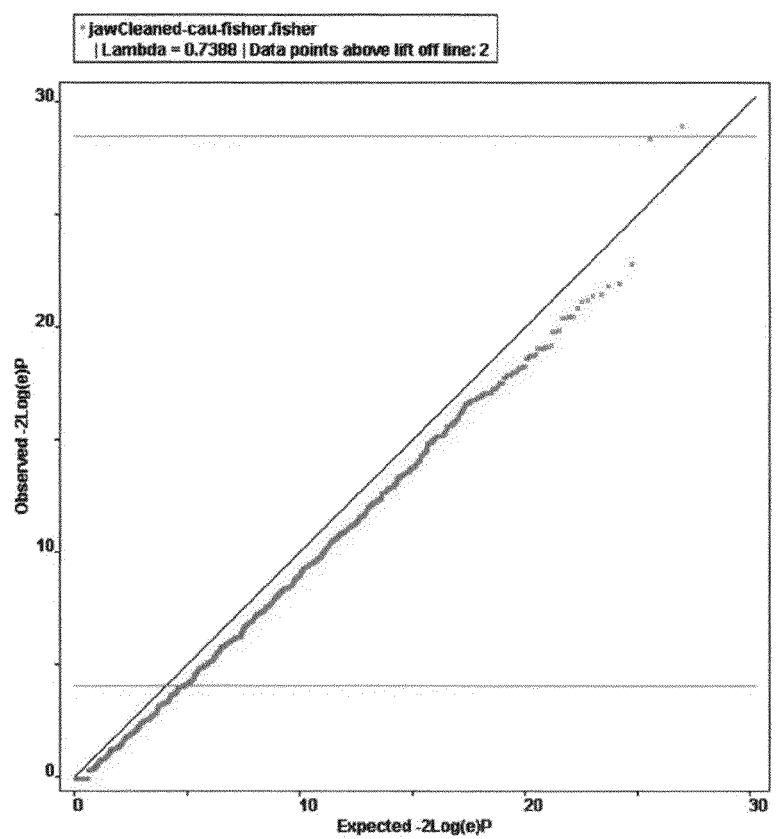

5 Claims, 27 Drawing Sheets
(10 of 27 Drawing Sheet(s) Filed in Color)

(56) References Cited

OTHER PUBLICATIONS

Marchini, et al., "A new multipoint method for genome-wide association studies by imputation of genotypes", *Nature Genetics*, 39(7):906-13 (2007).

Marini, et al., "Pharmacogenetics of biophosphonate-associated osteonecrosis of the jaw", *Front Biosci. (Elite Ed.)*, 3:364-370 (2011).

Nase, et al., "Osteonecrosis of the jaw and oral bisphosphonate treatment", *JADA*, 137(8):1115-1119 (2006).

NCBI reference cluster report rs17024608; found online [Jul. 27, 2012] at http://www.ncbi.nlm.gov/projects/SNP/snp_ref.cg?=17024608; *Homo sapiens* chromosome 3 genomin contig NT_022517.18, GRCh37.p5 Primary Assembly (Jun. 10, 2009) found online [Jul. 27, 2012] at <http://www.ncbi.nlm.nih.gov/nuccore/224515018?sat=14&satkey=2347847>.

NCBI reference cluster report rs9820707, found online [Jul. 27, 2012] at http://www.ncbi.nlm.nih.gov/projects/SNP/snp_ref.cgi?rs=9820707; *Homo sapiens* chromosome 3 genomic contig NT_022517.18, GRCh37.p9 Primary Assembly (Jun. 10, 2009), found online [Jul. 27, 2012] at <http://www.ncbi.nlm.nih.gov/nuccore/224515018?sat=14&satkey=2347847>.

Nelson, et al., "The population reference sample, POPRES: A resource for population, disease, and pharmacological genetics research", *The American Journal of Human Genetics*, 83(3):347-358 (2008).

Nicoletti, et al., "Genomewide pharmacogenetics of bisphosphonate-induced osteonecrosis of the jaw: The role of RBMS3", *Oncologist.*, 17(2):279-287 (2012).

Novembre, et al., "Genes mirror geography within Europe", *Nature*, 456(7218):98-101 (2008).

Owuor, et al., "Antioxidants and oxidants regulated signal transduction pathways", *Biochem Pharmacol.*, 64(5-6):765-70 (2002).

Palaska, et al., "Bisphosphonates and time to osteonecrosis development", *The Oncologist*, 14(11):1154-1166 (2009).

Pollak, et al., "Insulin-like growth factors and neoplasia", *Nature Reviews Cancer*, 4(7):505-518 (2004).

Prescribing information for Mecasermin (Increlex) (downloaded on Feb. 11, 2013).

Priority NDA and BLA Approvals in 2005; Information Sheet Mecasermin [rDNA origin] (marketed as Increlex) retrieved online Nov. 29, 2012 at http://www.fda.gov/Drugs/DevelopmentApprovalProcess/HowDrugsareDevelopedandAproved/DrugandBiologicApprovalReports/PriorityNDAandBLAApprovals/ucm051208.htm.

Price, et al., "Principal components analysis corrects for stratification in genome-wide association studies", *Nature Genetics*, 38(8):904-909 (2006).

Purcell, et al., "PLINK: A tool set for whole-genome association and population-based linkage analyses", *The American Journal of Human Genetics*, 81(3):559-575 (2007).

Schwab, et al., "Role of genetic and nongenetic factors for fluorouracil treatment-related severe toxicity: a prospective clinical trial by the German 5-FU Toxicity Study Group", *J. Clin. Oncol.*, 26(13):2131-2138 (2008).

Shane, "Evolving data about subtrochanteric fractures and bisphosphonates", *N. Engl. J. Med.*, 362:1825-1827 (2010).

Shen, et al., "Genome-wide association study of serious blistering skin rash caused by Drugs", *The Pharmacogenomics Journal*, 12:96-104 (2012).

Tagami, et al., "MRP4 knockdown enhances migration, suppresses apoptosis, and produces aggregated morphology in human retinal vascular endothelial cells", *Biochem Biophys. Res. Commun.*, 400(4):593-598 (2010).

Rodan, et al., "Bisphosphonates: Mechanisms of action", *Journal of Clinical Investigation*, 97(12):2692-96 (1996).

Wang, et al., "PennCNV: An integrated hidden Markov model designed for high-resolution copy number variation detection in whole-genome SNP genotyping data", *Genome Research*, 17(11):1665-1674 (2007).

Weinstein, et al., "Inhibition of osteoblastogenesis and promotion of apoptosis of osteoblasts and osteocytes by glucocorticoids. Potential mechanisms of their deleterious effects on bone", *The Journal of Clinical Investigation*, 102(2):274-282 (1998).

Wessel, et al., "Zoledronate, smoking, and obesity are strong risk factors for osteonecrosis of the jaw: A case-control study", *J. Oral Maxillofac. Surg.*, 66(4):625-631 (2008).

Yamashita, et al., "Effect of zoledronate on oral wound healing in rats", *Clinical Cancer Research*, 17(6):1405-1414 (2010).

Yoon, et al., "Association between GIy1619ARG polymorphism of IGF2R domain 11 (rs629849) and advanced stage of oral care", *Med. Oncol.*, 29(2):682-685 (2012).

The Wellcome Trust Case Control Consortium, "Genome-wide association study of 14,000 cases of seven common diseases and 3,000 shared controls", *Nature*, 447(7145):661-678 (2007).

Zhang, et al., "Replication study of candidate genes/loc associated with osteoporosis based on genome-wide screening", *Osteoporos Int.*, 21(5):785-795 (2011).

Office of the Surgeon General, "Bone Health and Osteoporosis: A report of the Surgeon General, Chapter 5: The Burden of Bone Disease", *Office of the Surgeon General*, Chapter 5: 88-107 (2004) (downloaded on Feb. 11, 2013).

Zavras, et al., "Insulin-like growth factor II receptor gene-167 genotype increases the risk of oral squamos cell carcinoma in humans", *Cancer Research*, 63(2):296-297 (2003).

Zavras, "Pharmacogenetics to screen for drug-induced osteonecrosis of the jaw", *Pharmacogenomics*, 13(9):985-987 (2012).

Zavras, et al., "The role of IGF2R in carcinogenesis", *Nature Reviews Cancer 5*, (2 pages) (2004) (Retrieved Apr. 25, 2013).

Zavras, et al., Table 1: DNA-dependent RNA polymerase I, II and III in cancer, From the following article: The role of IGF2R in carcinogenesis from *Nature Review Cancer 5*, (2 pages) (2004) (Retrieved Apr. 25, 2013).

Zavras, "The impact of bisphosphonates on oral health: Lessons from the past opportunities for the future", *Ann. NY Acad. Sci.*, 1218:55-61 (2011).

Zavras, et al., "Bisphosphonates are associated with increased risk for jaw surgery in medical claims data: Is it osteonecrosis?", *J. Oral Maxillofac. Surg.*, 64(6):917-923 (2006).

Sarasquete et al., "Bisphosphonate-related osteonecrosis of the jaw is associated with polymorphisms of the cytochrome P450 CYP2C8 in multiple myeloma: a genome-wide single nucleotide polymorphism analysis", *Blood*, 112(7):2709-2712 (2008).

Katz et al., "Genetic polymorphisms and other risk factors associated with bisphosphonate induced osteonecrosis of the jaw", International Association of Oral and maxillofacial Surgeons, 40(6):605-611 (2011).

\* cited by examiner

Figure 1A-B
A.
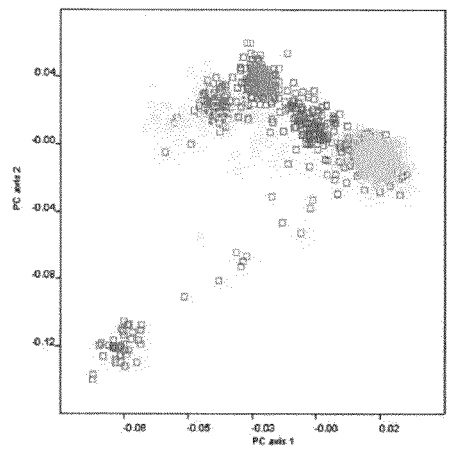
B.
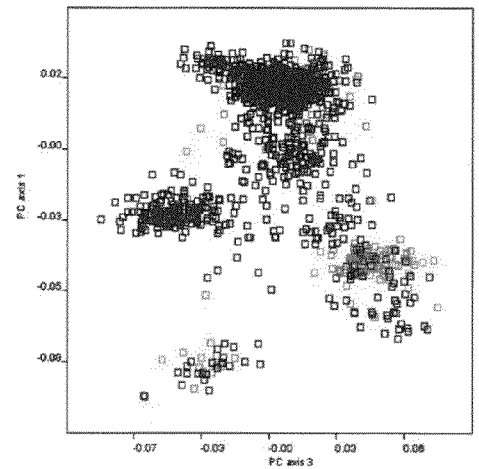

Figure 5A-B
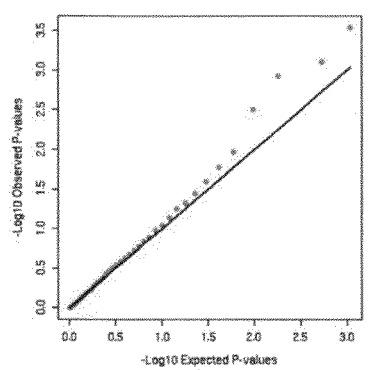 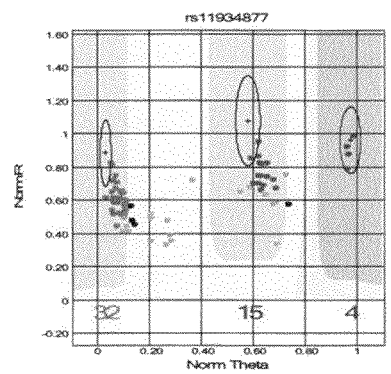

Figure 6A-B
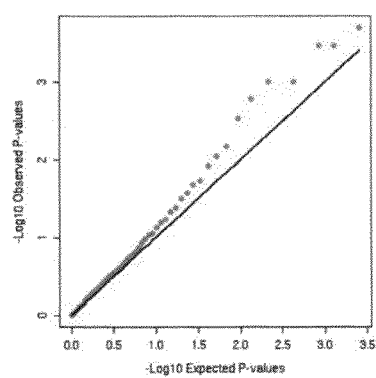 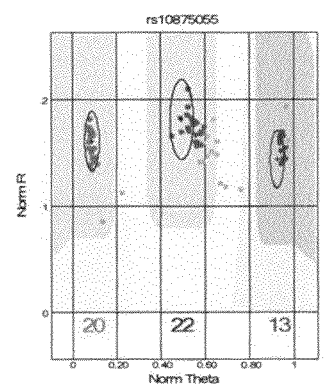

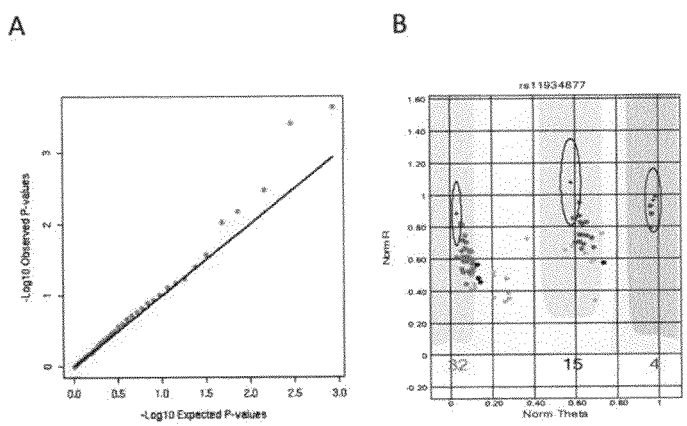
Figure 7A-B

Figure 8A-B
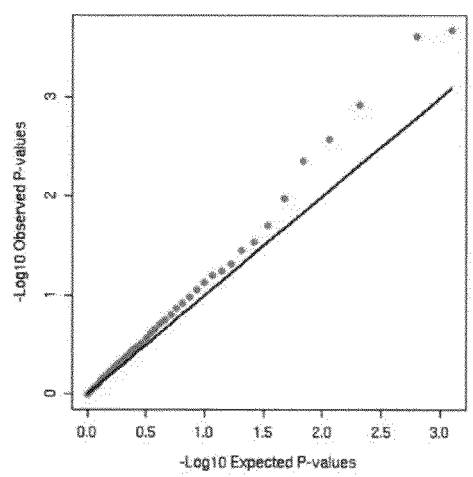 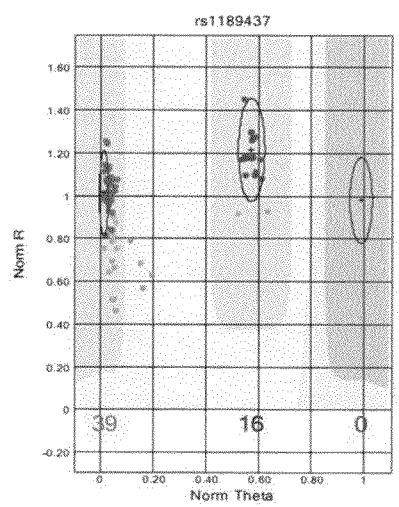

Figure 10A-B
A
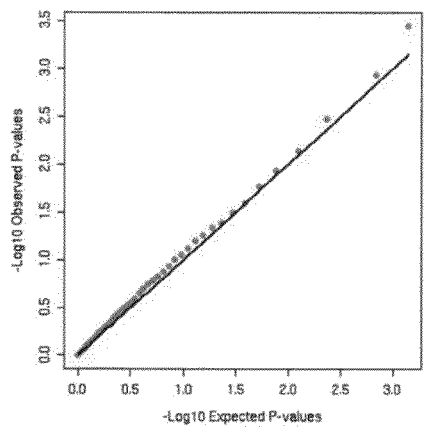
B
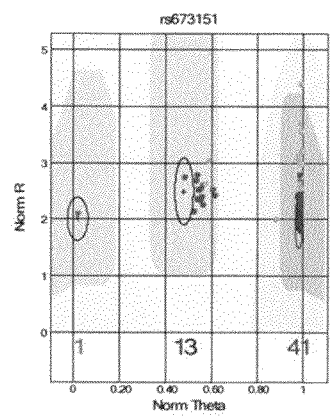

FIGURE 11A

```
618421 ccgccatacg ttatgcaacc aacagtaagt gttctcagtc acctgaggct aatatttcta
618481 ttatccaagt acaagctttt ggaatgcata gaagctttgg ggtaaagctt ttgtatat
618541 atgtaactcg ttcaggcagc catattctcc agataaaaag ctgttcctga aattctacaa
618601 aagcatgtac aatagatagc tagagacata catagacata gaatcagata aagagagg
618661 gtgaaaaagc aagagagtga gagagagaga gagagtgcct ggaaacttta ttagaagaaa
618721 tagcaatcaa ccattcaagc tgagtctacc atttcttatg catgaggaat ttctgcttta
618781 tgcaggaact cagaactccg gacaattaaa tttattctac aaggaaactc tttgttccc
618841 ttctcttct gatatgcttt tctttctttg gccacagtct gatatgcctt aggacaatt
618901 tggagtatca tagacaagtt ttgacttgaa gcaatatatt tcaaatatga aggtagttgt
618961 ctgctaatag atgaatttat atagatagat ggcaaggtgt gtaaatattt tcatgtaat
619021 taactatagc agttttcttt ttctatagtg gaaattttct ctctgcaaaa tattcaaatt
619081 ctcttttta cttgctagat ttcccattt atgcacaat attacatcaa ttccaagtga
619141 aaagtatgac gtattacatt agaatctaga ctgaaggcta atgattgcat ttatcttgc
619201 ctaagtcttc cagggttttct agctctatag aagtgcgaga tagagatttc aatagcaaca
619261 cactcatgag ggtgtgaggc agggaaaga gccctagact ggaagttgtg tgacaaggtc
619321 tctggtgact cttctgggta tgctctctgt gcatttgttt cctttctga cactatatac
619381 ttaatagtgc tttgtgagg atcaaatgag agatcacatg tcctcattat tattgaatgt gttcattata
619441 tatacatgct atgcattatt attataaccc ctttagaaga taaatgtaag taagttagta
619501 caaggaagaa gcagtgctaa atttttaaccc gacatccatt tcctgaactc agaaaattag
619561 tacattaaac accagggagc taaatacgca tatttcaccgt gacatccatt tttaaataa ggaacttttc
619621 agaatctggc tttcatatct gagcagggtc catttttattt attaaagaa taaaatatat gtagttacc
619681 atgttgctcc aaacattttg atagtttttt tcccttttatt tctataaatc tactattatt tacacactt
619741 acagcagaac tttgtaccat atttttgcaaa tcctttatt tctataaatc ataccactat gcaacaaatc
619801 gagggcttt tgagtcatc tagtctatgt tctataaatc gtttgtgctg ccaaagcaat
619861 caggctacac tttttctgtcc aagtcataag gtaaaaggaa agaagtcctg ccaagtctc
619921 acatagcata gcaaagactg agccaacgga ggaaaaggaa agaagtcctg ccaagtctc
619981 aaaaggagac ttttctggaag gaaacaacca ccttctaaaa aatgtgttca tccgtaaagc
620041 actaatacta acttagtcct catactgagt tttaacacca tctctttgtg gccaaaagga
620101 gtgcacatct ggcaaaatct gaatatttta ccagatgtca aactatgtaa gattcttcag
620161 tacttccaga tctattaggg gcagggaaga tggttgtatg ggactttatt tcagctgtca
620221 ctcaggactt ttacaagct tttcacacac ctcctttcc acccagtac agcttcagcc
620281 tcgtgttcgc atgtattatt tctgtgtgtg tattattagt gtgtgtgtac atgtgtgt
620341 gtactttaat ttgtcctttt agatttttcct tgctgtggct actactcaga gctgatatcg
620401 tatcacctcc catgactaaa ttatgcatcg tgcttgagct taggccacta ggtttaaatg
620461 taatgttat ggctgggtg gattcctgga aaaatagaag tggctgggcc acaccact
```

FIGURE 11B

```
620521 ttgctatctt ttagatggag aaaagggcaa aacagtatca tggaaacaca gagtttgtac
620581 catcaatcat ttccctgtaa taatcctgtt ggctgtccat attacataag taactttacc
620641 caactggctt taattttatc atcaaagtga ggttaagtca ccctatgata ctaaaatata
620701 aaaatattca agccatctta gacaacaaat caaaaaaact gaatctgaga agaattaatg
620761 aggaacttga tgattaacaa catggagct tggttgagct cattaggaca ggaaacccat
620821 tttagcaagg gggtattgag ctatttacat aaacttttctg agccacagtt tctcatctgt
620881 aacatggaca taataatacc caaataatta tgttttgttc attaaatgaa ataaggcatt
620941 aaagctctta aaataatttc tggaaaagag cactcaataa attattatta tttaattata
621001 ttagtagact tctcattatg ctttaaatta tcccagtttt atcaaatgag tgttgttata
621061 agcagaaagt tgaaagtaag caactttgtt gagaatcatc tattctacc acattcatag
621121 tgctaattac cttactttgc taatgagttt ggtggagaaa ctctgtgct ataaacaaga
621181 caaattgctt acattggtac ttattccat tacttttcta acattcaaca cctaaaactt
621241 aaaaaaaaat gccattgag aatctccttt tttcagtaac tggagactac cttacaaata
621301 aattcaaggt gtcaaaatct atgtctcaaa tatattgccc attaattccaa tttgcttgca
621361 acttttcttc tctgtcacat ttctctttc ctcacttat gataatttca tgcatgaggt
621421 ttcattgtac aggaatatac ctcccctatc accaagcgtg tacactgatt cctgagttgg
621481 agccagatgt attgcctagg ctagaagccc ttcgggttct ctctcaggct tgacttaaag
621541 ggctctaatg tctcaatctg gtttgtatct gaaaacagtg cttccgtaaa gttctaaagt
621601 agagccaat gacctgatc tctttgctaa ggaggatgaa tgggtaaact ggagggcaa
621661 caactggtaa gagagaaatg aaatgcaca gagaactaaa gggaacagta aagcatgaa
621721 agaagatag aaaacataag catataattt ctaaagtttg ccatttaagt tgtttctt
621781 gtacatttaa ttttctaagt aatgtgcttg tagatttaga aaaaaaatac tctgggaaga
621841 aaggatagat gtctctttgc atggattata attctgatgt tttgaaaga aagagattt
621901 ctgttactgg acctgggaa cttattggat ctcctggaaa gctgtcaaac cccacgtaga
621961 gaatcagag catttcgtt tgcctttgt tattgtcac ctgaatagac tctgagaaga
622021 cagcactgtt agactaaatt aggaattccc ttttttctga gaagtaaaaa tgctgactt
622081 gtcaatgtag ttggttattt gcttctgctt ctcagcacag acgtctatac tgcatgctga
622141 aatctcacca tgcactaaac agaatttaa tagttgatgg attgcaccaa atacctactc
622201 tacagagcag tatgttacat tgcaatgtca tatgaatca cagttgaaat tgctgtgttc
622261 caatacattg gatattttgt tacatctgtt attactgaca aggagaaaag atgataattt
622321 tcaaggaa gcagagttcc actttcttaa acttatttta agctcatttg aagcataaat
622381 cttctgttct tgatatgggt agtgttatat catccaagg agaaggtca gctttcattt
622441 ttgacttaatt acaaattggt tatctaatta cagtattcta agaaatgcaa gatgccctta
622501 ttgaatcaat acatgatttg ttgccatggc aacaaatggc aaaaagtttg caagcaaata
622561 aaaaattata atcgttatga ttaatgaacc ctgagttttc agctaaagag aaaatataaa
622621 ctctctcttt acaaccaggc tgtttaagaa gccccagaat acttaatttg gtcattcttt
```

FIGURE 11C

```
622681 gcccttaaac atgtaaggcc taaggcctag ttttagagtt gtgtccttca attttgtagg
622741 tgtgtgtttt gagaaggcat tatcaccaaa tttgccctaa ttactgtaga aaatagtcct
622801 ggctttgcta ccgttaaata taacttcaaa atttttaccgg aattttcaa atataatctc
622861 agcaactttta gtaaaataac tttaaacaat gaaatgcaag gcttataatt caaaagaagt
622921 gtatagagta taaaagattt tccacctagg atcccttcat tcatcattte tattctccgg
622981 aaatacacat tgtaaacaaa atcagatatt tctatccagt caattttata tgcatatgaa
623041 attatatatt tgcatgtgtg taaatgtgta tttaatat agaaacaata ttactctaca
623101 aatgttgtat tatgattgc tttattttc ctcaataata aatgttctg gatgcaata
623161 aatatgagcc atatatagat ctatatcaat tttgctaaca gctccattgt cactactgta
623221 taaatgcacc aaaggtgta ctttcttgaa aactcaagac agtaatatta caccctagtg
623281 agaaaacgtc tgtcagataa gttgctgaca caaagatat ttacatttta aaatttgata
623341 tacattattt tcaaattgcc tttagatag cagttttct tctccataa cctcaattaa
623401 aagcaggtaa tctcaagttt taaatatttt gttaatgtgg taaatgtctc actcatattt
623461 tatttcatt tctgaatcct atgagttgag ttgatttca cgttttca gactaattt
623521 gtttctta tctctgaact tcaagttggt ttgcttgct tagtttct ttgaggtact
623581 gatcttttct tatttataaa agatcttatt acagttagta agtttatgt gtcatagata
623641 atttaaatat tatctcagtt gacttttaaat tttaattgta tatttgtcat gcagattttt
623701 ggtatttatg tatcagtctt tctttagaa caggggtcag caaacttttt
623761 ccgtaaaaag ccaaacagta aatattttct gtttgtgag ctatatggtc tgtgtcacac
623821 ctactcaatt ctatgttta ttgtgaaagc atccatagac aatacataat gaatggctgt
623881 gccttgagtt ccaataaaac tatatttaca gaaataggta tggccacatt tgactcacag
623941 cctatatttt gacaacccca gcttagagc atctgtattc catgcaaaaat accttaatca
624001 ctatagattt aaaatgccat atgttttctt actatgctta tagtaaattt tgttaaaaaa
624061 tgttgttacc tttgaagttt attttatagc atgagatgag attaagatto aaaatttcat
624121 ttttttgatt tttttcccc caaacatgga accaattgcc ataacaaatt ttaccaaaga
624181 aaccctctat atttctgtcc ctggcataaa tttatgcca atattatca cataataaaa
624241 tcttttatc tttgtatctg tttccaaat gctcttctgt cctgcttctc tattttcctt
624301 gagcattgct ctatttttgac tactataact gacaataact taatcagagg tgtccaatat
624361 tttggcttcc ctgggccaca ttggaagaaa aattgtctta ggccacacat aacatacact
624421 aaaactaatg atagctgatg agctaacatt aataaataag tcttataata ttttagaaa
624481 gatcgtgaat ttgtgtggg tcacattcaa agccggttgtg ggctgcatgc agccagtggg
624541 ccacatgttg gggaaacttg ccttataaaac tgataggaaa tgtccacaat atttttttca
624601 ttgtttctca aaaattttc tagctatttt acatttcag atgaacttta atgcattta
624661 tgaagttaaa aatgtactaa aattttcta tatatattga cttatggaa atttaagaat
624721 atgacatatt tacaacattg aattttctta tacaagaaa agaactttc gtctacccaa
624781 gaattcttt atgtattttg gatcacttaa tagagtatca ggtttccgcc atatgtatc
```

FIGURE 11D

```
624841 tatacattgc ttaatgtttt cctggcatct tagtattttt gttattatat gttttagttt
624901 tttgctgtgg ctataacaaa gtagcacaga ctgtgtaatt tataaagaaa ataagtctat
624961 atagctcaca attctggagg atggaaagtc caagagcttg atacaggcag ctggtgaggg
625021 ccatctgtt atgtcataac atggcagaag acatcacctg gcaagaaggc aaaaacaaga
625081 gagccagaga gagcttcctt ttctaacaaa gctattccca caaatctaat tccatggcaa
625141 cattaatcca ttcatgagga cacagctgac attaatccat tcatgaggac acaacactta
625201 tttctaatgt gtaagttttg taacacatga aataaatatt cttcggcatt gcaattataa
625261 aaattttatt atatttctc attgatcact ttggtgtata aaaatgtata tactaattt
625321 attcattaa tttaaaaat ctattaattg ttcaaaagta ttgctgaaat ttagaatata
625381 tacataagtt aaaatatgca tataaaatac ccattcctc ttacccaaag attagtacag
625441 ttaatatcta atgttacatg tttccagatg tttttctgta tttatatcaa tatctaccaa
625501 cttatctaca tctacaaaca tgaatgcata caatatacc attatatata tcatatgtat
625561 gtgtatatac cattaccaa aatgatatca gtcaaatgac atcacacaat atgtgctatt
625621 ttcagtgaat atttccatt tttccagtt gagaaatttt ttatcatctc tcatcaaatt
625681 tcccaattg agcaaaaatg ttattacac tggtttaccc aatccaggaa gcaatcagtg
625741 accacatatt atatttggtt attgggtcat ttaagctct tttaatctgg cagtctttt
625801 tcccttcctg ttcatggtta gctgtcctgc catgtatccc actcttgcaa aatgtttggt
625861 tgattcttca tgatgctgtt tagccttttc ttctattca tatatgaaac aatttttgta
625921 accagctatc tttctgaatt ccctcattgt cccctcattgt tttcaatcga atatttaatt cattctcagc
625981 tttccaggt catcaaaaat aatataattt tccacctgat tttaaatctt tatatttcat
626041 aattcatttt ctggccaaat ggcttgaa tgtatccttt gacttattc ttatcataat
626101 ggatatgcca ctatgaatta tttttaatt tagtgtaga tgttgaactt aatcaaagtt
626161 ttttgaaac tattgatatt attttccttt tgccaattt atgtattaa tatatttgta
626221 attaattgta tcataattt taatatttc ctaaggtaga ctaagttaga catcaactcc
626281 atttgttat gatatatccc tgttaaaaat atacttccgg attatactt tgaatagttt
626341 attatcttgg catcagtttt catcaaattt tattaataaa attagtaagc tattttgtc aggttgaat
626401 attcaattaa caaaggcttt ataaagttaa tttgaataa ttcctttt tctaattgca
626461 gaaacaattt taaatagcat taaaaaaat tctttttgga gattataaaa tcttcataccc
626521 caagactatc ttagttttgg ggaagagatg catttatttt accaaatcca gtttaaaaaa
626581 taatctatta ctccagtcag acatgttctc agaggctaa aactttataa tctatttaag
626641 aatttgttaa ggttgcccg gtgtgttgac tcaagcctgt aaccccagca cttggagagg
626701 ccaaggcagg cagattgctt gaactcggga gtttgagacc agcctgggc aacatgcaa
626761 aaccttgtcc ctacaaaaaa tacaaaaaaa ttagccaggc atggtggtgc atgcctatag
626821 tcccagctac ttgggaggct gaggtgggag gatgttttga ggataaagc tcaaggctac
626881 agtaagccaa gatcacacca ctgtactcca gcctagcaa caaaacaaga cctgtctca
626941 aaaaaaaaa caaacaaca gaatttgtta ataccatgta tgatcatgat catgaagaac
```

FIGURE 11E

```
627001 tctgactgtt gcatagttga tagtcatgtt gctgaatgat caaatcaatt ggattgtgaa
627061 atgccacggt cttaacaaaa ttagcattat cttttgctcc atgactagtt gttgataatt
627121 agatcatagg ccatatagtt cttaagttaa atgtagtaca aagtaaaaat aatcagttgc
627181 caactgccta ataaggaatt tttaggtatg agcaagttgt aaatcaataa tttgtaattt
627241 ttaagaatgt atagagtttt taatgcccct gattgtcata aaacttgagg aatattttcc
627301 tcacatgctc gcttgattca gtcttcttt cccttagccc ttagctatac caatcattga
627361 ctcctcgtct tataacattg agaaacttgg gttcaatgaa aaaaatcaac aaataataaa
627421 aacaaatatt cttgagcatc aaatatgtgc atgatatttt tctagatatt attggaaatg
627481 gaggagagaa aataagaaat aatttgtcct caagacttga aatataattg tagaaaaaca
627541 ttatatgctc aggataattt aaagaagcct gtacagttga aaatttgtca aaattttagt
627601 aattatataa cctaaaaaat aattgaaaag ctgtgaacag ttaaggacag agaagaacaa
627661 tgacataaag atgaccttaa aggatgggtg atgtttgtgg gctaaaatg aaaaaagaga
627721 acatttttaag tgaaaataat acacaaaaag tatgggagga gagtctcaag ttatttcaaa
627781 ggggactacg ggggagcaa atagcctgcc ttaagtgaaa tgttatatt agagaacgag
627841 ggaaatattt ggttggaaag ttaaattgct acgtattgaa gtacaactt cacgcagtca
627901 aatctggcag acttcctac aacatttttta ttagcttgac aatcccagta ctattgttca
627961 gaatttaagt ttactttgaa aaatgtaaaa cagaaagagt aagttatgtc actgatgtgt
628021 gcgtaaaagt aatatatgc agtggagtaa tgtagaatc aattataaat agaaaaaaat
628081 aaattctgct acattatgaa atgccattgt gcaagtctt tgtatataaa gtcatttat
628141 attcctaaat aatttggag gtaatgttta tcttccaagt agagttcctg aaggcttcct
628201 gctgtctgag atccctgcct cctaagcaca ggagtgtcta gggcagtgg tgagtctaga
628261 atcttttgaa atacaaaaaa tatgctttaa tacattttt aaattctcag ataatggtgg
628321 ttggaagctg ccaagtgcta ggcaccaaca catctccaga gtacataggg atgcatctat
628381 taatagatgg ccactgtttc tatacccagt aacgtaaaaa ttgtcccaac tgaagtattc
628441 tagctctgtt actgtgggag tatgcggggc atgtgtgtgg tatgtgtgca tgtggcctac
628501 cttctgcat gtggttttct gttattttac taaacacctt taaaatgaaa gactagctca
628561 agacataatg tatcacttt tagaacagca ggcacagcat tctggacatg acacaattga
628621 cagctgctaa gaagaaaaat ttcaatcata catgatctcc agtgtgtcct tggatagtat
628681 ttagaattc ttcattactt catcattagt aaagcagagt atcacagctt tgccagttcc
628741 ttcataaaga tgtagatgat gttacttcct taatagctat ttaacatatt aaatataatt
628801 caaatagaaa taatgttaaa tatccaatct attaaattct tatttcctaa agaaagaaaa
628861 tatgcagcta aaataaagtc ctgtcagac tttctagaaa acagcaagtt accagggcga
628921 caatcatata gaggtgggt agatcattta cttataaat gttaccaggg taacagaaac
628981 tactcgtgga aatcactgga ggatttagga tgagagtaca gataaccat ggaactttt
629041 gtctttcat agcacattgg aacaaaatgt ccaaacatat ttaaaacttt taacacttat
629101 gtgaagtatt tgggtattca ttaaatagat gatcagaaac gggttcacat attgagagta
```

FIGURE 11F

```
629161 ttctcaaatg tgaagagtac atctcaaatg taaatcaaaa gatattattt ttgatttctt
629221 actgctcagt atgtcattgg gatactttat tttactctga atttgactt tgctagatta
629281 gttctagaga acctagttat ttccacctag gtgctatgtc tgcaatttag gatcatggtt
629341 aatggtgttg attagcatga ggcttgagtt ttataggtca accaattagg gtgtaggagg
629401 gagggaagtg gttaatggag agaaaggaaa aaactataca tatacatata tatgtatacg
629461 tatatgtata taatttcat gtgtgtgtt gtgtatggcg tgtacggatt aatcaggttt
629521 gcttaaagaa ttatggagtt tagagttaga tttttcaaaa tgataacaca aatacaagta
629581 aaatgccttt aaacttttct actgcctaag agaagctta ccaaagatag gaattaaacg
629641 tacattttc tcccdgtttt agaacttgtt gtttccctcc caataagact ctgtcagaaa
629701 acaaataatt ctaatatgtt catctatggt taacagttaa ggtatgtgca aagtctataa
629761 gcagtaaaga ggaggaagtt actcactgtg gagggagtag gaaataaga acaaggcttc
629821 acagagagg taactcctga acttggtttt gaaaactaaa aggagttttt tagaccaaca
629881 agtgttgggt gtcaggcagg aagggtgctc tgagcaaagt gatcagtaga ttgtaggcag
629941 ggtttttggtc ctattcacca tgtgctgcag ctggtgaaca tctaagagaa agcaaggtat
630001 ttttacaggc taccagggtgc ctctaacact ggggcatatg catgacattt gtgtgccctt
630061 caacagttct gccacagaag gtatcactta atcatgatta ggctgttgt cctatattcc
630121 attaaacatg gcatcttctc ctagagttcc gtttgcattt ctaggcaaag cctcctcacc
630181 aatatccgat gtgcccttc acaagttctc cactcagagt tgagtgtaat atgcagagaa
630241 tgttattgat attacttggg tatcataaag taatcattat agcctctgca caaggctaat
630301 tagtcctaat tatctgaata cccaggtga aagtgagatt tctactcccc tcagaacccc
630361 aagaatgcgt agtgtctcat cattgactg tcaacaaatg cttcgttgct aagttattca
630421 aacaataaag taagatgata gagattctaa gaaaaaatac cagaacttat atgtctacat
630481 gagttttcttt tttctatgtg atgaaattac atttattctt tttgggagggc cttttccatt gatgccatct
630541 tagactagga cattttaaaa catcaggtta ttcacactg ataaataga tatgaaatg ggtggataga
630601 tcataccaagt aaaacaagtt catcaggtta ttcacactg ataaataga tatgaaatg ggtggataga
630661 atacataata gctagataga tagtagaga ggaagatgg atgcagggat gcgatggat gaatggatgg
630721 tgatgaatga atggatggag agacagacag aataggta atagatacc tgggacatga cactagttct
630781 atgggtggtc agacagacag aataggta atagatacc tgggacatga cactagttct
630841 tcttttccaa ctacagtata atttatttat ttgagagttt attccatata gttcgcaata
630901 tttctcccgt tctattttgt tctaaataaa tatttgataa taagttacac tttatagact
630961 atttctgcat tgcaaatat taagacacaa gcttccaggt gccgttagac aaggatactg
631021 acaaggttt ctgagaaaat taaagacgtg catctctct gaaatcaaaac ccaacttatt
631081 agggaaatg atgctaatat taaattttgtc tttgtaagtt tgataccattaa atatgtcat
631141 tgtcagtaag gaggtgtgtt aaaacaatt taggaaaatt tcctctatgt tcataatgta
631201 gtattctaat tccttttcag ttgcagattt gtttatatca gctgaaacaa ctgtgttatt
631261 cagcgtagtg tcttaattgg cagttacatc tgtagagaga acattcct tgtggacatt
```

FIGURE 11G

```
631321  tctttttatta actctcaata aaagccaagc acatgttaac tttcaatttt ctgaagaaat
631381  gtataggagca actacattaa tattcttcag gtatgtaagt ttcttataac ctatcttgat
631441  ataagaatga ctcgtaaat ccaattggct gacatgtggc ttattggtg tttattttagt
631501  ctgagccagg atgttattaa atttataccca tctgatttat agtttcacct aggtacaggc
631561  tattttacct ctcatgaaa agatgcaag attgttcagt ttgtgccaga attttcctta
631621  ataaatgtct tcaaagctct cacaggagcc caagcatgta caagttggg atctagtagt
631681  tctgtgctgt tgagtgcttg agaggcaaat ttcatctaaa atattgaggg caggactaag
631741  acctcttggc tatcatcact aggtggctca taaagtactc atgatttaa cagtactaga
631801  ctctgatgca cttgccaaga tgaatcaggt gtaaaatgta ctccgtggca gcaaacggaa
631861  ctgatagaat agaactattt gatgtggAcc atgaatttt aaagtatct gcataaattg
631921  atgatttggc atcagataaa gctgatatca aaccattcta tcttacaata attactcaat
631981  atgttcagca gactcttgaa tctgcacttg agaaatgaca gaaaaactat atcatcagca
632041  gagaaaacat cttcctgctg acctaggaag gcatacaaat agttcagttg gcgtcacact
632101  gtttatgcat aatattttac aaattagggt ggtacttgtt ccctttata tcacttaaca
632161  taagtataat ttcattgcac ataactgagg agaaatagta gaaacaagct gagaaaactg
632221  aaagcaaatt ccaagaaaga ggattagtcc tcatctatgt taaaaagaac attgtgctct
632281  tggctttatt ttcttattta gcatagagaa aatcaagcta attatcaact tgggttctga
632341  ataatccct taaaacttct attgagaaga gaaaccttt atcaaagagt tattcttaaa
632401  cggttcttaa tcaatacaca ttagaaccat ttctgcataa caatgttgta tattaaaaat
632461  caattcttac tttcgataa aggcttttat cttgtcttgt atctctaagt atttcaatc
632521  aatactgaaa aaatcattat gcttccaagt ttgttaca tgatacatgt ctaaatactc
632581  agattctgat atcacactcc aaaataatct aacttctga gatgcataa tgaaattat
632641  ttcaaggaag tgttatatt atacatggca tgctgaaagc tgaactgatg aatgattgat ggatactaca
632701  tacacattac tgtccatata tatacatata atacaaatgt tgttttatat tatagatatt attaaccaa
632761  aagactgaca tataacattag aacactgttg agatttgtg tattaattag gagttatc agagttacat
632821  ttaaagactg aacactgttg caaaactgac tcaggaaatt tcagcctagg taggaagag aatatgtgg
632881  atgcatgggt gaattaggat gtgtaagaga agcataagt tgaggatcag ggatatatag
632941  tccttaaact gaattaggat gtgtaagaga agcataagt tgaggatcag ggatatatag
633001  ttcctttgg gcatgttgac tttcaaggc cagataaaga tttcaatat gtacctccaa
633061  atacaggttt gccacccaag aaggtagta ataaacttat gagtcattta ttcctgctgg
633121  agagaataga tgagattct agcaattcgc tcacttttca tagtaattac catgcttgat
633181  ctatcaata gctagtgttg tgcatacgct gaggttacct taaattact agtcttatat
633241  gtactaactt aatgcttgc atatgccct caacagcaag attgtttagc aaccaatta
633301  tgcttttct tatacctata ctgttatggc taattatgta ttgttattaca tatgcttt
633361  tgaattaatc aatgtatat gcacttgatg ttcctctta gggaactgac cacagtgata
633421  agttaggaa atagagatac ttcaaattag aagaaatctt aggagcccc aatgaagtct
```

FIGURE 11H

```
633481 agcagttgat gtaaaggttt cagaaattgt cctgtgtatc catgaaaagc tgtttcattt
633541 ccattttgca aacattcag gaaacttttt tttattaaat tgtatttctt ccatagccac
633601 tagccagct agtggaagaa caacaaaatt ggaaaagcac agcaacaagc ctctgcctag
633661 taaaaaccaa gaaagcaata aacctttgcc aagcctataa gaaaaattta aaagtccacc
633721 gtttatttat cttgttgttt agatatatct gtctcattgt taagtcattg tgaatgcagg
633781 gatttataaa ccctacacta ttatcactgg agggttccca ctgctttag aatagagtgt
633841 tcctaaaaaa aaaaaaatcc attcttttta ctttattgac aagaatagat tatttcaggc
633901 tttgctggat aatcccatct ttggccttg gggctttaaa ccgtgttttt ctctaacgtt
633961 ctggttgatg ctggtaatga gaaccagttt tactgatcat agaagtatga gctcagagtg
634021 actcactaat tccaatgtgt ttccaatggc caacttgaaa aagctacata gggggatgtg
634081 agagctaaat tactgaagac catcatgttt tcctgtgggg ttttccatg ccctgaatat
634141 gttatacatg cttttgttg gtgttttctt ctctgttcta tttgacattt taaagagcag
634201 aagtttaaag taagttcttt aagaatccgt aacagtatgc ccgtatctcc agacaaatgt
634261 ttacaaattg gattgtggct caaagattta acttccttc atgtcttttt ctaaatacaa
634321 agttcaaaacc gaaattgtca agagtgagga ttcattgaca gacaatcagc aggagtcct
634381 tttagtggaa tattacctgt gatacaaaag gattaaacat ttcaaatata aacctttaat
634441 ctgtgctatc taattactga catctgaacc agtatcaagg aatttgtcac ttttttcactt
634501 ttgtaattct aacaaagaaa agaagcaaga agtaattc tgcatctgga aaaaacttct
634561 aatgcaaaag catgtagctt tagtcttttc tcttgagatg gactaggata tgttccctgt
634621 atttctgatt tgtaaagatt cagcaaggca gtctgttac tgcaatcacc cttgcttatg
634681 aagttatgta gacagtccca tgtaaatcag aatgttccaa ccatttgatc ctgtccattt
634741 ctattacaca tggtcaggca tatgatgaga aatgttctgg ctaacacaat ttcatcttat
634801 aactgtccta gaaatgaaa gcaccatggt cagcattggt ttcctagcag agccaaaatt
634861 atgcaaggag gaaagccctt ccatatcct tcatatccct gtactcctc tgataaatct
634921 ttctctcttt ccccctctcc ctacttttcc atttacttt gtgctatac agattcaatt tattagacaa
634981 ttactaaatt acctcatatt attgctcttc gtgtatcttc tcttctttaa tttgttaagt
635041 ttaataatct ccagtgaata tccattaaag agcatatgct ttttccccca tttgttaagt
635101 ttaaaagtca ttagaactag gatttgagc caatctgaaa tcagctagac attccttgta
635161 ttgcttttt tagaaaactt acttatgac tgttcagggg aaggacatat ttgtcctaaa
635221 gcaggctgtt aattatcatg aaaacttacc tattggctgt tcaggggaag cacatatttg
635281 tcctaaagca ggctcttaat tatcacatca gtctagccaa tattgtgatg gaatactgaa
635341 agtaaaggag aaccaaaaat atgtgggttg tattccaga aaaatatatg ttataagaga
635401 atacgaaaca tgtggattgt atttccagaa aaaatgtat gtgtatttga aaattaaaga
635461 ttccttaggg gaagaaaaaac ttgttttaaa ttgtttaat ctcaaggtat ttaaaaatcc
635521 tctgaaagaa tttaaaggc tttccagga tgcaaattat aattatcatg taattaatta attcctgaaa
635581 tgttttagc agaatcaaga acattctgt tgcctggacc ttggaagaat gacagcaatg
```

FIGURE 11i

```
635641  aaaaagttca tattatttgc cagtgtttt ccttaacac tgaaaatgtt aaattgctct
635701  atagttagtg acttattgga aaaacgaaac cagagtcatt cattcctcta ttcattcaac
635761  atacattttt tgggtgtctg ctatgtgcca gcactgcca ttctatattc agttagaata
635821  caaaaccaaa ccaaaaaaag atcctctctt catggaatgt atcttccagc agggaaaaa
635881  taatttaaaa actaaaaaatg ctatgtcaaa tgatgttaaa tatttggagc cagattttgg
635941  taaaatagc aagcaggtgt aatttgtctt ttagaaccc agccattatt ttcaacatct
636001  tttcttccca ctggcgatg tccttcttc aagacgctta gatgttccaa aaggtcattc
636061  tttctctctt ttgctttttc atttaaacaa cattaaaga gaaccacta tgtaccagat
636121  atgtgctgca ccatattcag agatttaatg cagtataaat tatgtatagt ccctgtcttt
636181  atgaaacttc cagtgtattg gggaagagag aaatcaaaatc agtatttaa ggaataagaa
636241  attaaactgg ccatacattc tattaaagaa agattcatgg gactctaatc tcatgcatgt
636301  gtgtgtgtgt gcatgcattt ggtgggattc tcttagagag ggtcatggga ggcagaaaac
636361  aaccgtcaac tcccactaaa ctaatagtgg atgcttctcc caaaacctct cctgaaaaat
636421  ttgatctggt tattagcatc ttgggtaaa tgaagttatc agtagactta agtgtgtgca
636481  atatttttcc tattactttg taacaaaacg tttgtgaacc ttctagaaaa ttccaggcat
636541  cagcaagaag ttcattggtc tttttaggttt ggagtctctct atgctttgga ataatgtcct
636601  ccttattcag attacagaga agtcctcac tctgcatttt catgaggcaa ttatataata
636661  ttgtatatac tatcacaaaa gattaacctg aatataacag gataatgtat ttatggatga
636721  aggaagtgaa gctcagagag gttaattgtc atcactaata tcacacaagt tggtggcaga
636781  gctgggacag gtatgttca attcagttaa caccaactct atttcattat atctggcttg
636841  attttttca ttaaattttg atatgtcagg ttatataatt taacctagag taaatcaagt
636901  tggcagatta ataaaaaatt attattggat tcttctgtat atgaaagaca aaatattagt
636961  atgttatcta tgtcttttaa tgccaatcac attatcttaag attagcatat gaagtaagat  tttatgatt  tagctaaaag
637021  atttttagcaa tcctatcatt atatcttaag ttcatccaaa tactatcata atttaattct ttgtgtccta
637081  ctttgattt gacagacttg tctgacaggc acatgcatcc aaatgtaccg taatttaatt
637141  aggtagtta aaacctttga ttatgttggg tgatatgtct gaggtaaata tgccttattt
637201  cttttgtct caaagttatg ataagaccca cctaatgtt ataaatattg tagcgctatt
637261  ttaatgttca taatcactga agattaatga tactgtttgc acttttataaa agtagatta gataactatg
637321  tcaggttatc agataagtat ctaaaactat atgctaacat tctttcaat tctacacgt
637381  agaaaattct atgtaagtat catataatta atttggacca ttataccaaca ttttttattta
637441  aagatagttt attgttgcag tttttcaaaaac catatatatt aagtctaaaa gatcaaagaa
637501  attttttaag atgagacttt tttttcaaaat gaatagtttc ttctaaagta ataatattt gtcatttcc
637561  ctctgaatca aaccaaatt ttgtaaaact aaaaagttat aaaacaagc aaaaagcttt
637621  ttatattaga tttatctac ttgtaaaact aaaaagttat aaaacaagc aaaaagcttt
637681  atctttttc tttatata tgcttgaatt attttaaaa tgagaaaca attttaata
637741  aggtggaac atttcctact cttttaaaga gtttttcctg attaaatttt aaaactactt
```

FIGURE 11J

```
637801 aggaaatttt gcttataatc ctgcatttat gtaatggcat tgagaataat ttgccaaaca
637861 cagaccttat aatactacag aaacaaatcc agagagcttt actgaccagc tactgactca
637921 ctaaatgaaa gaaaagacc attcccattg aaaataata tcaatattga attatccatc
637981 catggcatgg gggaatacag catctcttcc aggaagtcag agatggacag gtaaaatgaa
638041 gagccagaaa aagaatttct cataaaagaa agtagagaaa ttaagcttc ctggaggaga
638101 aatgcagctg ttcgagctgt ggaatttcaa tgcatgcaga cctcacatct atctcatata
638161 taggtgtgta tacactcgct tcatgtgaac tttgtgaagt caatcattgc tccattgct
638221 aatcccagtt tcaattttg tcagctgtcc ctctatattt tcagtgtaaa tccctgtctc
638281 tttgtaatta taaccaaaac atacatgtgt ttaatcacct ctctatcttg gacaattttt
638341 gtttaatac ttgggatgc ttcatgtgt aggcctaggg aatcctgcct tgaactacat
638401 tcaagggca ggaattctag ctgcggattc ctgcgattc catttccctg taaaattatg cagcctggc
638461 tgcataatgc tgtcactgcc tgaagcagct gctcctgctg ctttcagcat tgtacattgt
638521 caactttct gtcacttcat tcacaaactt tgctcccaca ttgttcacat aatcatctct
638581 ttgcttcttc ctacacccag atttaagga aaataattat gaaataattt ggtagatata
638641 atatgattt agagtagtaa ctccagaact cttagaaaa gccagttgtt cccttattga
638701 tctctctact tttttttaa cgtacttagg aaaaaattgt cgcatgacta tttaccgcag
638761 gtctgactca agggaaaggt catgcatggc agtaataaga agcaagatcc tcacagacat
638821 gctgaaaatt agccacatgg ggttataatc aaaccagatc aagaaaggtg actgagacca
638881 aataaaatga aatgtgaatt gtcattcact tttgctggta agttttgaaa tttgaaattg
638941 accagcaaat ttcctactcc tcttgtgtct ataaactgaa aaactgggaa gttcatttat
639001 tctttgacta ctagtaattt tgtagtatga gtaaattgga aagtatgatt actgttcttc
639061 acaatgtaaa ggtttaaaag aatgccaaac taagcactgc atttattgt tgttttccaa
639121 agccacaggt aaataaaaag tttctgttt ttctgaaatt tttgcatact actactttca
639181 tccaaaaac aatgtcctaa atagatgatt taaccatgtg agttcacact atagctgtgt
639241 cactaggatg gggtgaaatc atcatttcat atttggatat atccttgaa tataatttt
639301 tttaacttg acaactaatt tcctgattcg ttaaagtccc taatgaatat acataaaata
639361 gttaacttaa atacttcaga taggcaggtc atggtggctg atgcctgtaa tcccagcact
639421 ttggaaggtg gaggcaggca gatctcgagg tcaggagatc gagaccatcc tggctaacat
639481 ggcgaaaccc cgtctctact aaaaataaa aaaattagcc agtgtggtg gcacgtggtc
639541 tcaaaaaaaa aaaaaaaaaa acctcagata tgattataaa ccagtgaagc tttaatattt
639601 ttaattaagt ttgaattgtg tacatttggg ggtgccgtgt aaaaatacaa ttttaaaagg
639661 aagtcttat accgaggcca ttggatatta atatttgttg ggtctagcct atgaagaaat
639721 catgaatta taatttgact tttgttttg gttgtgtt gttgttttga gatgggttt
639781 cactcttgtt gctcaggctg gagtgcagtg gcgtgatctc agctcactgt aacctctccc
639841 tcccaggttc aagtgattct cctgcctcag cctcccaagt agctgggatt acaggcgccc
639901 gccaccacgc ctggctaatt tttgttttt ttaatagaga caggtttct ccatgttgac
```

FIGURE 11K

```
639961 caggctggtc aggaactcct gacctcaagt gatctgcctg cctcagcctc ccaaactgct
640021 gggattacag acatcgagcc gcagcacctg gttagtttt tttaaccct ttataaaata
640081 cccactatag tcagaatagc cactcagaat atgtgggtta gctgaatttg ctatcccatt
640141 gccatacaaa ttctaaaagc tatcaactga cagactgttt ggcaggggg tgggggct
640201 ggggtgcag caaaaatagt caggaggaat gacacaataa aatattacca atcaattaac
640261 cagtgagttg acaactggcc ttgatcagag ctaaggagaa agagggctct ccctataatg
640321 agctgtgatt aacaacagga attaccgaaa tgtaattata gccaactctt cagagatgag
640381 ccatccatgc cttgagactt cagggtctca gtaaagatag agtattttt gttcttgatt
640441 actaagataa caattgagcc atgtttttag atgcaatccg gtgtgtctac aagccttcat
640501 catattttag agttattcc ttcctacagt atgtttttca gcttgatact cagtgatctc
640561 aggcttattc ctggggaccc agagcctcct gctgaagcaa aacatccagg cttgctcaac
640621 atagacagtc ccttaactta cagtgggaga tgcaagtctt gtggctcaac tgtgactcta
640681 ggagttgagt ggtagtagca tcaccagtcc aaaatttcag actaaaaaaa agacagaaaa
640741 tgacatggca tctccaataa tgtttacttt tgtgaaaat tgtaatctcc ttgattactt
640801 tatattgcat ttgtgaaact tactctatta tagcttgtta aagtattta actgtaattt
640861 atctctcagt tatttcacag caagatataa cagaggccgg gcacgtggc tcacgcctgt
640921 aatcccagca ctttgggagg ccgaggcggg tggatcatga ggtcaggaga tcgagaccat
640981 cctggctaac aaggtgaaac cccgtctcta ctaaaaatac gaggctgagg caggagaatg ccgggcggg
641041 tggcgggcgc ctgtagtccc agctactcgg gaggctgagg caggagaatg gcgtgaaccc
641101 gggaagcgga gcttcagtg agccgagatt gcgccactgc agtccgcagt ccggcctggg
641161 cgacagagcg agactccgtc tcaaaaaaa aaaaaaaaa aagaaaaaa gatagaaact
641221 cagcattcgt gaatggatga attaatgaat atctttattt ctaaacactg tacagtacca
641281 aaatatcttt taaaaagtta tgaaggctct aacattgcag acggtttggc atatatacta
641341 taatttgagt accccctag tatttcaagt tgacacaatt cttactacta aaagtattgc
641401 tttatcaatt tcaagcagc taagatagac ttctttaaaa acagatcaat tttgttct
641461 aaaaatatat cctaatatca gggtattatt ctaccacaga gaattcacat tgattgtcta
641521 tccatttaaa acaatatagt tatagtcttt tggaactttt tcaacagactt ggataagctg
641581 gcggtgtaaa catttcctcg tggaacttta ataaatgaa aagaaaataa atgattgatg
641641 catactccaa ctaattgaag tgtactgtag tcaaccagat gttttcacct gaatcatgcc
641701 cacagatgct attgcttcat tatcccttaa tctagggatt acctccattg gctaactga
641761 tgacctgtga gggtttcaaa taagattgcc tctcccttgt aacatacatc ataaagagag
641821 cttgtttaga ggcagcctac ctccgcctg atgtgtctt cagtgaagtc caaggaagtg atcagggctg
641881 tttgttttc ttgctgttgg acaatggagc tatttccaca gctggctgca aaggaatggc aatgagagtg
641941 gccacagttg acaatggagc tatttccaca gctggctgca taaacatct gtcacaatag agtccatcac
642001 agataaacta gcacatggg atagatgata taaacatct gtcacaatag ggataagcaa
642061 aaacaacgtg cctttgaaga ttgtgttta atgatgaggt ggggtct gtctctataa
```

FIGURE 11L

```
642121  taggaatgaa  agatgtgttg  ttggtgggca  gatggcttca  ggcttgctct  tgcatgaaat
642181  aagcaaaag   tatgtgttaa  aaatctctga  cagttgtcaa  gtcaacctgat tttgtgacc
642241  gttcatttcc  ttgcctatcc  catgtgtaat  ctatgagaaa  agaaagggag  tgctaggaaa
642301  aaataatggc  agaaaaaaaa  aactggttct  gaataatttt  cttttggata  actttaatac
642361  atcagtataa  ttttaactgg  aggctgagag  gtcagaaaac  gtgtttttgc  aataagtttc
642421  tttaatatat  ttgcatcccc  atgttttttt  ttatagaagt  tttgtaaggt  aatataaaaa
642481  tgctatgtca  ccaagccac   ataatgataa  atatttcaaa  tgtaatacc   aattagtaga
642541  cataagtcc   tatttgttcc  tgttaagga   gcagtgagga  aaaataaaga  catcttaata
642601  aactatttt   gatgtaatta  taatagtttg  gttcccacc   ccatctgcct  ttgaaaataa
642661  attaaaaaca  ataaaattca  catacagttt  tatttcatat  agttgctata  gaaaaagaaa
642721  tctttgcaac  agacaaactg  attgcaaata  aatgccgaat  attcttgcac  aatacaattc
642781  tatatatacc  ctgttacatg  accaaagggt  accactgtca  atgctgcac   ccaaccatt
642841  ccactctgct  ctggtaagga  aatggttgc   attgctgcac  actgaaattt  tgctacttt
642901  gccacaaccc  caccggaaaa  atggatgtca  cattccttgc  tcatttatta  tttaatctg
642961  tctttcaact  ctaattccct  tgcaggtgct  tttgattagc  agaagtcaca  aatctatatc
643021  tagcagcaaa  agggtgtagg  aaatgttttt  agaaggttt   tcttttcttt  ttcttttt
643081  cttttttc    aattctacat  tgaagagta   ggattcacac  tggggaaac   taatgacatc
643141  tgaagagagt  attaaaaaat  aaatttctac  atccatgaat  ggcagagta   caccacaaga
643201  agcaactgga  ctggtcaaa   taagagatct  taaagaaga   gcagtgccag  gcatggtggc
643261  tcacgcctgt  aatcccagca  ctttgggagg  ccaggggcg   gatcaacctga  ggtcgggagt
643321  tcaagaccat  cctgatcaac  atggaaaaac  tccgtctcta  ctaaaaatgc  aaaattagcc
643381  aggtgtggtg  gtgcatgcct  ataatcccag  ctactcaaga  ggctgaggca  ggagaatcgc
643441  ttgaacctgg  gaggcggaga  ttgcagtgag  ccaagatcat  atcattgcat  tccagcctgg
643501  gcaacaagag  cgaaactcca  tctcaggaaa  aaaagaaaaa  aaaaaaaaga  gagagagaga
643561  gaacagattt  aaaggaattt  gtgatgttct  gacaagactt  gactcctgac  tgagttttat
643621  ggctgatgag  ggagaaggaa  acgatcaaga  tgacttagga  gttctttgt   tattctgaga
643681  atcagcaga   gaagaaagaa  tactctgaga  atgaaagagg  aagacagcat  tcagagcggg
643741  acatagtagt  tttgaggtac  atgggattcg  gtcagtagtt  ggaaatttgg  atcatgaatt
643801  cagaagaaac  accaaggcaa  gaaagactt   tttaaaactt  taatttttaa  actaattata
643861  gcactttga   ttaatcaagt  cttaacaagc  gggaatattt  tggaattta   cttctaacac
643921  cttatttta   tggtatgtat  attgagctaa  ccaaatatt   tgctgctgt   ctcttactat
643981  tctatgcggc  atataccatc  tcttctaatg  cttgctgtc   atagctattt  ctaactcact
644041  ggttaagcag  atgacgttat  ttggaaagaa  tggagttc    agtgtgaagg  ttgccatgaa
644101  aatatgtcat  aggaaaagaa  agggaatttt  tttgttaaag  gagattttat  gggtaaaggc
644161  agaaatcgta  tggagatgat  tgaggaacta  tactaaaat   cagtggctgt  catttataac
644221  aaggagttat  attaatatta  ctaatattat  tccaagctat  ctggctctca  agcaagaaca
```

FIGURE 11M

```
644281 aacaaaggac ttaacaaaat gattgagagt caaaccaaga atcttttag aagcaatgta
644341 atagaaaatt cactcagagc cctgcagac caatgcaga gctaagttt ccaagttta
644401 tcgtgaatat aactcactg ggcaggctc taatttagtg ggctgggt tcacctgaga
644461 ttctgtacta agctcctga tgatgtatc cagtcccagg ccatcgtta agaaacaagg
644521 tagtagagtt taagaacatt ctattaaact aaaaaaaatg ttaaaattaa tcatatagta
644581 ttactgctta ggagaaatgg caataaaatc taagcggaat aaaacatgta actaagttc
644641 ttgcacaaat cctgaaacaa ataggacact gaaggataac aagataaagc tgtctttat
644701 ctcatctgga cagtttaaa tatattaatt gaaatcttga aggcctcaga atgtaactg
644761 tttgatgct aatatataag ttttaacctt agaatatgtc tgttacacca ggacatattt
644821 tatctcagca ttagaccaca gaacatgtca tcaatagggt atatactgag tttgaagcat
644881 gttagcaata ataatactaa tagaaagtgt gcttaaaaag gagtaaatta gttctttat
644941 agggtcgtga cttcacacct gtatccttag atctagttaa gtttccagcc ctaaccagc
645001 aaattcctaa aaatatctta aggagaaaa atattctctg agggaccaca aaataagtg
645061 ctttttgcag caaattgcag gacaagaat agctactttc ttagtaatag ccaaaattg
645121 agtgccttg tgacatattt aggcaactg cactataaac aatgccata agtaagataa
645181 caggcagcta tttctcttga tcgccctgt ggtttgagca atgattttcc agcccattt
645241 gccaatagga tcttacaaga ccttgaaaag gatttgcaag caggtcttc agtctatttg
645301 tcagtaagga gaagttta atgagaagtt ttatgacagc tcacagtct gagtcctagt
645361 taaaccaga taaacatttt accagacaaa agatgaggtc cataaatatt cagacgtctt
645421 ctgggaaccc tgtttgcctt atcatttgga agaaggctgg cctgagtact gcatccgatg
645481 tgtgcttgaa acttctgtaa gttgaaaatg tgtttggagg tatacaaagt gattgctgta
645541 caaatgaata aagcattct tatcacatga caaggttga caagaatctc aggcagatat
645601 atggctacta aaacagttca tggcatagca aagtcctaat ttaaaaaaac ttaacctaca
645661 tttgtgcag tacacattgg ctgtaatatg ctgcagcat cctgaacat cttgcagcat ttaactgagc
645721 ataaataatt cttccataga atgaaaatca tgtcgtgaac aaataatgag aagtcaagc
645781 ggtgggtgt ggctctcaga agccctggga tttcatact tccaatgtta aacttccttg
645841 tggcagtggt cagactgaga tactgtcaaa gaaaagcaga ggaagtgtat gaatggatct
645901 tttacgtcca tctttttggc cagagaatgc ttctggtatt tccattgaat cttcttgtcc
645961 agtttgagca aggagctgct gttattgttt cacataccat taaagtcatc agagacctgc
646021 tggtgagcaa gtgccattca ctcactcagt ccattagcac cactaactaa gcatctgttt
646081 tatgacagac actgtgctgg gctcagaacc attaaaaaag aaatataaa ggtattgcta
646141 atgataccag tgaacttagg attcagggaa gaaataaagt ttgatcatga tcaaagtgtg
646201 tgcaaaatgt tatgggagaa gagaggagca agtgaccggt agcctgggtc agtcatagga
646261 gttattcccc agaattagt atttgataag aatttagaa gacacatata aactgctgta
646321 gaagcctagc gttgcaggcc aagacagcaa gggtaagagg taagacggac aagagaatga
646381 tgaggaatac agtgtggtgg aaagagaggc ttcatgtgca tgggctgggg atcaggctag
```

FIGURE 11N

```
646441  aaagtaaat  tgaaagctgt  gtgatcctcg  tagattatgt  gtgctatgct  aacaaggcca
646501  tcccagacct  acctgtagaa  gcctctttt   gacagagata  atgctgaaac  agagtagaaa
646561  gcacatgctc  ttgggcagcc  ctacaactca  ttcactctaa  ctggtttctg  aataagacaa
646621  gcaggaatag  aaaaatgtct  tgtcctgtca  ctgaactgtc  ctatctactc  ttacactcct
646681  ccaacacatt  taatgtagaa  tagccattga  cttaacagta  ccagtgtctt  aaaaaggaca
646741  tttccactat  gaaaaactaa  cgcagctcta  ggttgcactt  tgggaaagga  ggtcatttaa
646801  cactgtttcc  cttataaccc  cacttagaac  aaaaataag   gagaaactgg  tctgctcctc
646861  ttcaaatttt  atatatatat  atatatatat  atatatatat  acacacacac  acacacacac
646921  acacatatat  atgtatatat  gcatacatat  acatattgtt  tttaaggtag  aaaaaattag
646981  gaactaatct  caatatttca  aatataattt  tttattatga  aatatatttt  gtgggtagag
647041  atcaatggtt  ttctttctaa  aaaaagtata  gaaggagctg  aatatatttt  gattaatcaa
647101  ttcattttta  agtgtcatag  cttatagtc   tttgtcttt   gattcttttt  gtcttgtgct
647161  gtttttgatt  cctttaaata  aattttggag  tgtgcaatac  atctgtatag  gaaagctata
647221  taccatgggg  gccctgcaaa  gcaaagacta  aggactatgg  ttatgccact  aattttttca
647281  cacaaatagt  ctcattttt   cacattatct  acaccacaac  acatgtattt  ttatgtaaac
647341  tacagcagtt  tacatgtgtc  tcctaaaatt  cttatcaaat  accacattct  ggggaataac
647401  tcctatgaat  gaaccagact  actgtcact   tgctcctctc  tcctcccata  acatatttga
647461  accaggctac  tggtcacttg  ctctctcttt  ctctcataac  atatttgaac  caggctactg
647521  gtcacttgct  cctctcttct  cccataacat  atttgtgagt  gtagacacc   cccagctgaa
647581  agctactcat  tagttatgcg  attggaatca  gaagctgatg  aacacaagtt  caccctttgt
647641  cattgaagct  ctaaggtcct  tctgaagtgg  cctggatct   ttctctaaac  aattaatatt
647701  tccattgact  cagcagttat  gatctcctta  agtaagaaaa  taagaggaaa  aaatatagta
647761  accatctgt   gtaagaaatt  tataatctta  agatcaattc  tgtaatcaag  tgtacaagtt
647821  taatgacaaa  ataattaagt  gtcctattgc  atattcagtc  aacaaaatcc  ctttgaccgt
647881  agagtcctca  aaatctcaaa  ttttcaactc  ccctcaata   atgcaatata  tttaaaagcc
647941  actttgctct  attaggattc  taaagaagct  actgaaaaca  ccaaaagcta  ctgataaact
648001  tgtttctgta  gttttaggca  caaagctga   aaggattaaa  ataaagcatt  attgagaatc
648061  ctaattatct  atgtacctgc  tttgtaaga   aatacttcaa  tatgacatat  ttactttata
648121  ttctcattca  aaatgacact  attatattaa  taggtactta  accaataatt  gaaaccatta
648181  ttcacagttg  aataggcgta  gtacataatt  aggattcttt  taaagggatt  tccatggcta
648241  aaactaattt  ggctttagtg  tctattaata  ttataacttt  aaaaaaaaat  acttccagtt
648301  actagttact  gaatcaaaaa  tcaacttgaa  attaaaagtg  tgattaagag  tacaaggaaa
648361  aaaatgctat  gtttataatt  aatagatatt  ctgttattgg  gaaatctatg  tacatgtaca
648421  tatctcttct  acctttatca  tatagcagtg  gaaatgtct   tacttctaaa  cattataccc
648481  ctagcccata  gctatatatc  tccatatagt  agtcccaata  tcatgccaat  tagtctaatc
648541  ctgtccaagc  ataggaaaga  gaaacccagc  tctagtttgc  cccatttcca  aataaatag
```

FIGURE 11O

```
648601 caaaataagt tagcactcaa aaataatgat aaagccattg gaagtcatgt aatagtcctg
648661 ttttctttca ttgcacaatt atgaaatttg ggaaattggt gtatattata accataatct
648721 tgccatagat ctaaaatgtg ctattagttg tcggaacag actgtagatg aatactttgt
648781 gtcacttttc tttctttctt tttttttt tttttttga gatggagtct cgctctgtct
648841 cccaggctgg agtgcagtgg catgatcttg gctcactgca agctccgcct cccggttca
648901 cgccattctc ctgcctcagc ctccgaagta gctgggacta caggcgccta ccaccacgcc
648961 tgcctaattt tttctatttt ttagtagaga cggggtttca ccgtgttagc caggatggtc
649021 tcgatctcct gacctcgtga tcgcccgcc tcggcctccc aaagtgctgg gattacaggc
649081 gtgagccact gcgcccgcc tactttgtgt cattttcta gttactgcct ttcaaattct
649141 tcctcacttt gtataaatgg agcttatgga tatatgtata tatggaccag ggtttctgaa
649201 ccctagcact aatcctgggt ttgctggata attatttgtc gtggggaact gttctctgtg
649261 ttgcaggatg tatagcaaca tcaataacca ctacccccta ggtgctaata gcacacctcg
649321 gcagttatga taaccaaaaa tgttaccaga cattgcaaaa tcactcctgg ttgagaacaa
649381 atgaaatatg tacatataca aatactttttt attctaatat atatatatat atttatatgt
649441 ctcatatagc attagtcaaa ctttttcat caagcaaaatc ttgatttca tctttaaggg
649501 gatggtggtt gaagatgtca ttaatgcgca tgtgtgagtt gaactatgt tttaaaactg
649561 aactgccct tgggagaaca agttttctca agaattttgt aatgatccat tttaacgagc
649621 aatctcaaaa taacattct aactaactac ttttgatta gaagttttat tctttcatca
649681 ttctttcggt gaactcttat aaagcatata ttatatacct cacactataa acagcactat
649741 agacactaga cagtggtgaa caaacaaca taatttcaac cctttcagaa taaacaatca
649801 aaatgagaaa tattagtaaa tatttacagt tgttcattga actgaaaaat gagtggtact
649861 gatatataaa attaatttac aaaaactgtt ttgagtactt actgcatgca attcctattt
649921 atagagatta caaaagttgt ataaacataa tgtcttccct cttgaaagat gtaacgtgga
649981 aagaaacaag tagacaataa taaaggggaa ggaggtatta agtgctaaag tgaagttcta
650041 gggcagtgt ggcttctggc ttaccatgta attcatcatt tcccatacct ccagcatttg
650101 tcaaatcctt ccaaaatgct tacaaagtta aaggctacca cctttgccac atcttttgaa
650161 tttcaaacat aattttttaa agttggactg cactactacg ttggttggaa atttatcaag
650221 gtagataagg attaatgatt gttctaaga attagagaca tttcttactc ctttgtttc
650281 ttctcccac aaaagccttt cttaaaccct gaaccctcat caaaacaaaa caaaacaaaa
650341 caaaacagtt gacatcaaca aatgaaagaa attagacatc cctacatata ctacaagaca
650401 aggaatgttg catgctaata ctgcagaaca ctgcatttgg acagctattc ctcaagctac
650461 cttcatgcca tttatattat gagatctctg ttgctattag gtatttgttc taggaatatt
650521 aaaaactggc aaaaatcaga catgaataaa agaataatga aatagtgact taaaaccacc
650581 ttttaaaat tcatatatag tttgtgtga ataactatag acacagcaga gcaatcgtat aatacaaatc
650641 acagacattt tgacttgagg cattagata agacagcaga aaaaagggga tgctgtttt
650701 ttaattttca cttatccaaa taattttatt tttgttttc cattctatg agttcaaatg
```

FIGURE 11P

```
650761 caaggctact aagattccaa atatgaagga ttcccaatgt gttataatag aagccaaact
650821 gatcaaattg aagcatgtca ggtcatcaca cttattcagt gattatatgg tgtgattatt
650881 cagataatat ttctaggtca gcccatcaaa aatgcaggct tagcccttt gaatgttttt
650941 aacaagatat aatgtgatta tcacataaaa gaccatggcc tgtaaaaaga ctggattcaa
651001 acaaataaat gagaaacagc gtacataaaa taaagccact tgtttgctg taagaactgt
651061 aacactggct ttatacgata gcagttttta gacagagcat acttcttaaa ctttagagta
651121 tatcagaatc acctggagag cttgttaaaa tacagatttc aagcctaat cccagagagt
651181 ctaattttg tctactgctg ctactgatcc acaaaccata gttgggtgg cactgaccta
651241 gaatactatc acaggaatat taatgcagct agttcttctt attgtggttc atcttctggg
651301 attaatatag gtgctaaaac agctatgtgt gctctagatg gtagagaagc cacacatgct
651361 tttccctgat ttgcaatgg tttgtattt cagtgggaa attaaaatat tgaactttca
651421 aagacttcaa attcttttca aacattggca gaagttaac aacacagatg ctttctggc
651481 cttagtcag atatatttac gccacacatg atgatcttg gaaacttac ccaaattact
651541 gttgaaaatt gttatttca gaactagggc aaccagatcc accctttgtc tcttgagtgg
651601 gagcagcttt gttttgcaaa ggcagtggct aaaaaggacc agaccttc atcagctgtt
651661 tggtcattgt attttttagt ggaattatag cattgtacaa tattttctt tgcagcccaa
651721 acattgagca aagccagaca tccagagatg ctaaaatgaa aaatctgttt cttcttgctt
651781 tgccacttgc caggtgaact ctgtcagaca ccacatccta tacatctcaa gtaaacaaaa
651841 ttatgcttaa tgtgttggca acatctgtca caaacactct tcagcctatg gcttaaatat
651901 attaagttgg agtgattg acagtgtatt taataagtca aagttacgt tgggatact
651961 ggctttgcca tgctaaccat aaggctttc tttctctt ttgtatttat ttattatgt
652021 catatacaat acaaaagaga ttctgtagtt ttaaataagc aagtggctg gcaaactcc
652081 cctttgctgt aggtaaccaa cactaaacct ctctaagttg tctgtcccag acaaagtatc
652141 attaagaaaa ttcattctc ccaggagttc ctattagtta cttccagttt actccctgac
652201 tgtacatttc ttccattccc ttaagattaa aaaatttgta ttcttaataa ttgtaggat
652261 tgttttcact gaatgtttt attgaatgca aacaagactc tagattctta catatcctc
652321 cccagaatc cttatttat ttttattta tgtgcaataa ctgatctgct tagaagaac
652381 tgttcattta tgtgcagtaa ctgtctcct tacattattt tccactctgt gcctagtgtt
652441 gctatttaca attccaatta atgataaatc ccttctact tttcccttg attgtcaggt
652501 ttctggttta tacacagaag caacactcac tctatgacat ctgtaatcaa atgagtcccc
652561 aaatatgct ttcaatgaa agattctgaa agagacaga caattcttcc aaaattaatt
652621 ccaagtgcag gcattcgatc cttctcatca tgcatgaatt ttgattgttc tgtcacatgc
652681 tcacctacct catctgcata ttgccttaa aaaaaacaca cccctgggga atgagacaac
652741 ctccagggta ttgagaagaa agtatcctta ccaaacgcag tttgttttt atctctgatt
652801 tacatgaatg atcctttg tggctagagc aagctgttta gaattgaggg gtttctggga
652861 ttgtgacagt ttagctgcat gttggaatgt ctaagggcaa atattctaaa agataacct
```

FIGURE 11Q

```
652921  gtcttgagtt  caagaagaga  atcgaagtct  tgcagctgct  aagcattaga  atgttgtcaa
652981  agtaccactt  tttggttgaa  aaaaaaaaat  gcttcaggac  ttccatctta  actctgaggt
653041  tattctataa  tttatccota  ggtgatttaa  gaagaaccct  tgttctctt   aaagtgttta
653101  cttctggtct  ggcacaacaa  atacctgaaa  tgaaggccag  taagtatttt  ttaaaaaagg
653161  aaaacaataa  agatggtttt  gttaaaaaga  ttcaggcagc  agaaagaaaa  gtgatgtgtc
653221  tctgaattat  aattaagtaa  aagcttatct  tatgttctc   atttaagagg  catcctgatg
653281  aatgacaatg  cacagaagca  tcgagaaatt  caaacaacac  aaatgcacaa  ttgtgtatat
653341  ttacaagcta  cagacctta   aaataacaga  catgttttct  gattgattcc  tactgaaaag
653401  cctaaatgtc  tttgtgaaca  aagctggccc  tgtatatcaa  gcatttccaa  atatttggct
653461  caatttctat  tatctctgaa  aattaatggg  gaggagccca  cagagaaggc  agagtgatag
653521  cctgatcttt  ttcacagata  tagtcaggaa  gttgaatttc  gataatacca  ggaagaattg
653581  cttagtttga  gcaaaagcat  tttaggaaac  gcgcagtggg  taattagttt  gggtgccgag
653641  atctggccat  ctacatgcat  ctgtccagtg  agaaaaataa  tgtttaggga  aataatttat
653701  tcagatacat  aatcatttga  tcataactga  gtatttaaat  gggttgttat  aaaatatgtt
653761  tctactttta  tcacaatctt  taaataaaca  ttgaaattat  atactctcaa  agattccatc
653821  caattcaagc  ttttaagtt   tgtttttta   aaatattttt  cottctccaa  gttaattact
653881  gcaaggaaag  tagcagggta  gagaaagaga  aatggaagga  taaaatgact  tagctccatt
653941  cttcactcac  catatgacac  tttgcatatg  gatggaagtt  tttaaaatg   tctgtaattt
654001  cttttatccc  caacaatgat  aataaatcaa  aagacatatt  ctagacatcc  acttcctta
654061  acatctgatt  taaaagttga  cacttttatt  tttaaaaaaa  aattgtggat  ggacataaaa
654121  atttgaccag  ctctaacaga  gttggtatt   ctgtcttgtg  tctaaaatat  agatagatag
654181  aaaacaggtc  aaaaggttag  gaggaaaaca  aatgggaaat  agtaattcg   attttagat
654241  tatcaatgat  agattttaat  atgtccttca  aagagatcca  gttcagaaac  ccatgtgggc
654301  cagcattatc  cctcttagtg  gtagattgta  ttgggtgac   taagaattat  gtatgtatta
654361  ataagtaata  gataaatgac  ataaaccaag  tcttatcaa   taacaagaaa  attagagaat
654421  ttccactaat  gttcatatgt  ttcagtcaga  gaagtttata  tttagaacag  tgggcaagag
654481  gatatagatg  attttcaata  cattctacct  caaaaaatga  aaatgtaagt  gacatatttt
654541  agacacatca  caggtaaatt  acctcagaag  aaaggaagat  gttaatgcca  tctattcaga
654601  caagcacaaa  atgacatgaa  tggacataaa  aattatatac  agttgaattt  agccttttta
654661  gtaaaaaagt  aaaaacatt   gatgttcaca  catttacaat  ttacagtgtt  tatttgtaag
654721  aagtctcctt  cctgtagga   tatattttca  aatgacatt   gtatatgctt  gtagggtgct
```

PHARMACOGENETIC TEST ANTI-RESORPTIVE THERAPY-ASSOCIATED OSTEONECROSIS OF THE JAW

PRIORITY CLAIM

This application claims priority to U.S. Provisional Application Ser. No. 61/471,532, filed Apr. 4, 2011, the contents of which is incorporated by reference in its entirety herein.

SEQUENCE LISTING

The instant application contains a Sequence Listing which has been submitted in ASCII format via EFS-Web and is hereby incorporated by reference in its entirety. Said ASCII copy, created on Nov. 19, 2012, is named 07005045.txt and is 59,951 bytes in size.

GRANT INFORMATION

This invention was made with government support under Grant No. DE018143-01 awarded by the National Institute of Dental and Craniofacial Research, National Institutes of Health. The government has certain rights in the invention.

1. INTRODUCTION

The present invention relates to methods and compositions for determining whether a subject is at increased risk for developing anti-resorptive therapy-related osteonecrosis of the jaw.

2. BACKGROUND OF THE INVENTION

Bisphosphonates (BPs) are widely prescribed anti-osteoclastic medications. The intravenously administered BPs pamidronate and zoledronic acid are used in oncology to control bone metastasis and hypercalcemia. Oral BPs are used to control or prevent bone loss in osteoporosis, including osteoporosis associated with menopause. An estimated 3 million American women are currently being treated with oral bisphosphonates [1]. The monoclonal antibody Denosumab is also used to treat these conditions.

BPs are synthetic analogs of pyrophosphate that readily localize to bones due to their affinity for hydroxyapatite, and reduce osteoclastic activity. They are not readily metabolized, and thus, have long-lasting effects that might extend for several years. BPs are especially attracted to, and localize in, areas of the bone undergoing inflammation or resorption. They are subsequently phagocytozed and internalized by osteoclasts. These internalized bisphosphonates, in turn, trigger apoptosis (cell death) of the osteoclasts, thus inhibiting osteoclast-mediated bone resorption [2]. Osteoclasts seem to be affected by BPs both in terms of number and function. Animal studies have also demonstrated some antiangiogenic properties, which may partially explain the development of osteonecrosis due to limited healing ability of the bone because of reduced vasculature [3].

BPs, especially zoledronic acid, have been associated with a serious adverse effect, osteonecrosis of the jaw. According to the American Association of Oral and Maxillofacial Surgeons (AAOMS), BP-related osteonecrosis of the jaw (BRONJ) is defined as exposed bone in the maxillofacial region for more than eight weeks in patients treated with a bisphosphonate that have no prior history of radiation therapy to the jaws [4]. The non-healing exposed necrotic lesions may involve the mandible or the maxilla or both, and can be painful, persistent, and resistant to treatment. The incidence of BRONJ varies in different studies. BRONJ affects as many as 5-10% of zoledronic acid users and far fewer users of oral bisphosphonates.

Osteonecrosis of the jaw has also been reported in association with denosumab treatment [29]. It would be desirable to identify individuals who are at risk for developing osteonecrosis of the jaw, so that subjects at greater risk could be considered for alternatives to anti-resorptive therapy or, if suitable alternatives are not available, could be monitored more closely.

3. SUMMARY OF THE INVENTION

The present invention relates to methods and compositions for testing individuals to determine whether they are at increased risk of developing anti-resorptive therapy-associated osteonecrosis of the jaw ("ARONJ"). It is based, at least in part, on the results of a genome wide association analysis which revealed that certain Single Nucleotide Polymorphisms ("SNPs") are significantly associated with osteonecrosis of the jaw among bisphosphonate users, including SNPs in the RNA-binding motif, single-stranded-interacting protein 3 ("RBMS3") gene (for example, the SNP rs17024608) as well as SNPs in other genes, including but not limited to those for insulin-like growth factor I receptor ("IGF1R"), insulin-like growth factor binding protein 7 ("IGFBP7"), dihydropyrimidine dehydrogenase ("DPYD"), ATP-binding cassette, sub-family C (CFTR/MRP), member 4 ("ABCC4"), and glutathione S-transferase mu 2 ("GSTM2") and other SNPs as listed in TABLES 1-5.

4. BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A-B: Population structure of Caucasian subjects from the combined ONJ/Hap Map 3/European collections. The red circles represent ONJ subjects, azure dots CEU Hap Map 3, blue dots CEU Hap Map III, yellow dots North European POPRES, green dots central European POPRES, gray dots Spanish POPRES, light yellow dots South European POPRES. (A) PC axis 2 versus PC axis 1 (ordinate versus abscissa). (B) PC axis 1 versus PC axis 3 (ordinate versus abscissa).

FIG. 2. QQ plot for Caucasian ONJ Study Group.

Figure 3:
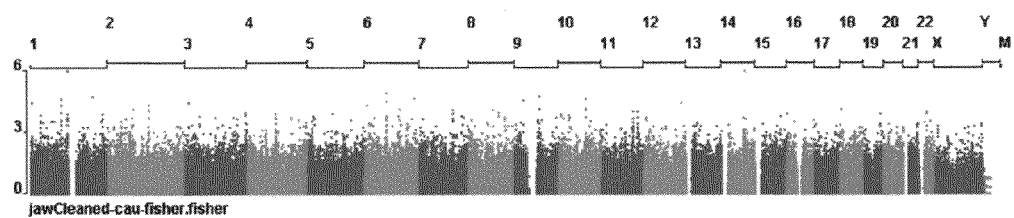

FIG. 3. Manhattan Plot for Caucasian ONJ Study Group.

Figure 4:
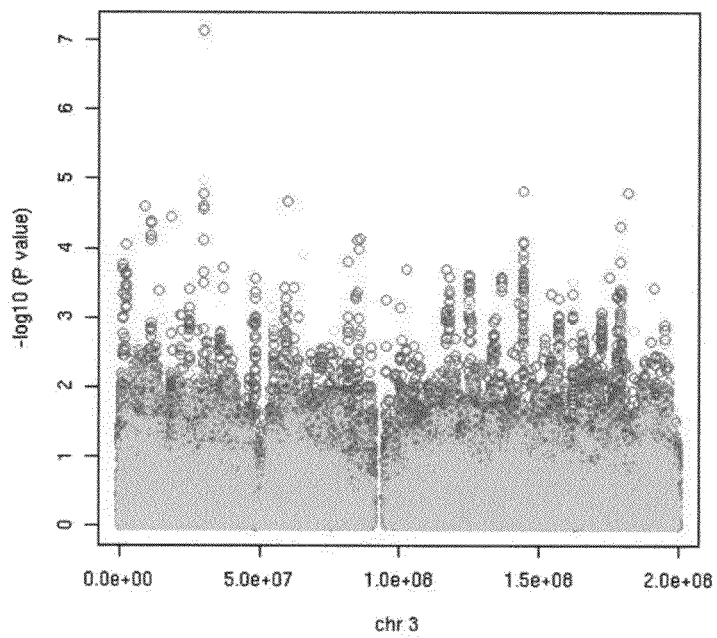

FIG. 4: Manhattan Plot of the region surrounding rs17024608. Red dots represent the imputed markers; Gray dots represent the original markers.

FIG. 5A-B. Results of SNP analysis within 20 kb of IGF gene family candidate genes. (A) QQ for candidate SNPs (logistic test, drug-exposed study group) and (B) SNP quality graph of the top hit.

FIG. 6A-B. Results of SNP analysis of ADME genes. (A) QQ for ADME SNPs (logistic test, drug-exposed study group) and (B) SNP quality graph of the top hit.

FIG. 7A-B. SNP analysis of IGF-related SNPs in the extended study group. (A) QQ plot for candidate SNPs (logistic test, extended study group) and (B) SNP quality graph of the top hit.

FIG. 8A-B. SNP analysis of ADME-related SNPs in the extended study group. (A) QQ plot for ADME SNPs (logistic test, extended study group) and (B) SNP quality graph of the top hit.

Figure 9:
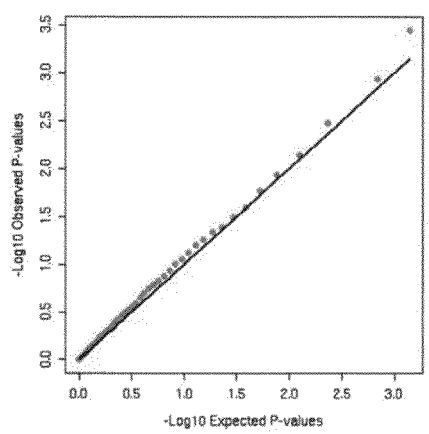

FIG. 9. QQ plots for IGF-candidate SNPs (logistic test, final study group).

FIG. 10A-B. (A) QQ plots for ADME SNPs (logistic test, final study group) and (B) SNP quality graph of the top hit.

FIG. 11A-Q. Nucleotide sequence (SEQ ID NO: 86)of the intron between positions 29941247 to 29977576 of the human RBMS3 gene on chromosome 3 (numbered consistently with their the numbering of the RBMS3 gene as represented in NCBI Ace. No. NC_000003 Region 29322803 . . . 30051886 GPC_000000027). Sequence flanking the A/G substitution in rs17024608 is bolded and underlined, and the variant base (A) involved in the A to G substitution is shown by a capital letter. For clarity, residue 618421 in the figure is residue 29941247 of human chromosome 3.

5. DETAILED DESCRIPTION OF THE INVENTION

For purposes of clarity of description and not by way of limitation, the detailed description of the invention is divided into the following subsections:

(i) biomarker genes and SNPs;
(ii) methods of treatment/diagnosis; and
(iii) kits.

The term "anti-resorptive therapy" as used herein refers to therapy in which an agent ("anti-resorptive agent") is administered that inhibits resorption of bone, for example in the treatment of osteoporosis or in oncology to control bone metastasis and/or hypercalcemia. Non-limiting examples of anti-resorptive agents include, but are not limited to, bisphosphonates and monoclonal antibodies specific for RANK ligand, such as, but not limited to, denosumab.

"Anti-resorptive therapy-associated osteonecrosis of the jaw", or "ARONJ", includes BRONJ as well as ONJ associated with other anti-resorptive agents.

The term "bisphosphonates" as used herein refers to a class of drugs comprising a bisphosphonate structure that may be used to treat osteoporosis or hypercalcemia. Non-limiting examples of bisphosphonates include orally-administered drugs such as alendronate (Fosamax), etidronate (Didronel), ibadronate (Boniva), and risedronate (Actonel) and intravenously administered drugs such as pamidronate (Aredia) and zoledronic acid (Zometa).

The term "osteonecrosis of the jaw" ("ONJ") means a clinical condition characterized by, in a subject, exposed bone in the maxillofacial region that persists for more than eight weeks. Typically one or more region of the affected bone area is necrotic.

The term "allelic variation" refers to the presence, in a population, of different forms of the same gene characterized by differences in their nucleotide sequences (sequences in genomic DNA). The variation may be in the form of one or more substitution, insertion, or deletion of a nucleotide. Different alleles may be functionally the same, or may be functionally different. In one subset of allelic variations a single nucleotide is different between alleles, and is referred to as a Single Nucleotide Polymorphism ("SNP"). Allelic variation in a known sequence may be identified by standard sequencing techniques. A "variation" or "variant," as those terms are used herein, is relative to the ancestral gene found in the majority of the population. Unless specified otherwise, the presence of a SNP means that at the single nucleotide position for which alleles have been identified, the nucleotide present is the variant nucleotide, not the nucleotide found in the majority of the population (however, TABLE 4 lists SNPs and then specifies which allele is associated with ARONJ, and either the allele found in the majority of the population or a variant may be specified). The variation (variant) is comprised of a substituted nucleotide or nucleotides or an insertion or deletion of a nucleotide or nucleotides. Herein, generally the ancestral nucleotide is listed first and the variation (variant) nucleotide is listed second (for example, in A/G A is the ancestral nucleotide and G is the variation (variant) nucleotide). If there is an insertion, the ancestral nucleotide is represented by a hyphen (e.g., -/G). If there is a deletion, the variation (variant) nucleotide is represented by a hyphen (e.g., G/-). Numerous allelic variations (variants), captured in SNPs, of gene s are known in the art and catalogued (for example, in the National Center for Biotechnology Information "Entrez SNP"). Allelic variations that are not SNPs include deletions or insertions or substitutions of multiple consecutive nucleotides.

In non-limiting embodiments of the invention, the presence of an allelic variation, for example a SNP, may be determined using a technique such as, but not limited to, primer extension or polymerase chain reaction, using primer(s) designed based on sequence in the proximity of the variation, followed by sequencing. For example, and not by way of limitation, the presence of a SNP indicative of increased risk of ARONJ may be determined by a method comprising using at least one primer sequence complementary to a sequence flanking the location of the SNP (for example, within 80 nucleotides, or within 50 nucleotides, or within 30 nucleotides, or within 20 nucleotides, or within 10 nucleotides, of the SNP) in a primer extension reaction or polymerase chain reaction to generate a test fragment that contains the location of the SNP and determining the nucleotide present at the location of the single nucleotide polymorphism, for example by sequencing all or a portion of the test fragment.

A subject may be a human or a non-human subject. In a specific non-limiting embodiment, the subject suffers from osteoporosis. In a specific non-limiting embodiment, the subject is a postmenopausal woman. In a specific non-limiting embodiment, the subject has a cancer and has or is at risk for bone metastasis. In a specific non-limiting embodiment the subject has hypercalcemia.

To assess whether the subject carries a ARONJ biomarker as described herein, a sample of nucleic acid from the subject may be used. The nucleic acid may be genomic DNA or RNA reflective of the allelic variation or a cDNA copy thereof. For example, a sample comprising a cell from the subject may be collected. For example, the sample may be a tissue or body fluid, including but not limited to saliva, blood or its components, skin, hair follicle, urine, etc. The sample may be obtained by scraping the inside of the subject's mouth or cervix (eg in the context of a Pap smear). In a non-limiting example, as part of the detection process, nucleic acid may be at least partially purified from the sample.

5.1 Biomarker Genes and SNPS

In various non-limiting embodiments, the following genes and SNPs have been related to ARONJ, such that these genes and SNPs may be used as biomarkers for increased risk of ARONJ. Allelic variation and SNP variants may be used as indicators that a subject is at increased risk for ARONJ. The genes listed below, SNPs associated with those genes, and the further SNPs listed below are collectively referred to herein as "ARONJ biomarkers".

5.1.1 RBMS3

RBMS3 is an RNA-binding protein that belongs to the c-myc gene single-strand binding protein family. Its transcripts are alternatively spliced to form different mRNAs. In humans it is located at about positions 29322803-30051886 on chromosome 3 (NCBI Reference Sequence NC_00003.11).

In one non-limiting embodiment of the present invention, an allelic variation in the RBMS3 gene, where the allelic variation may be a SNP, is an indicator that a subject is at increased risk for developing ARONJ.

In another non-limiting embodiment of the present invention, an allelic variation in a region of RBMS3 from about positions 29900000 to 29990000 of the human gene on chromosome 3 (see NC_000003.11), where the allelic variation may be a SNP, is an indicator that a subject is at increased risk for developing ARONJ.

In another non-limiting embodiment of the present invention, an allelic variation in the intron of RBMS3 from about positions 29941247 to 29977576 of the human gene on chromosome 3, where the allelic variation may be a SNP, is an indicator that a subject is at increased risk for developing ARONJ. The sequence of this intron is set forth in FIG. 11.

In another non-limiting embodiment of the present invention, an allelic variation in a region of the intron of RBMS3 from about positions 29941247 to 29977576 of the human gene on chromosome 3, said region being between about 29954000 to 29955000 (between about nucleotides numbered 631198 and 632198 in FIG. 11), where the allelic variation may be a SNP, is an indicator that a subject is at increased risk for developing ARONJ.

In another non-limiting embodiment of the present invention, an allelic variant which is a SNP of RBMS3 selected from those set forth in TABLE 1 is an indicator that a subject is at increased risk for developing ARONJ. For clarity, the SNP is shown in bold text and underlined; for example, in rs17024608 the SNP is a substitution of ancestral nucleotide A by G, as shown by "A/G".

TABLE 1

| SEQ ID No. | SNP ref no. | Chr 3 position | Variation (bold, underlined) |
|---|---|---|---|
| 1 | rs17024608 | 29954690 | GATAGAATAGAACTATTTGATGTGGA/GCCATGAG AATTTAAAAGTATCTGCA |
| 2 | rs3821577 | 29910544 | AAGGCAGACGTATGGTGCCATGATGAA/GATTGGGTCCCA TGGAACACCCAATG |
| 3 | rs9820707 | 29954837 | TGAGAAATGACAGAAAAACTATATCAT/CCAGCAGAGAA AACATCTTCTTGCTG |
| 4 | rs9875937 | 29954551 | ATTGAGGGCAGGCATAAGACCTCTTGG/TCTATCATCACT AGGTGGCTCATAAA |
| 5 | rs9876178 | 29954887 | TGACCTAGGAAGGCATACAAATAGTTC/AAGTTGGCGTCA CACTGTTTATGCAT |
| 6 | rs13319154 | 29954187 | ACTTTCAATTTTCTGAAGAAATGTATA/TGGGCAACTACAT TAATATTCTTCAG |
| 7 | rs13326291 | 29954399 | CTCATGGAAAAGATGGCAAGATTGTTT/CAGTTTGTGCCA GAATTTTCCTTAAT |
| 8 | rs75830538 | 29954957 | GTGGTACTTGTTCCCTTTTATATCACT/CTAACATAAGTAT AATTTCATTGCAC |
| 9 | rs114730671 | 29954785 | TCTATCTTACAATAATTACTCAATATG/TTTCAGCAGACTC TGAAATCTGCACT |
| 10 | rs116600197 | 29954066 | TCAGCTGAAACAACTGTGTTATTCAGC/TGTAGTGTCTTAA TTGGCAGTTACAT |
| 11 | rs116863073 | 29954716 | ACCATGAGAATTTAAAAGTATCTGCAT/CAAATTGATGAT TTGGCATCAGATAA |
| 12 | rs118013282 | 29954445 | CTTAATAAATGTCTTCAAAGCTCTCAC/TAGGAGCCCAAG CATGTACACAGTTG |

In another non-limiting embodiment of the present invention, an allelic variant which is a SNP of RBMS3 as occurs in rs17024608, shown in TABLE 1, is an indicator that a subject is at increased risk for developing ARONJ.

In another non-limiting embodiment of the present invention, an allelic variant which is a substitution of A by G at position 29954690 of chromosome 3 is an indicator that a subject is at increased risk for developing ARONJ.

In another non-limiting embodiment of the present invention, an allelic variant which is a substitution of A by G in SEQ ID NO: 1: (GATAGAATAGAACTATTTGATGTGGA/GCCATGAGAATTTAAAAGTATCTGCA) at the position indicated by A/G, is an indicator that a subject is at increased risk for developing ARONJ.

In another non-limiting embodiment of the present invention, an allelic variant which is a SNP of RBMS3 selected from those set forth in TABLE 2 is an indicator that a subject is at increased risk for developing ARONJ.

mosome 4 (see NC_000004.11), where the allelic variation may be a SNP, is an indicator that a subject is at increased risk for developing ARONJ.

In another non-limiting embodiment of the present invention, an allelic variation in a region of IGFBP7 from about positions 57940000 to 57950000 of the human gene on chromosome 4 (see NC_000004.11), where the allelic variation may be a SNP, is an indicator that a subject is at increased risk for developing ARONJ.

In another non-limiting embodiment of the present invention, an allelic variation which is a SNP of IGFBP7 as occurs in rs11934877 is an indicator that a subject is at increased risk for developing ARONJ. The SNP of rs11934877 is located at position 57941026 of chromosome 4, where the ancestral nucleotide T is replaced by C, for example as in SEQ ID NO:19

TABLE 2

| SEQ ID NO. | SNP ref no. | Chr 3 position | Variation |
|---|---|---|---|
| 13 | rs10510628 | 29853403 | GCTCTGCCGTTTCTTAGGAAGTTGTGG/AAAGATATTGGTCTTTTTGTGAATAT |
| 14 | rs4599260 | 29853269 | CCATTAGGATAAAGAT/CGAGTGACCTCAAAAA |
| 15 | rs10514681 | 29853882 | TAGTGGGAAAGTTTTAAAGAGACCGTC/TATTGAGTGCTTTGATATGTTTGTTC |
| 16 | rs35393422 | 29853420 | GAAGTTGTGGAAGATATTGGTCTTTTT/-GTGAATATGTATGACACTATTCATT |
| 17 | rs79049188 | 29853041 | CTCTCATGGAGTCTACATTCTAAGGTC/TTCATAGGAAACACATGTAACTTTAC |
| 18 | rs115136555 | 29853407 | TGCCGTTTCTTAGGAAGTTGTGGAAGA/GTATTGGTCTTTTTGTGAATATGTAT |

5.1.2 IGF1R

The IGF1R gene in humans is located at about positions 99145510 to 99555008 on chromosome 15 (NCBI Reference Sequence NG_009492).

In one non-limiting embodiment of the present invention, an allelic variation in the IGF1R gene, where the allelic variation may be a SNP, is an indicator that a subject is at increased risk for developing ARONJ.

5.1.3 IGFBP7

The IGFBP7 gene in humans is located at about positions 57897244 to 57976539 on chromosome 4 (NCBI Reference Sequence NC_000004.11).

In one non-limiting embodiment of the present invention, an allelic variation in the IGFBP7 gene, where the allelic variation may be a SNP, is an indicator that a subject is at increased risk for developing ARONJ.

In another non-limiting embodiment of the present invention, an allelic variation in a region of IGFBP7 from about positions 57920000 to 57950000 of the human gene on chromosome 4 (see NC_000004.11), where the allelic variation may be a SNP, is an indicator that a subject is at increased risk for developing ARONJ.

In another non-limiting embodiment of the present invention, an allelic variation in a region of IGFBP7 from about positions 57930000 to 57940000 of the human gene on chromosome 4 (see NC_000004.11), where the allelic variation may be a SNP, is an indicator that a subject is at increased risk for developing ARONJ.

TAATCTGTGTTAAAACAATATAGCATT/CATCTGCTTTGAATGCACTAGGCACC.

In another non-limiting embodiment of the present invention, an allelic variation which is a SNP of IGFBP7 as occurs in rs17761305 is an indicator that a subject is at increased risk for developing ARONJ. The SNP of rs17761305 is located at position 57934091 of chromosome 4, where the ancestral nucleotide C is replaced by T, for example as in SEQ ID NO 20:

CCCCTGGAGAATAATTGATAGGGTAGC/TGAAAAATGTGGATATCATAAAATAT.

5.1.4 DPYD

The DPYD gene in humans is located at about positions (−)98513111 to (−) 97416801 on the negative strand of chromosome 1 (NCBI Reference Sequence NG_008807.1)

In one non-limiting embodiment of the present invention, an allelic variation in the DPYD gene, where the allelic variation may be a SNP, is an indicator that a subject is at increased risk for developing ARONJ.

In another non-limiting embodiment of the present invention, an allelic variation in a region of DPYD gene from about positions (−)97800000 to (−)97500000 of the human gene on chromosome 1 (see NG_008807.1), where the allelic variation may be a SNP, is an indicator that a subject is at increased risk for developing ARONJ.

In another non-limiting embodiment of the present invention, an allelic variation in a region of DPYD gene from about positions (−)97700000 to (−)97650000 of the human gene on chromosome 1 (see NG_008807.1), where the allelic variation may be a SNP, is an indicator that a subject is at increased risk for developing ARONJ.

In another non-limiting embodiment of the present invention, an allelic variation which is a SNP of DPYD as occurs in rs10875055 is an indicator that a subject is at increased risk for developing ARONJ. The SNP of rs10875055 is located at position (−)97683997 of chromosome 1, where the ancestral nucleotide C is replaced by T, for example as in SEQ ID NO:21:

TTCATCTCACTAATAAGAGCTACCCA<u>C/T</u>CCGCCTTTATACAGAGGTT

CTCAGA

5.1.5 ABCC4

The ABCC4 gene in humans is located at about positions 95672083-95953687 on chromosome 13 (NCBI Reference Sequence NC_000013.10).

In one non-limiting embodiment of the present invention, an allelic variation in the ABCC4 gene, where the allelic variation may be a SNP, is an indicator that a subject is at increased risk for developing ARONJ.

In another non-limiting embodiment of the present invention, an allelic variation in a region of ABCC4 gene from about positions 95730000 to 95740000 of the human gene on chromosome 13 (see NC_000013.10), where the allelic variation may be a SNP, is an indicator that a subject is at increased risk for developing ARONJ.

In another non-limiting embodiment of the present invention, an allelic variation in a region of ABCC4 gene from about positions 95732000 to 95738000 of the human gene on chromosome 13 (see NC_000013.10), where the allelic variation may be a SNP, is an indicator that a subject is at increased risk for developing ARONJ.

In another non-limiting embodiment of the present invention, an allelic variation which is a SNP of ABCC4 as occurs in rs1189437 is an indicator that a subject is at increased risk for developing ARONJ. The SNP of rs1189437 is located at position 95735604 of chromosome 13, where the ancestral nucleotide A is replaced by C, for example as in SEQ ID NO:22:

GAGTGTAATCCTAACAACAACTCATG<u>A/C</u>AAGTATTTTTGAAAAGAA

TACTTGA.

5.1.6 GSTM2

The GSTM2 gene in humans is located at about positions 110210644 to 110226619 on chromosome 1 (NCBI Reference Sequence NC_000001.10).

In one non-limiting embodiment of the present invention, an allelic variation in the GSTM2 gene, where the allelic variation may be a SNP, is an indicator that a subject is at increased risk for developing ARONJ.

In another non-limiting embodiment of the present invention, an allelic variation in a region of GSTM2 gene from about positions 110210000 to 110215000 of the human gene on chromosome 3 (see NC_000001.10), where the allelic variation may be a SNP, is an indicator that a subject is at increased risk for developing ARONJ.

In another non-limiting embodiment of the present invention, an allelic variation which is a SNP of GSTM2 as occurs in rs673151 is an indicator that a subject is at increased risk for developing ARONJ. The SNP of rs673151 is located at position 110213458 of chromosome 1, where the ancestral nucleotide G is replaced by A, for example as in SEQ ID NO:23:

GAAAGATGAGGAGATATTCAGAGGAT<u>G/A</u>AGTGGAAGAAAGGAGGG

GGAAAAAG.

5.1.7 Further SNP Biomarkers

In further non-limiting embodiments of the present invention, the presence of an allelic variation which is a SNP selected from those set forth in TABLE 3 is an indicator that a subject is at increased risk for developing ARONJ.

TABLE 3

| SEQ ID NO. | SNP ref no. | Chromosome location/ gene | Variation |
|---|---|---|---|
| 24 | rs8012823 | 72343297chr14 DPF3 gene | CTGGAGGGCTTCCAA<u>T/C</u>GGACTGATCTCTTTG |
| 25 | rs11802277 | Chr. 1 | GAGAGTGAGAACTGAGTGGGCTGGGGAGCT<u>G/T</u>ATGGACTTTACCCTGCCATTTCCTAACCC |
| 26 | rs10754178 | 196416252chr 1 KCNT2 | TTCTTTCCATCTTCA<u>A/G</u>TGAAATATTTTGCCT |
| 27 | rs13096022 | 7425350 chr3 GRM7 | TCAGG<u>A/G</u>TTAAC |
| 28 | rs6900513 | 66333105chr6 EYS | GATAACCTCCAAAGA<u>C/T</u>TTGGTTGTAATTTTC |
| 29 | rs1873291 | 66344855chr6 EYS | TTAAAAATCAATTTG<u>C/T</u>CTTCATCACAGACAG |

TABLE 3-continued

| SEQ ID NO. | SNP ref no. | Chromosome location/ gene | Variation |
|---|---|---|---|
| 30 | rs10781262 | 77650696chr9 | TTAATAAAGGGTAAGATTGGGCTATCA/GTATTTGAATT AGCAGAATCACTCTA |
| 31 | rs1471646 | chr 1 RP11-382E9.1 | GACTCATCTGACTTAGAAATGGGTGG[A/G]TGAAAAG AATCTTCACTCACTATGT |
| 32 | rs4870310 | chr 6 RP11-15G8.1 | ancestral gene nucleotide is T; variant is C CTCGTTGTTTTTCTGGCACTACAAGAT/CGTTCCAGGTTC ATCTTATATATTCT |
| 33 | rs10875148 | 98859508chr1 | ancestral gene nucleotide is G; variant is A TATTTTCTAACTCTTTCTGGTATAATG/AGGAACAGTCAA GATCTGAACAAGAG |
| 34 | rs4562759 | 83835639chr10 NRG3 | ancestral gene nucleotide is T; variant is C AGAGAGTAGAATTAAGTGGTTTTTCAT/CGGAATTATG GAGGGAGAATGAAAT |
| 35 | rs4878512 | 27630418chr9 RP11-53S18.1 | ancestral gene nucleotide is A; variant is G AAGAATGTAAAGCATTCTCTAGTCCTA/GTTTCCTTTCCT TGTTTGTTTTCTCT |
| 36 | rs12613966 | AC113618.1 | ancestral gene nucleotide is C; variant is T AAATGTCACCTTTGAGTAGTGAAGTTC/TGGATGATTTT TATTTTCTTATTTT |
| 37 | rs11189381 | RP11-459F3.3 | ancestral gene nucleotide is T, variant is C GCTGGCTTCTTCTTAATCAGAACTGCT/CCTTAGCTTCAA GAGAGGCTGGAAAA |
| 38 | rs6861122 | AC022120.1 | ancestral gene nucleotide is C; variant is T TTAGTAATATGCCTTTAAGGTACCTCC/TATCTAAACTGA ACATGCTCATTA |
| 39 | rs4431170 | MARCH1 | ancestral gene nucleotide is A; variant is G TGAAACCAAACTATAAACTACTTCTTA/GTCTTTGTGAGA GAATTCCAGGGCAC |

In another non-limiting embodiment of the present invention, an allelic variant which is a SNP of the human EYS gene in a region on chromosome 6 between 66325000 and 66350000, where the allelic variation may be a SNP, is an indicator that a subject is at increased risk for developing ARONJ.

In further non-limiting embodiments of the present invention, an allelic variation which is a SNP selected from those set forth in TABLE 4 is an indicator that a subject is at increased risk for developing ARONJ, where the nucleotide in the column marked "allele" is the allele indicative of the increased risk (among the SNPs listed in TABLE 4, sometimes the allele associated with ARONJ is the variant allele, and sometimes it is the allele found in the majority of the population tested). The SNPs listed in TABLE 4, except for rs17024608 which is discussed above, are denoted SNP ID #40-147. Commercial probes or sequences corresponding to the SNPs listed in TABLE 4 are publicly available, either for the SNP named (e.g. "rs17024608") or at the chromosomal position specified (e.g., "12-85466404" denotes a SNP found at position 85466404 on human chromosome 12). For convenience, and not by way of limitation, the sequences of certain regions containing SNPs are set forth in TABLE 5 below as SEQ ID NOS: 40-85.

TABLE 4

| CHR | SNP | LOCATION | ALLELE | TESTED | SA\|OR | SE | L95 | U95 | STAT | P. value | SNP ID# |
|---|---|---|---|---|---|---|---|---|---|---|---|
| 3 | rs17024608 | 29954690 | G | 1744 | 5.825 | 0.3276 | 3.065 | 11.07 | 5.379 | 7.47E−08 | |
| 22 | rs5768434 | 46977516 | T | 1752 | 12.61 | 0.4784 | 4.937 | 32.2 | 5.298 | 1.17E−07 | 40 |
| 12 | rs11064477 | 6944626 | A | 1689 | 21.66 | 0.6126 | 6.52 | 71.98 | 5.02 | 5.16E−07 | 41 |
| 12 | 12-85466404 | 85466404 | A | 1696 | 9.296 | 0.4769 | 3.65 | 23.67 | 4.675 | 2.95E−06 | 42 |
| 8 | 8-58133986 | 58133986 | T | 1746 | 7.326 | 0.427 | 3.173 | 16.92 | 4.664 | 3.10E−06 | 43 |
| 1 | rs1886629 | 194421521 | C | 1755 | 3.698 | 0.2878 | 2.104 | 6.501 | 4.544 | 5.53E−06 | 44 |
| 2 | rs7588295 | 166115757 | G | 1716 | 8.681 | 0.4783 | 3.399 | 22.17 | 4.518 | 6.24E−06 | 45 |
| 4 | rs4431170 | 165504024 | G | 1748 | 5.176 | 0.3665 | 2.523 | 10.62 | 4.485 | 7.28E−06 | 46 |
| 6 | rs7740004 | 120897902 | A | 1757 | 5.952 | 0.3992 | 2.722 | 13.02 | 4.469 | 7.87E−06 | 47 |
| 10 | rs11189381 | 99553188 | C | 1728 | 6.816 | 0.4303 | 2.933 | 15.84 | 4.461 | 8.17E−06 | 48 |
| 15 | rs12903202 | 56094085 | G | 1690 | 4.036 | 0.3145 | 2.179 | 7.477 | 4.436 | 9.15E−06 | 49 |
| 18 | rs17751934 | 47455812 | T | 1773 | 5.009 | 0.3632 | 2.458 | 10.21 | 4.436 | 9.16E−06 | 50 |
| 11 | 11-23990403 | 23990403 | C | 1708 | 12.17 | 0.5655 | 4.016 | 36.86 | 4.419 | 9.94E−06 | 51 |
| 3 | rs7613687 | 60124976 | T | 1733 | 13.44 | 0.6107 | 4.061 | 44.49 | 4.255 | 2.09E−05 | 52 |
| 3 | rs7634338 | 8864809 | C | 1708 | 12.55 | 0.6001 | 3.87 | 40.68 | 4.215 | 2.50E−05 | 53 |
| 3 | rs7612449 | 181586884 | T | 1718 | 11.79 | 0.5708 | 3.853 | 36.1 | 4.323 | 1.54E−05 | 54 |

TABLE 4-continued

| CHR | SNP | LOCATION | ALLELE | TESTED | SA\|OR | SE | L95 | U95 | STAT | P. value | SNP ID# |
|---|---|---|---|---|---|---|---|---|---|---|---|
| 4 | rs10029016 | 8496903 | A | 1685 | 11.73 | 0.5612 | 3.905 | 35.24 | 4.388 | 1.15E−05 | 55 |
| 12 | rs10505722 | 1102632 | G | 1716 | 11.39 | 0.5651 | 3.763 | 34.48 | 4.305 | 1.67E−05 | 56 |
| 14 | rs2332834 | 71952831 | C | 1690 | 11.3 | 0.6162 | 3.378 | 37.82 | 3.935 | 8.31E−05 | 57 |
| 7 | rs10271074 | 78589212 | G | 1713 | 11.08 | 0.557 | 3.719 | 33.02 | 4.318 | 1.57E−05 | 58 |
| 3 | 3-85058749 | 85058749 | A | 1729 | 10.99 | 0.6046 | 3.36 | 35.95 | 3.965 | 7.35E−05 | 59 |
| 5 | 5-159725177 | 159725177 | C | 1744 | 10.91 | 0.5466 | 3.736 | 31.84 | 4.371 | 1.24E−05 | 60 |
| 1 | rs4951362 | 202580842 | C | 1719 | 10.66 | 0.5452 | 3.662 | 31.04 | 4.341 | 1.42E−05 | 61 |
| 2 | rs62153910 | 96382119 | T | 1766 | 10.46 | 0.5396 | 3.632 | 30.11 | 4.35 | 1.36E−05 | 62 |
| 1 | 1-55273566 | 55273566 | G | 1740 | 10.37 | 0.5975 | 3.216 | 33.46 | 3.915 | 9.05E−05 | 63 |
| 2 | 2-15831165 | 15831165 | A | 1726 | 10.33 | 0.5364 | 3.609 | 29.55 | 4.352 | 1.35E−05 | 64 |
| 2 | 2-53263505 | 53263505 | C | 1722 | 10.03 | 0.5434 | 3.456 | 29.09 | 4.242 | 2.22E−05 | 65 |
| 2 | rs4062819 | 95777963 | A | 1730 | 9.872 | 0.5353 | 3.457 | 28.19 | 4.277 | 1.89E−05 | 66 |
| 7 | 7-13058926 | 13058926 | T | 1696 | 9.791 | 0.528 | 3.479 | 27.56 | 4.321 | 1.55E−05 | 67 |
| 15 | rs7176436 | 56752223 | G | 1731 | 9.767 | 0.5365 | 3.413 | 27.95 | 4.248 | 2.16E−05 | 68 |
| 2 | 2-95978053 | 95978053 | A | 1731 | 9.685 | 0.5337 | 3.403 | 27.57 | 4.254 | 2.10E−05 | 69 |
| 1 | rs17127107 | 65099496 | G | 1685 | 9.492 | 0.5126 | 3.476 | 25.92 | 4.391 | 1.13E−05 | 70 |
| 7 | 7-78589823 | 78589823 | A | 1717 | 9.426 | 0.5521 | 3.194 | 27.82 | 4.063 | 4.84E−05 | 71 |
| 2 | rs62156621 | 79426168 | A | 1727 | 9.31 | 0.524 | 3.334 | 26 | 4.258 | 2.06E−05 | 72 |
| 2 | rs921245 | 137980811 | C | 1720 | 9.295 | 0.5267 | 3.311 | 26.09 | 4.233 | 2.30E−05 | 73 |
| 12 | 12-85423495 | 85423495 | C | 1701 | 9.284 | 0.5088 | 3.425 | 25.17 | 4.379 | 1.19E−05 | 74 |
| 12 | 12-85114303 | 85114303 | C | 1742 | 9.104 | 0.5056 | 3.379 | 24.53 | 4.368 | 1.25E−05 | 75 |
| 9 | 9-29422005 | 29422005 | T | 1739 | 9.06 | 0.5455 | 3.111 | 26.39 | 4.04 | 5.34E−05 | 76 |
| 1 | rs1736563 | 169371174 | A | 1691 | 8.941 | 0.5421 | 3.09 | 25.87 | 4.041 | 5.32E−05 | 77 |
| 5 | 5-65503171 | 65503171 | A | 1765 | 8.934 | 0.5453 | 3.068 | 26.02 | 4.016 | 5.93E−05 | 78 |
| 7 | 7-78597753 | 78597753 | G | 1721 | 8.788 | 0.5503 | 2.989 | 25.84 | 3.949 | 7.83E−05 | 79 |
| 10 | 10-94242917 | 94242917 | G | 1743 | 8.785 | 0.5164 | 3.193 | 24.17 | 4.208 | 2.58E−05 | 80 |
| 10 | 10-94239487 | 94239487 | G | 1743 | 8.779 | 0.5164 | 3.191 | 24.15 | 4.207 | 2.59E−05 | 81 |
| 10 | 10-94264341 | 94264341 | A | 1739 | 8.758 | 0.5164 | 3.183 | 24.1 | 4.202 | 2.65E−05 | 82 |
| 2 | 2-15818709 | 15818709 | A | 1728 | 8.724 | 0.5391 | 3.033 | 25.1 | 4.018 | 5.87E−05 | 83 |
| 12 | 12-85440122 | 85440122 | G | 1702 | 8.663 | 0.5067 | 3.209 | 23.39 | 4.261 | 2.04E−05 | 84 |
| 12 | rs4639998 | 85442168 | T | 1702 | 8.663 | 0.5067 | 3.209 | 23.39 | 4.261 | 2.04E−05 | 85 |
| 4 | rs7669796 | 160863851 | G | 1716 | 8.662 | 0.5458 | 2.972 | 25.25 | 3.955 | 7.64E−05 | 86 |
| 12 | rs17653326 | 85528244 | A | 1748 | 8.661 | 0.5037 | 3.227 | 23.24 | 4.286 | 1.82E−05 | 87 |
| 9 | rs17057133 | 73509497 | C | 1692 | 8.616 | 0.5078 | 3.184 | 23.31 | 4.241 | 2.23E−05 | 88 |
| 16 | rs3135009 | 12556820 | T | 1721 | 8.608 | 0.5224 | 3.092 | 23.96 | 4.121 | 3.78E−05 | 89 |
| 2 | 2-15819709 | 15819709 | C | 1729 | 8.597 | 0.539 | 2.989 | 24.73 | 3.991 | 6.57E−05 | 90 |
| 2 | rs2544530 | 15820699 | G | 1728 | 8.569 | 0.5392 | 2.978 | 24.65 | 3.984 | 6.77E−05 | 91 |
| 8 | rs16915413 | 94070482 | A | 1730 | 8.569 | 0.5422 | 2.961 | 24.8 | 3.962 | 9.30E+01 | 92 |
| 10 | 10-59772956 | 59772956 | T | 1735 | 8.567 | 0.5454 | 2.942 | 24.95 | 3.938 | 8.21E−05 | 93 |
| 9 | 9-17649682 | 17649682 | G | 1743 | 8.399 | 0.5149 | 3.062 | 23.04 | 4.133 | 3.58E−05 | 94 |
| 9 | 9-17652481 | 17652481 | T | 1742 | 8.394 | 0.5149 | 3.06 | 23.03 | 4.132 | 3.60E−05 | 95 |
| 3 | 3-85899151 | 85899151 | T | 1739 | 8.389 | 0.5348 | 2.941 | 23.93 | 3.977 | 6.98E−05 | 96 |
| 12 | 12-39900069 | 39900069 | A | 1696 | 8.387 | 0.5327 | 2.952 | 23.83 | 3.992 | 6.55E−05 | 97 |
| 16 | rs2856790 | 12557384 | C | 1726 | 8.375 | 0.5203 | 3.02 | 23.22 | 4.084 | 4.42E−05 | 98 |
| 12 | 12-85389759 | 85389759 | G | 1768 | 8.369 | 0.5024 | 3.126 | 22.4 | 4.228 | 2.35E−05 | 99 |
| 3 | 3-29881391 | 29881391 | C | 1745 | 8.209 | 0.4884 | 3.152 | 21.38 | 4.31 | 1.63E−05 | 100 |
| 3 | 3-29881550 | 29881550 | G | 1745 | 8.207 | 0.4884 | 3.151 | 21.37 | 4.31 | 1.63E−05 | 101 |
| 3 | rs6443519 | 179112920 | A | 1723 | 8.199 | 0.5176 | 2.973 | 22.61 | 4.065 | 4.81E−05 | 102 |
| 2 | 2-79440423 | 79440423 | G | 1736 | 8.146 | 0.5165 | 2.96 | 22.42 | 4.061 | 4.89E−05 | 103 |
| 9 | 9-26597745 | 26597745 | A | 1692 | 8.107 | 0.4926 | 3.087 | 21.29 | 4.248 | 2.16E−05 | 104 |
| 10 | 10-55210159 | 55210159 | A | 1734 | 8.027 | 0.5261 | 2.862 | 22.51 | 3.959 | 7.54E−05 | 105 |
| 2 | rs7568908 | 79462538 | T | 1707 | 7.903 | 0.5117 | 2.876 | 21.72 | 4.008 | 6.11E−05 | 106 |
| 7 | 7-54640120 | 54640120 | T | 1753 | 7.771 | 0.4985 | 2.925 | 20.64 | 4.113 | 3.90E−05 | 107 |
| 7 | 7-54633747 | 54633747 | G | 1752 | 7.766 | 0.4984 | 2.924 | 20.63 | 4.112 | 3.92E−05 | 108 |
| 7 | 7-54635902 | 54635902 | A | 1752 | 7.766 | 0.4984 | 2.924 | 20.63 | 4.112 | 3.92E−05 | 109 |
| 7 | 7-54638869 | 54638869 | G | 1752 | 7.766 | 0.4984 | 2.924 | 20.63 | 4.112 | 3.92E−05 | 110 |
| 7 | 7-54638903 | 54638903 | G | 1752 | 7.766 | 0.4984 | 2.924 | 20.63 | 4.112 | 3.92E−05 | 111 |
| 2 | rs2544538 | 15825910 | A | 1737 | 7.707 | 0.5184 | 2.79 | 21.29 | 3.939 | 8.19E−05 | 112 |
| 8 | 8-58130916 | 58130916 | A | 1732 | 7.601 | 0.4593 | 3.09 | 18.7 | 4.416 | 1.01E−05 | 113 |
| 2 | 2-15828311 | 15828311 | A | 1738 | 7.563 | 0.5184 | 2.738 | 20.89 | 3.903 | 9.51E−05 | 114 |
| 19 | 19-55065301 | 55065301 | C | 1732 | 7.557 | 0.5053 | 2.807 | 20.34 | 4.003 | 6.26E−05 | 115 |
| 2 | 2-21318018 | 21318018 | A | 1728 | 7.553 | 0.4896 | 2.893 | 19.72 | 4.13 | 3.63E−05 | 116 |
| 2 | 2-15838147 | 15838147 | G | 1716 | 7.549 | 0.5177 | 2.737 | 20.82 | 3.905 | 9.43E−05 | 117 |
| 20 | 20-55029650 | 55029650 | C | 1702 | 7.534 | 0.4877 | 2.897 | 19.6 | 4.141 | 3.46E−05 | 118 |
| 20 | 20-55029675 | 55029675 | C | 1702 | 7.534 | 0.4877 | 2.897 | 19.6 | 4.141 | 3.46E−05 | 119 |
| 2 | rs57446887 | 21316772 | C | 1725 | 7.528 | 0.4896 | 2.884 | 19.65 | 4.123 | 3.74E−05 | 120 |
| 2 | rs10203465 | 81260623 | C | 1748 | 7.519 | 0.4849 | 2.907 | 19.45 | 4.161 | 3.17E−05 | 121 |
| 2 | 2-15840134 | 15840134 | C | 1709 | 7.507 | 0.5177 | 2.722 | 20.71 | 3.894 | 9.86E−05 | 122 |
| 14 | 14-98055995 | 98055995 | A | 1742 | 7.502 | 0.4786 | 2.936 | 19.17 | 4.211 | 2.55E−05 | 123 |
| 14 | 14-98056427 | 98056427 | C | 1742 | 7.502 | 0.4786 | 2.936 | 19.17 | 4.211 | 2.55E−05 | 124 |
| 1 | rs2805873 | 57713578 | A | 1713 | 7.499 | 0.4683 | 2.995 | 18.78 | 4.302 | 1.69E−05 | 125 |
| 2 | 2-15833678 | 15833678 | G | 1724 | 7.499 | 0.5177 | 2.718 | 20.69 | 3.891 | 9.96E−05 | 126 |
| 7 | 7-54624309 | 54624309 | G | 1754 | 7.487 | 0.4964 | 2.83 | 19.81 | 4.056 | 5.00E−05 | 127 |
| 7 | rs11982678 | 54625449 | A | 1754 | 7.487 | 0.4964 | 2.83 | 19.81 | 4.056 | 5.00E−05 | 128 |
| 2 | 2-21321893 | 21321893 | A | 1729 | 7.413 | 0.4883 | 2.847 | 19.3 | 4.102 | 4.09E−05 | 129 |
| 2 | rs7602629 | 21323199 | A | 1729 | 7.413 | 0.4883 | 2.847 | 19.3 | 4.102 | 4.09E−05 | 130 |
| 14 | 14-98042176 | 98042176 | G | 1743 | 7.407 | 0.4779 | 2.903 | 18.9 | 4.19 | 2.79E−05 | 131 |
| 3 | rs12636997 | 29874808 | G | 1712 | 7.351 | 0.5042 | 2.737 | 19.75 | 3.957 | 7.60E−05 | 132 |

TABLE 4-continued

| CHR | SNP | LOCATION | ALLELE | TESTED | SA\|OR | SE | L95 | U95 | STAT | P. value | SNP ID# |
|---|---|---|---|---|---|---|---|---|---|---|---|
| 14 | rs12431810 | 98044037 | A | 1744 | 7.33 | 0.4777 | 2.874 | 18.7 | 4.17 | 3.05E−05 | 133 |
| 8 | 8-91414191 | 91414191 | A | 1707 | 7.312 | 0.4836 | 2.834 | 18.86 | 4.114 | 3.88E−05 | 134 |
| 2 | rs312047 | 21328107 | A | 1686 | 7.236 | 0.4866 | 2.788 | 18.78 | 4.067 | 4.76E−05 | 135 |
| 20 | rs2297429 | 61699516 | T | 1726 | 7.208 | 0.506 | 2.673 | 19.43 | 3.903 | 9.49E−05 | 136 |
| 3 | 3-29883350 | 29883350 | A | 1751 | 7.182 | 0.4669 | 2.876 | 17.93 | 4.222 | 2.42E−05 | 137 |
| 2 | 2-81311658 | 81311658 | C | 1750 | 7.18 | 0.4836 | 2.783 | 18.52 | 4.077 | 4.57E−05 | 138 |
| 3 | rs12638932 | 29882677 | T | 1749 | 7.171 | 0.4669 | 2.872 | 17.91 | 4.219 | 2.45E−05 | 139 |
| 3 | 3-29881826 | 29881826 | C | 1748 | 7.166 | 0.4669 | 2.87 | 17.89 | 4.218 | 2.47E−05 | 140 |
| 2 | rs1986414 | 201199695 | A | 1711 | 7.164 | 0.4573 | 2.924 | 17.56 | 4.306 | 1.66E−05 | 141 |
| 3 | 3-29884382 | 29884382 | C | 1758 | 7.126 | 0.4674 | 2.851 | 17.81 | 4.202 | 2.65E−05 | 142 |
| 2 | rs2219366 | 81318138 | A | 1748 | 7.118 | 0.4834 | 2.76 | 18.36 | 4.06 | 4.90E−05 | 143 |
| 19 | 19-55069295 | 55069295 | C | 1732 | 7.111 | 0.5022 | 2.658 | 19.03 | 3.906 | 9.37E−05 | 144 |
| 9 | 9-17634306 | 17634306 | T | 1755 | 7.102 | 0.5027 | 2.651 | 19.02 | 3.9 | 9.63E−05 | 145 |
| 10 | rs1886951 | 2425384 | A | 1686 | 7.085 | 0.456 | 2.899 | 17.32 | 4.294 | 1.75E−05 | 146 |
| 19 | 19-55072907 | 55072907 | T | 1735 | 7.054 | 0.502 | 2.637 | 18.87 | 3.892 | 9.95E−05 | 147 |

TABLE 5

| CHR | SNP | LOCATION | AL-LELE | SNP ID# | SEQ ID NO: | Sequence |
|---|---|---|---|---|---|---|
| 22 | rs5768434 | 46977516 | T | 40 | 40 | TTTGTATCTAATGTTTATATTctttta[C/T]gcttgaaactatttgaagcattcta |
| 12 | rs11064477 | 6944626 | A | 41 | 41 | AGCCTTCCCAGCTTGGGTCCTGTTTC[A/G]GAGCCCAGGCCTTGCTTCCCCTTAG |
| 1 | rs1886629 | 194421521 | C | 44 | 42 | GAATCTCCAAGTTAATTTTTTCATTG[C/T]TTACCCTTTATTACTGCATGAAGTC |
| 2 | rs7588295 | 166115757 | G | 45 | 43 | ACTTTTTTTTTTCAATTCTGAAATCA[A/G]CTTCTTAGATCTACTTTTCCTTACC |
| 4 | rs4431170 | 165504024 | G | 46 | 44 | TGAAACCAAACTATAAACTACTTCTT[A/G]TCTTTGTGAGAGAATTCCAGGGCAC |
| 6 | rs7740004 | 120897902 | A | 47 | 45 | TACAACTCTCAAGAAGCAATCTTTTT[A/T]TGGCAGGAAGCTGCATGAGTGATAA |
| 10 | rs11189381 | 99553188 | C | 48 | 46 | GCTGGCTTCTTCTTAATCAGAACTGC[C/T]CTTAGCTTCAAGAGAGGCTGGAAAA |
| 15 | rs12903202 | 56094085 | G | 49 | 47 | CACTGATGCTAAGGCAAGAGTTATCG[A/G]TAGCCCAAGCTCTGGCTAGTATCCA |
| 18 | rs17751934 | 47455812 | T | 50 | 48 | ATAGAATAAATAAGGTAACAGGTAAT[C/T]TAAACAAAGAGAAAAATATCTATTT |
| 3 | rs7613687 | 60124976 | T | 52 | 49 | GGGAAATGAATCCCTGGCAGGATGGA[C/T]ATTAACCAAACACCTAACACATCAG |
| 3 | rs7634338 | 8864809 | C | 53 | 50 | GGGAATATATGGTATTAATGAAAGCA[C/T]TGCTACACCTAGGTACCCCATACCT |
| 3 | rs7612449 | 181586884 | T | 54 | 51 | TTAAGTTATTGCTATCCTATCCTTCT[C/T]CAAAGAGCTTTTCTTCTGTTTTTTA |
| 4 | rs10029016 | 8496903 | A | 55 | 52 | gtggaaggatggttaccagagggtgg[A/G]aaggggagtggagggttgggggaga |
| 12 | rs10505722 | 1102632 | G | 56 | 53 | AATGATAAGCTTAAGAAAATACAAGC[A/C/G/T]TAAGTATGGCTCTTAATACGCTAGA |
| 14 | rs2332834 | 71952831 | C | 57 | 54 | GTCTCCTTTTCTTCTTGTCCCCTGCT[C/T]TCAGCTCTGAATGAGAAAAGTTTTG |
| 7 | rs10271074 | 78589212 | G | 58 | 55 | TATAAAGTCATCCTACTTTCTCTTTC[A/G]TACTTTCAAAAGTTGGTATTCAGTA |
| 1 | rs4951362 | 202580842 | C | 61 | 56 | GGCGAGAAAGACATATGTGGATGGAA[C/T]ATTTCAGAACAACTTGTATTTCCAA |
| 2 | rs62153910 | 96382119 | T | 62 | 57 | CTACACTTGGGGTCCCAGAAGAGCTG[C/T]CCCCTCCTGCACATTTCCAATGCAG |
| 15 | rs7176436 | 56752223 | G | 68 | 58 | TTATGAAAAGGCTGTGAAGCTGAAGA[A/G]AAACTAAGAAATGGATATTGCTGCA |
| 1 | rs17127107 | 65099496 | G | 70 | 59 | GTGGTTCATCTCATAGCAGACTTGCT[C/T]TAGAAGGTGAAACTCCCGGATTTTA |
| 2 | rs62156621 | 79426168 | A | 72 | 60 | CACTCACACTTGTCCAGAGTTTCCTC[A/T]TGCTTTCTACTCTTCTGAAATCCTG |
| 2 | rs921245 | 137980811 | C | 73 | 61 | TAGCTTCCACAACATTCCCAGGCTAC[A/G]AGAGCTTACAGTCCATTAGCACTGA |
| 1 | rs1736563 | 169371174 | A | 77 | 62 | TTAAATCACAAATGCAGTCTCAATCC[A/G]GAAAATAGATCCCATCATATGTGAT |
| 12 | rs4639998 | 85442168 | T | 85 | 63 | tctttctcatatttatgtgcttcctt[C/T]aggagctctagtaaggcaggtctgg |
| 4 | rs7669796 | 160863851 | G | 86 | 64 | gccaagggggtgcctgcaggcccatgc[G/T]gagccaccctcagacctccttcagc |
| 12 | rs17653326 | 85528244 | A | 87 | 65 | AGGAGGATATATAACCCTGGCTTGAA[A/G]AAGATGGAGATAGCTACAAGAGATG |
| 9 | rs17057133 | 73509497 | C | 88 | 66 | GTTGGACGGATACTCATCTCGTGTAA[C/T]GGTCATAGAAAGATTCTGAGTGCTC |

TABLE 5-continued

| CHR | SNP | LOCATION | AL-LELE | SEQ ID NO# | SNP ID: Sequence |
|---|---|---|---|---|---|
| 16 | rs3135009 | 12556820 | T | 89 67 | CTCATGTACGCAGGGTGTTTCCCTAG[C/T]TGACATGTCTGAGGACGTCTTTCGT |
| 2 | rs2544530 | 15820699 | G | 91 68 | TTCCAAACCCGGCTTTCCCTCATTTG[A/G]TCCTCAAACACCCCATCGGGGGCC |
| 8 | rs16915413 | 94070482 | A | 92 69 | TAGCCATTGACAAACCCTGTAGACAT[A/G]AGAATTTAATATGTGATAAAGATAA |
| 16 | rs2856790 | 12557384 | C | 98 70 | CACTTGTCCTGTGGACTCATGCCATG[C/T]CACCGTAGTGCTGAGTGACGCTTAA |
| 3 | rs6443519 | 179112920 | A | 102 71 | ttcatgctaaaaactctgaataaact[A/C]ggtttttgatggaatgtatctcaaaa |
| 2 | rs7568908 | 79462538 | T | 106 72 | TAGCAATGCAAGCATGTTTGCCTTCA[G/T]ATAGCTAAATGACTGCgtgattgct |
| 2 | rs57446887 | 21316772 | C | 120 73 | TTATTCCTATGCTTGTTGGCTGCATG[C/T]ATGTCTTCTTTTGAAAAGTGTATCT |
| 2 | rs10203465 | 81260623 | C | 121 74 | tggtaataattacaagaaaaatgtct[C/G]tacatgttcagtataaatgcaacct |
| 1 | rs2805873 | 57713578 | A | 125 75 | TGGCTTCCTGGGTGCAACATCCGGAC[C/T]GATGTCTTTTATTGTTGTTATTGtt |
| 7 | rs11982678 | 54625449 | A | 128 76 | tatacacacacatataATTAATGCTA[A/G]AAGGCTATACACAGGAACACTATTG |
| 2 | rs7602629 | 21323199 | A | 130 77 | gaggcctcaggaagcttttactgatg[A/G]ctgtaggcaaagtgagagcaggcac |
| 3 | rs12636997 | 29874808 | G | 132 78 | AAAAAATTTCATCTTATATGTAGTAC[A/G]TAGTAATCTATAAATATAAAATACA |
| 14 | rs12431810 | 98044037 | A | 133 79 | ATGTTGAGATAGTAGCACAGGAGGCC[A/C]GGGATTTATTTGGGTTATACACAGA |
| 2 | rs312047 | 21328107 | A | 135 80 | AAGAGAGAATCAAAAGGCAGGTCCTC[A/G]CAGCAGGCGCTGGGACATCTGTATC |
| 20 | rs2297429 | 61699516 | T | 136 81 | ACAAGAAAGCAAGAGCTGCCAGGGCC[C/T]CTTCCAGCAGGGAGGCTGACCCTGC |
| 3 | rs12638932 | 29882677 | T | 139 82 | AAGCTTCTGactgttaagggtgatgg[A/T]tatgttcattatcttgacaatggtg |
| 2 | rs1986414 | 201199695 | A | 141 83 | CCTGTGCAAATGAAATGCTCATCCCC[A/G]CAAAGAAGGAATATGGGGCTGGCAG |
| 2 | rs2219366 | 81318138 | A | 143 84 | CACCAAACACACATACATACACATTT[A/G]TAGCATTTTGGAGCTAGAAAAGCT |
| 10 | rs1886951 | 2425384 | A | 146 85 | CAGCAGCCACTCCTGGCAGAACCCCT[C/T]CTCCCATGCCAGCCACCCTCTTGAG |

5.2 Methods of Treatment/Diagnosis

The present invention provides for a method of determining whether or not a human subject is at increased risk for developing ARONJ comprising determining whether nucleic acid, e.g. genomic DNA, of the subject carries an allelic variation or SNP that is a ARONJ biomarker, as described above, for example, by determining the nucleotide sequence of at least a portion of the DNA of the subject and determining whether a variant SNP which is a ARONJ biomarker as set forth above is present, where the presence of said ARONJ biomarker indicates that the subject is at increased risk for developing ARONJ. If a subject is at increased risk of developing ARONJ, the subject may be cautioned/warned to abstain from use of an anti-resorptive agent, such as a BP or Denosumab, avoid dental surgical procedures, or be frequently examined for early detection of ONJ (and then cessation of BP treatment or other therapeutic measures).

In non-limiting embodiments, the present invention provides for a method of determining whether a human subject is at increased risk for developing ARONJ comprising determining whether the genomic DNA of the subject carries an allelic variation of a gene selected from the group consisting of the human RBMS3 gene, the human IGF1R gene, the human IGFBP7 gene, the human DPYD gene, the human ABCC4 gene, or the human GSTM2 gene, where the presence of said allelic variation indicates that the subject is at increased risk for developing ARONJ. In particular non-limiting embodiments, the allelic variations may be in regions or subregions of those genes as described above, in SNPs represented in TABLES 1, 2 and 3, or in SNPs rs11934877, rs17761305, rs10875055, rs1189437, or rs673151.

In non-limiting embodiments, the present invention provides for a method of determining whether a human subject is at increased risk for developing ARONJ comprising determining whether the genomic DNA of the subject carries a SNPs set forth in TABLE 4 (i.e., any one of SNP ID #40-147 or combinations thereof), where the presence of the indicated allele of the SNP indicates that the subject is at risk for developing ARONJ.

The present invention further provides for a method of treating a human subject suffering from osteoporosis, comprising: (i) determining whether the human subject is at increased risk for developing ARONJ comprising determining whether the genomic DNA of the subject carries an allelic variation that is a ARONJ biomarker, as described above, for example, by determining the nucleotide sequence of at least a portion of the DNA of the subject and determining whether a variant SNP which is a ARONJ biomarker as set forth above is present, where the presence of said ARONJ biomarker indicates that the subject is at increased risk for developing ARONJ; and (ii) if the subject is at increased risk for developing ARONJ, recommending that the subject not be treated with an anti-resorptive agent or be treated with an anti-resorptive agent with relatively lower incidence of ONJ and optionally recommending an alternative treatment for osteoporosis, such as, but not limited to, calcium supplementation, exercise, and/or (iii) if the subject is at increased risk for developing ARONJ, recommending that the subject not undergo bone invasive dental procedures; and/or (iv) if the biomarker studies suggest that the subject is not at increased risk of ARONJ, initiating or continuing anti-resorptive therapy.

In a non-limiting embodiment, the present invention provides for a method of treating a subject suffering from osteoporosis, comprising obtaining the sequence of a portion of nucleic acid collected from the subject to determine whether the subject carries one or more single nucleotide polymorphism indicative of an increased risk of anti-resorptive therapy-associated osteonecrosis of the jaw selected from the group consisting of the single nucleotide polymorphisms set forth in TABLES 1, 2, 3 4 and combinations thereof, and if the one or more single nucleotide polymorphism is absent, treating the subject with an anti-resorptive agent.

The present invention further provides for a method of treating a human subject suffering from hypercalcemia, comprising: (i) determining whether the human subject is at increased risk for developing ARONJ comprising determining whether the genomic DNA of the subject carries an allelic variant that is a ARONJ biomarker, as described above, for example, by determining the nucleotide sequence of at least a portion of the DNA of the subject and determining whether a variant SNP which is a ARONJ biomarker as set forth above is present, where the presence of said ARONJ biomarker indicates that the subject is at increased risk for developing ARONJ; and (ii) if the subject is at increased risk for developing ARONJ, recommending that the subject be treated with a BP that carries a relatively lower risk of ARONJ or that the subject not be treated with BP and optionally recommending an alternative treatment for hypercalcemia, such as, but not limited to, gallium nitrate, plicamycin (formerly mithramycin), calcitonin, hemodialysis or peritoneal dialysis and/or (iii) if the subject is at increased risk for developing ARONJ, recommending that the subject not undergo bone invasive dental procedures and/or (iv) if the biomarker studies suggest that the subject is not at increased risk of ARONJ, initiating or continuing BP therapy.

In certain non-limiting embodiments, the present invention provides for a method of determining whether a human subject is at increased risk for developing bisphosphonate related osteonecrosis of the jaw comprising determining whether the genomic DNA of the subject carries one or more allelic variation which is a SNP selected from the group consisting of the SNPs set forth in TABLES 1, 2, 3 4 and combinations thereof, where the presence of said allelic variation indicates that the subject is at increased risk for developing ARONJ. In certain non-limiting embodiments, the SNPs include one, two, three or four or at least two, at least three, or at least four of the following: rs17024608 wherein A is substituted by G; rs17761305 wherein C is substituted by T; rs11934877 wherein T is substitued by C; rs10875055 wherein C is substitued by T; rs1189437 wherein A is substitued by C; rs673151, wherein G is substitued by A; and combinations thereof.

5.3 Kits

The present invention provides for kits that may be used to practice the above methods for determining whether the genomic DNA of a subject carries an allelic variation that is a ARONJ biomarker.

In certain non-limiting embodiments of the invention, a kit may comprise one or more primer nucleic acid having a sequence that is complementary to a nucleotide sequence containing or in proximity to the location of a SNP that is a ARONJ biomarker, as described above. For example, and not by way of limitation, the primer may be extended across the sequence having a SNP.

A "primer" as that term is used herein is a polynucleotide that is at least 8 nucleotides, at least 10 nucleotides, at least 15 nucleotides, at least 20 nucleotides, or at least 25 nucleotides in length (and may be, for example but not limitation, up to 20 nucleotides, up to 30 nucleotides, up to 40 nucleotides, up to 50 nucleotides, up to 100 nucleotides, up to 200 nucleotides, up to 500 nucleotides, up to 1000 nucleotides, in length) and, under reaction conditions, forms a hybrid structure with its target sequence, due to complementarity of at least one sequence in the probe or primer with a sequence in the target sequence. The target sequence, in non-limiting embodiments, may be at least 8 nucleotides, at least 10 nucleotides, at least 15 nucleotides, at least 20 nucleotides, or at least 25 nucleotides in length (and may be, for example but not limitation, up to 20 nucleotides, up to 30 nucleotides, up to 40 nucleotides, up to 50 nucleotides, up to 100 nucleotides, up to 200 nucleotides, up to 500 nucleotides, or up to 1000 nucleotides, in length. In non-limiting embodiments, the primer may be identical to the complement of its target sequence, may be at least 99 percent identical to the complement of its target sequence, may be at least 98 percent identical to the complement of its target sequence, or may be at least 95 percent identical to the complement of its target sequence, and may optionally be fused to a second nucleic acid or other molecule that is non-specific to the subject's nucleic acid but that is used in the detection assay (for example, for purification of extended or amplified primer).

The target sequence may span the location of the SNP or other allelic variation or may be in proximity to it (for example, but not by way of limitation, within up to 20 nucleotides, or up to 50 nucleotides, or up to 100 nucleotides, or up to 200 nucleotides, or up to 500 nucleotides, or up to 1000 nucleotides in genomic DNA or, if the SNP is located in a transcribed region, in RNA or cDNA).

In a specific non-limiting embodiment of the invention, the target sequence of a primer may be within 50 or within 100 nucleotides on either side of (i) the nucleotide that is the location of the SNP or (ii) the other allelic variation, in a genomic DNA, RNA or cDNA sequence.

One primer, as described above, may be used to generate a test fragment by primer extension. Two such primers may be used to generate a test fragment by polymerase chain reaction. The placement of the primer(s) is/are such that the test fragment comprises the location of the SNP or other allelic variation. The resulting test fragment may be sequenced to determine whether a SNP or other allelic variation of the ARONJ biomarker is present.

In non-limiting embodiments, a primer used according to the invention has a target sequence in (or is complementary to at least a portion of or is at least 90 or at least 95 or at least 99 percent homologous to (as determined by standard software such as BLAST or FASTA)) one of SEQ ID Nos 1-85.

In non-limiting embodiments of the invention, primer extension may be used to extend a primer as described above to generate a test fragment that comprises a nucleotide that is the location of a SNP that is a ARONJ biomarker. In non limiting embodiments, the sequence of the test fragment may be determined so as to determine what nucleotide is present at the site of the SNP.

In non-limiting embodiments of the invention, polymerase chain reaction may be used to amplify a test fragment between two primers (as described above), where the test fragment comprises a nucleotide that is the location of a SNP that is a ARONJ biomarker.

In non-limiting embodiments of the invention. a kit may comprise at least one, or at least two, or at least three, or at least four, or at least five, or at least six, or at least seven, or at least eight, or at least nine, or at least ten, and optionally up to five, optionally up to ten, optionally up to twenty, or optionally up to fifty, primer(s) selected from the group of:

primer(s) that may be used to generate test fragments that comprise a nucleotide that is the location of a SNP listed in TABLE 1, or in TABLE 2, or in TABLE 3; or in TABLE 4, and primer(s) that may be used to generate test fragments that comprise a nucleotide that is the location of a SNP or allelic variation in the human RBMS3 gene, human IGF1R gene, human IGFBP7 gene, human DPYD gene, human ABCC4 gene, or human GSTM2 gene, including the regions and subregions described above, and including the SNPs associated particularly with each of these genes.

In a specific non-limiting embodiment, the kit comprises at least one primer that may be used to generate a test fragment that comprises the nucleotide that is the location of the SNP of rs17024608, namely, the substitution of A by G in SEQ ID NO:1=GATAGAATAGAACTATTTGATGTGG A/GCCATGAG AATTTAAAAGTATCTGCA (bolded and underlined), where the presence of a G rather than A is indicative on increased risk of ARONJ, together with a package insert that describes the association between this SNP and ARONJ. Said kit may optionally comprise at least one primer that may be used to generate a test fragment that comprises the nucleotide that is the location of a SNP of a human gene selected from the group consisting of IGF1R, UGFBP7, DPYD, ABCC4, GSTM2, SNP ID #40-147, or combinations thereof. For example, said kit may further comprise at least one primer that may be used to generate a test fragment that comprises the nucleotide that is the location of the SNP of rs17761305 corresponding to position 57934091 of chromosome 4, as represented by the substitution of C by T in SEQ ID NO:20. As another example, said kit may further comprise at least one primer that may be used to generate a test fragment that comprises the nucleotide that is the location of the SNP of rs11934877 corresponding to position 57941026 of chromosome 4, as represented by the substitution of T by C in SEQ ID NO:19.

In certain non-limiting embodiments of the invention a kit as described above comprises primers having, as target sequences, ARONJ biomarkers as set forth above, where said primers for ARONJ biomarkers are at least 20 percent, or at least 30 percent, or at least 40 percent, or at least 50 percent, or at least 60 percent, or at least 70 percent, or at least 80 percent, or at least 90 percent, of the primers present in the kit. In such embodiments, the kit is directed toward detecting ARONJ-associated markers and does not include a majority of primers that are not ARONJ-associated, although primers to serve as controls, for example, may be included (in non-limiting embodiments, the percentage of non-ARONJ associated primers may be up to 50 percent, or up to 40 percent, or up to 30 percent, or up to 20 percent, or up to 10 percent, or up to 5 percent).

In certain non-limiting embodiments, a kit for detecting ARONJ biomarkers may comprise at least one primer that may be used to generate a test fragment that comprises the nucleotide that is the location of the SNP of rs17024608, namely, the substitution of A by G in SEQ ID NO:1=GATAGAATAGAACTATTTGATGTGG A/GCCATGAG AATT-TAAAAGTATCTGCA (bolded and underlined), where the presence of a G rather than A is indicative on increased risk, together with one or at least one primer for another ARONJ biomarker set forth above.

In certain non-limiting embodiments, a kit for detecting ARONJ biomarkers may comprise at least one primer that may be used to generate a test fragment that comprises the nucleotide that is the location of the SNP of rs17024608, namely, the substitution of A by G in SEQ ID NO:1=GATA-GAATAGAACTATTTGATGTGGA/GCCATGAG AATT-TAAAAGTATCTGCA (bolded and underlined), where the presence of a G rather than A is indicative on increased risk, together with two or at least two primers for other ARONJ biomarkers set forth above, for example, but not limited, to one, two, three or four or at least two, at least three, or at least four of the following: rs17761305 wherein C is substituted by T; rs11934877 wherein T is substitued by C; rs10875055 wherein C is substitued by T; rs1189437 wherein A is substitued by C; rs673151, wherein G is substituted by A; and combinations thereof.

6. EXAMPLE

6.1 Materials and Methods

This research involves an observational, hospital-based, epidemiologic case control study. The research protocol was reviewed and approved by the institutional review boards (IRB) of the participating institutions. Human subject participation required the signing of a written informed consent, as approved by each institution's IRB. The study base of this case control study consisted of individuals who had received bisphosphonates, and who had received care in the clinics of the Massachusetts General Hospital (MGH), the Brigham & Women's Hospital (BWH), the Harvard School of Dental Medicine (HSDM) and its affiliated clinics, and the Nova University Dental School in Florida. In addition to providing their signed consent, individual participants were required to have the ability to answer to a questionnaire, and to provide a saliva sample. No individual was excluded from the study on the basis of gender, religion, political or sexual orientation, or minority group membership.

The identification of cases and controls occurred at the level of the recruiting clinic. Initially, electronic medical records and clinical notes were searched to identify bisphosphonate users. Among the bisphosphonate users, confirmed ONJ cases and unaffected controls were identified and invited to participate in the study by means of an introductory letter. Letters were mailed at the home address of record for all subjects. Three weeks after the initial mailings, a second wave of follow-up letters were sent, followed with telephone calls. Because of multiple co-morbidities, participants were offered the option to participate over the mail or to visit the clinic for an in-person session. Further, research visits were arranged to coincide with scheduled visits in the Oncology wards, when possible. To avoid misclassification of the disease among the controls (avoiding classifying persons with osteonecrosis as unaffected healthy controls) intra-oral examinations were performed on all controls that expressed a willingness to participate. Both cases and controls used the exact same research instrument and same saliva collection method. The research instrument contained questions on the following fields: demographics, including gender, race, ethnicity and availability of medical insurance; recent radiation to the head and neck (a positive answer would exclude them from the study); exposure to risk factors such as tobacco and alcohol use; co-morbidities, including cancer, osteoporosis and various autoimmune diseases; use of certain medications such a steroids, statins or thalidomide; details of their bisphosphonate use; having interventional dental procedures prior to ONJ, such as implant placement or dental extractions; and details on the osteonecrosis of the jaw, including symptomatology and recurrence. The saliva collection method utilized the Oragene DNA collection kit (DNA Genotek, Canada).

Following recruitment, the saliva kits were mailed in one batch to the genotyping facility. DNA was extracted following the manufacturer's recommended protocol. High throughput genotyping was performed using the Human Omni Express 12v1.0 Beadchip (Illumina, San Diego) according to the manufacturer's protocol. The Human Omni Express 12v1.0 Beadchip captures 731,442 markers, representing more than 91% of human variation for major alleles with frequencies above 5% in Caucasians.

All genetic data was imported at the Columbia University Medical Center Division of Bio-informatics computer cluster for statistical analysis. After converting the Final Report file format (standard export format from Illumina's GenomeStudio) into ped and map files, all downstream analyses was carried out in PLINK software [5].

To test the quality of the genotyping and to decide the call rate thresholds (both per sample and per marker), the missingness rate was checked by individual and by SNP (locus), respectively. All samples had call rates greater than 95%. 39,456 SNPs with MAF (minor allele frequency) less than 0.01 were excluded as alleles with such low frequency they would have no chance of approaching significance in this study. PLINK was used to test for Hardy Weinberg Equilibrium and SNPs were excluded that deviated from HWE at a $p<0.0000001$. Cryptic relatedness was tested for by estimating the identity-by-descent (IBD) for all possible pairs of individuals. To estimate the effect of population structure, the smartPCA program from the EIGENSTRAT package (version 3.0) [6] was used to conduct Principal Components Analysis (PCA) in order to expose population structure of the ONJ study group. This process was repeated when looking for additional genetically—matched population controls in publically available GWAS datasets. Subjects were selected from POPRES [7], Wellcome Trust Case Control Consortium [8], Illumina iControlDB [9], and the international Serious Adverse Events Consortium (iSAEC) [10]. All subjects except the ones from iControlDB were genotyped using Illumina 1M or 1M-duo chips, and the subjects from iControlDB were genotyped using Illumina 500K chip. SNPs from known regions of long-range linkage disequilibrium (LD) [11] were removed before conducting PCA.

The association of single SNPs were tested primarily using logistic regression with the PCA eigen values as covariates under an additive model. The Cochran-Mantel-Haenszel stratified test was also utilized. Both tests take into account the population structure to minimize inflation of test scores. Standard case-control association analyses set the significance p-value at the $p<5\times10-8$ level, with the exception of a candidate gene analysis that used less stringent correction. The candidate gene sub-analysis focused on certain genes that were considered to be of interest, including the Insulin-like Growth Factor (IGF) family, and several ADME genes [12].

Subsequently the genotypes of 30 Caucasian ONJ cases and 1,743 controls from the "extended study group" (described in more detail in the Results section) were imputed using IMPUTE2 [13] (version February 2009), with data from the 1000 Genomes Project (112 individuals, release number March 2010) and HapMap III (June 2010, all ethnicity) as the reference panels. Only the imputed genotypes with posterior probability (reference) of greater than 0.9 were retained. All known SNPs with poor quality were pruned before the imputation to avoid false positives. The genome was divided into 5000 bp length segments and was imputed using ethic mixed panels to increment the quality of the imputation for rare variants. Stringent QC was carried out on the imputed genotypes. Copy number variations (CNVs) were subsequently inferred from SNP chip data using PennCNV software (April 2009 version) [14]. To ensure the accuracy of CNV calling, stringent sample and CNV filtering procedures were applied. All samples were included that had a LRR standard deviation <0.5, maximum number of total CNV calls <50, BAF median >0.55 or <0.45, BAF drift >0.01 or WF>0.05 or <−0.05 (default parameters). Additionally, to ensure high-confidence CNVs, individual CNVs with PennCNV-generated confidence score <10; those with calls based on fewer than 10 SNPs/CNV probes; and those with span within 1 Mb from centromeres or telomeres, were excluded.

6.2 Results

Recruitment. A total of 67 individuals were recruited in the period 2008-09. Of those, 32 were female cases with a mean age of 62.8 years; 15 were female controls with a mean age of 64.8 years; 5 were male controls with a mean age of 63.6 years and 15 were male cases with a mean age of 64.8 years. The majority of the cases (28/47) and controls (13/20) had received zoledronic acid, with an average duration of 22.5 months. The mean months on zoledronic acid was higher in cases than in controls, but the difference was not statistically significant. Similarly, there was no significant difference between cases and controls in mean months on zoledronic acid for the 14 subjects that reported a positive history of osteoporosis. Of the 67 individuals that participated in the study, we were able to extract DNA from 53 samples; 35 patients with osteonecrosis of the jaw and 18 treatment-tolerant controls.

Population structure and selection of genetically matched population controls. In order to identify the ethnicity of the members of the ONJ study group, the genotype data of the original study group, also referred here as "ONJ study group," was combined with that of 987 HapMap III subjects, which include subjects from 11 populations. Six individuals were found to not cluster with the Caucasian (CEU and TSI) HapMap III samples, including three apparent African Americans, one possible Mexican and two subjects with mixed ethnicity. To increase sample size, additional genomic data was introduced for various classes of controls. More specifically, the genotypic results of the 47 Caucasian subjects (cases and controls) in the original study were merged with that of a selected European study group to separate sub-populations among Europeans. The members of the European study group were selected from publicly available datasets genotyped with the Illumina 1M or 1M-duo chips (POPRES, WTCCC and iSAEC study groups), representing sub-populations among Europeans. This analysis showed that the Caucasian subjects clustered with individuals of northwestern, southern and eastern European descent (FIG. 1A-B). Based on the eigen scores of the first two principal components, 1,122 genetically-matched population controls were selected to form the "combined study group".

To further increase the number of genetically matched controls, especially subjects of Eastern European origin, the combined study group was merged with 2,978 Caucasian samples from the iControlDB dataset and PCA was used to cluster all samples together. From this merged study group, the closest controls for each case were selected based on the eigen scores of the first six principal components to form the "extended study group". Finally, the Caucasian ONJ study group was merged with 101 treatment-tolerant cancer subjects from a dataset available via dbGAP to form a "treatment-matched study group" [15] that contains our 30 ONJ cases and a total of 118 treatment-tolerant controls; of the 118 controls, 101 come from the dbGap phs000210.v1 and 17 come from our original ONJ study. Considering recent evidence about the rarity of ONJ, the Extended study group was combined with 27 additional Eastern European subjects taken from phs000210.v1 study group to form the final study group.

Discovery Phase. The Caucasian ONJ study group contains data from 30 Caucasian cases and 17 Caucasian treatment exposed controls. In total, 631,507 SNPs passed quality control. Logistic regression was used to quantify the Odds Ratio and the 95% Confidence Interval of each SNP using the eigen score from the six significant components as covariate to control for population structure. Given the small sample size, single marker association was tested by the Fisher Exact test. TABLE 6, below, summarizes the findings from the genome wide association analysis. This process as repeated comparing the data from the 30 Caucasian cases with various sets of controls, as explained above. Statistical tests of association in all genome-wide association sub-analyses failed to reach statistical significance (genome-wide level of $p<5\times10-8$). Several markers reached borderline significance at the $p<5\times10-7$ level, such as rs8012823 at DPF3; rs11802277 at AL365331.2; rs1075417818.1; rs11189381 at RP11-459F3.3; rs6861122 at AC022120.1; rs4431170 at MARCH1; rs13096022 at GRM7, and several SNPs appeared consistently in the lists of the 10 top associated genes across the various analyses, suggesting possible involvement in the etiology of ONJ. See Appendix for the 10 most associated SNPs of each analysis, along with ORs, p-values, QQ plots and Manhattan plots for each of the different case-control comparisons (caucasian ONJ study group; combined study group; extended study group; treatment matched study group; and, final study group).

Imputation Analysis. Prior to statistical evaluation a quality control routine was followed that included first using the -png-miss option to fill in the missing genotype and then calculating the Average Posterior Probability (APP) of imputed genotypes for each SNP. APP gives a broadly indication of the accuracy of imputed genotypes of a particular SNP. This parameter ranges from 0 to 1, where 1 means the complete certainty of the called genotype. SNPs with APP <0.9 were discarded. The difference of missingness was tested between cases and controls and the signal intensity was assessed manually using GenomeStudio to access the quality of genotype calls on subjects where the SNPs were genotyped.

Using imputation, 3,542,142 SNPs were analyzed and their association with the risk of ONJ was tested using logistic regression on the extended study group, with six eigenvalues as covariates to control for population structure. Two significant SNPs at the $p<5\times10-8$ level, rs17425952 and rs233723, did not pass quality control, and were therefore discarded as non-significant. One significant SNP was found located in an intron of gene RBMS3, rs17024608, to be associated with an Odds Ratio of 5.4 ($p=7.5\times10-8$). Rs17024608 was present in the genotype data of the combined study group, with a p-value of $7.3\times10-6$ (logistic regression). It was not present in the genotype data of the extended study group because it was pruned for not passing the missing rate threshold (>2% of missing data). Rs3821577, the best proxy of rs17024608 on the SNP chips ($r2=0.14$), showed association P-value of $1.0\times10-5$ (logistic regression). In the treatment matched study group, rs17024608 showed an association P-value=$1.4\times10-5$ (OR=5.6, logistic regression). TABLES 7 and 8 summarize the genetic characteristics of rs17024608 and its statistical parameters across the various datasets. FIG. 4 presents the Manhattan plot of the region surrounding the SNP.

CNV Association analysis. Burden and common copy number variants association analyses were performed. Associations were tested using two tails permuted ($\times10,000$) Fisher's exact test analysis using the PLINK software, by considering duplications and deletions separately. Singleton oversized CNVs larger than 700 kb were investigated to find evidence for individual predisposition to ONJ. All CNVs were excluded that had coverage smaller than 20 genetic markers/CNVs. All analyses were performed on the Caucasian subjects.

After the stringent QC, one subject was excluded from the association analysis. Fifty two individuals (33 cases and 19 controls) passed stringent quality-control criteria for CNV calling; 431 CNVs were called, of which 71 were duplications and 360 were deletions. Cases and controls did not differ significantly in their rate of CNVs for both deletions and duplications. After multi-test correction, none of the common CNVs had a significant association. However, two unique oversized (greater than 700 kb) duplications were found in cases, and none in controls (TABLE 9). The duplications were found on chromosomes 2 (925,407 bp) and 22 (730,236 bp) respectively.

Candidate Genes Analyses. Genes of the IGF gene family and genes related to drug-Absorption, Distribution, Metabolism and Excretion (ADME) were considered of interest at the inception of this study. With regard to the IGF gene family, 1,083 SNPs located within 20 kb of the candidate genes were available in the treatment-matched study group. FIG. 5A shows the QQ-plot for this set of SNPs. The most significantly associated SNPs were rs11934877 (OR 4.128; 95% CI: 1.918-8.885, p-value=0.0002), intronic to IGFBP7 (FIG. 5B. 2,564 SNPs close to genes related to drug-Absorption, Distribution, Metabolism and Excretion (ADME) [16] were also extracted. FIG. 6A shows the QQ-plot from those SNPs. The most significantly associated SNP was rs10875055 (OR=4.324; 95% CI: 1.999-9.353, p value=0.0002001), which is intronic to DPYD (FIG. 6B). The same two panels of markers were retrieved for the extended study group logistic regression results. Data on 867 candidate IGF SNPs and 1,247 ADME SNPs were available for analysis. FIGS. 7A and 8A show QQ plots respectively for the TOP candidate and ADME SNP panels. Top associated candidate SNPs were rs11934877 (OR=2.95; 95% CI: 1.66-5.25, p-value=0.00022) intronic close to gene IGFBP7, rs17761305 (OR=2.88; 95% CI: 1.64-5.07, p value=0.00023) intergenic SNP close to IGF1R (FIG. 7B). Top associated ADME SNPs were rs1189437 (OR=4.64; 95% CI: 2.06-10.46, p value=0.00021), intronic within ABCC4 (FIG. 8B). The same two panels of markers were analyzed in the Final study group (FC) via logistic regression. Data on 967 IGF candidate SNPs and 1,382 ADME SNPs were used. The top associated SNP was rs673151, intronic in GSTM2 gene, with a OR=3.57; 95% CI: 1.77-7.21, p-value of 0.00035. FIGS. 9 and 10A show QQ plots respectively for the IGF candidate- and ADME SNP panels.

TABLE 6

Genome Wide Association Study Results (ten most significant SNPs) for Caucasian ONJ Study Group

| SNP | P | OR (%95) | chrom | Coordinate | type | ancestral allele | closest gene |
|---|---|---|---|---|---|---|---|
| rs8012823 | 5.66E−07 | 0.09 (0.03-0.24) | 14 | 73273544 | INTRONIC | T | DPF3 |
| rs11802277 | 7.38E−07 | 33 (4.2-257.1) | 1 | 1.18E+08 | DOWNSTREAM | G | AL365331.2 |
| rs6900513 | 1.17E−05 | 0.12 (0.044-0.32) | 6 | 66333105 | INTRONIC | C | EYS |
| rs10781262 | 1.80E−05 | 0.12 (0.046-0.33) | 9 | 77650696 | INTERGENIC | A | C9orf41 |
| rs1471646 | 1.93E−05 | 11.05 (3.04-40.08) | 1 | 1.99E+08 | WITHIN_NON_CODING_GENE | C | RP11-382E9.1 |
| rs4870310 | 2.29E−05 | 0.11 (0.040-0.31) | 6 | 1.55E+08 | DOWNSTREAM | T | RP11-15G8.1 |
| rs10875148 | 2.42E−05 | 23.57 (3.02-183.9) | 1 | 98859508 | INTERGENIC | G | AL160056.1 |
| rs4562759 | 2.65E−05 | 8.7 (2.95-25.63) | 10 | 83835639 | INTRONIC | T | NRG3 |
| rs4878512 | 2.71E−05 | 9.16 (2.87-29.26) | 9 | 27630418 | INTERGENIC | A | RP11-53518.1 |
| rs1873291 | 3.18E−05 | 0.1423 (0.055-0.36) | 6 | 66344855 | INTRONIC | C | EYS |

TABLE 7

MAF of rs17024608 among different groups of subjects

| caucasian selection (# samples) | MAF |
|---|---|
| cases (30) | 0.2833 |
| controls (1743) | 0.08226 |
| exposed controls (118) | 0.06356 |
| EE exposed and general population controls (122) | 0.02 |
| EE general population controls | 0.015 |

TABLE 8

OR (CI ± 95) of the top hit in all analyses.

| COHORT | Model | OR 95% CI | P value |
|---|---|---|---|
| EXTENDED (30 vs 1743) | ADD | 5.371 (2.8-10.3) | 4.25E−07 |
| DRUG EXPOSED (30 vs 112) | ADD | 7.102 (2.731-18.47) | 5.80E−05 |
| IMPUTATION (30 vs 1743) * | ADD | 5.825 (3.065-11.07) | 7.47E−08 |
|  | DOM | 6.483 (2.966-14.17) | 2.79E−06 |
|  | REC | 23.79 (5.518-102.5) | 2.13E−05 |

* On the imputation dataset the association of rs17024608 under dominant and recessive models was tested.

TABLE 9

CVN Details on Large Duplications (found solely in cases)

| FID | CHR | BP1 | BP2 | TYPE | SCORE | SITES | length | Start SNP | End SNP |
|---|---|---|---|---|---|---|---|---|---|
| ojn5111 | 2 | 132144891 | 133070297 | DUP | 53.9 | 102 | 925,407 | rs850234 | rs16837705 |
| ojn1304 | 22 | 19063495 | 19793730 | DUP | 360.7 | 205 | 730,236 | rs6003971 | rs2845421 |

6.3 Discussion

Osteonecrosis of the jaw is a serious adverse effect of bisphosphonates, especially among cancer patients on zoledronic acid. For this vulnerable group, osteonecrosis of the jaw adds yet another burden to their already compromised health, negatively affecting their quality of life. A test able to screen subjects for ONJ susceptibility prior to initiating bisphosphonates would have a great clinical utility as it would reduce the incidence of osteonecrosis. The present study identified SNPs in the genes IGF1R, IGFBP7, DPYD, ABCC4, and GSTM2, one or more of which may be used in such a test.

IGFs, especially IGF1 with its tyrosine kinase domain, are growth factors with potent signal transduction capabilities. Insulin like growth factors are molecules with important roles in normal growth and development. IGF1-deficient children fail to achieve appropriate height and pharmacologic therapies now exist to correct such deficiencies [17]. IGF1 and IGF2 are able to influence the replication and differentiation of bone cells through activation of their receptors, especially IGF1R, which plays a role in the cell cycle [18-19]. However, IGF2R seems to have a pro-apoptotic effect since it binds IGF2 and thus reduces available ligand levels for IGF1R [20]. IGF-binding proteins (IGFBPs), produced by bone cells, compete with the receptors in binding the ligands and thus affect the bioavailability of IGF1 and IGF2. IGFBP-4 binds IGFs and blocks their action, whereas IGFBP-5 promotes the stimulatory effects of IGFs [21].

DPYD polymorphisms have been associated with fluorouracil toxicity, especially with bone marrow and gastrointestinal toxicity, mucositis and leucopenia. DPYD has also been linked to autism spectrum disorders, Barett esophagus and adenocarcinoma [22-24]. A PubMed search on "DPYD gene and bone" or "DPYD gene and necrosis" returned no results; this genotype may be potentially involved in the soft tissue aspect of osteonecrosis' pathogenesis.

ABCC4, an ATP-binding cassette transporter gene, codes for Multidrug Resistance Protein, (MRP4/ABCC4) a transporter that actively effluxes endogenous and xenobiotic substrates out of cells. Inherited variation in ABC transporters has been associated with the occurrence of serious adverse effects. For example, ABCC4 has been linked to cyclophosphamide-induced adverse drug reactions in breast cancer patients, especially leucopenia/neutropenia. Currently there is no published information on MRP4 in bone phenotypes. [25-26].

GSTM2 codes for the phase II detoxifying enzyme glutathione-s-transferase, an enzyme that protects cells against toxic insults and enhances cell survival. While a direct effect on bone necrosis has not been described in the published literature, Owur and Kong (Biochem Pharmacol, 2002) have raised the hypothesis that increased concentrations of certain xenobiotics leads to gst-mediated apoptosis, with extreme increases in concentrations leading to rapid cell necrosis. [27] Knowing that bisphosphonates are attracted to areas of active bone loss or trauma, it is then plausible that localized spikes in bisphosphonate concentrations would lead to gst-mediated cell toxicity.

The high throughput analysis of the present study was able to identify only one strong signal in RBMS3, and several weak signals in various genes. RBMS3 is a binding protein that belongs to the c-myc family of genes. The protein is located in the cytoplasm and it has two RNA binding domains. It has been shown to bind Prx1, a homeobox transcriptional factor that upregulates collagen 1 [28]. The effect of the specific genotype in the etiology of osteonecrosis is currently unknown; however, it is plausible that RBMS3 rs17024608 may be involved in reduced collagen formation and the disruption of tissue repair.

7. REFERENCES

1. Cartsos V M, Seamanduras A, Koo S, Zavras A I. Implications of bisphosphonate use in dentistry. Analecta Periodontologica 2009; 20:1-25
2. Rodan G A, Fleisch H A: Bisphosphonates: mechanisms of action. J Clin Invest 1996; 97:2692-6.
3. Fournier P, Boissier S, Filleur S, Guglielmi 5, Cabon F, Colombel M, Clezardin P. Bisphosphonates inhibit angiogenesis in vitro and testosterone-stimulated vascular regrowth in the ventral prostate in castrated rats. Cancer Res 2002; 62:6538-6544.
4. American Association of Oral and Maxillofacial Surgeons (AAOMS). Position paper on bisphosphonate-related osteonecrosis of the jaw. Can be found electronically at: http://www.aaoms.org/docs/position_papers/bronj_update.pdf (accessed last on Feb. 10, 2011)
5. Purcell, S., et al., PLINK: a tool set for whole-genome association and population-based linkage analyses. Am J Hum Genet, 2007. 81(3): p. 559-75.
6. Price, A. L., et al., Principal components analysis corrects for stratification in genome-wide association studies. Nat Genet, 2006. 38(8): p. 904-9.
7. Nelson, M. R., et al., The Population Reference Sample, POPRES: a resource for population, disease, and pharmacological genetics research. Am J Hum Genet, 2008. 83(3): p. 347-58.
8. 3. Genome-wide association study of 14,000 cases of seven common diseases and 3,000 shared controls. Nature, 2007. 447(7145): p. 661-78.
9. http://www.illumina.com/science/icontroldb.ilmn
10. Y., et al., Genome-Wide Association Study of Serious Blistering Skin Rash Caused by Drugs. Pharmacogenomics Journal, 2010 (In press.)
11. Novembre, J., et al., Genes mirror geography within Europe. Nature, 2008. 456(7218): p. 98-U5.
12. Ahmadi, K. R., et al., A single-nucleotide polymorphism tagging set for human drug metabolism and transport. Nature Genetics, 2005. 37(1): p. 84-89.
13. Marchini, J., et al., A new multipoint method for genome-wide association studies by imputation of genotypes. Nature Genetics, 2007. 39(7): p. 906-913.
14. Wang, K., et al., PennCNV: An integrated hidden Markov model designed for high-resolution copy number variation detection in whole-genome SNP genotyping data. Genome Research, 2007. 17(11): p. 1665-1674.
15. Ingle J N, Schaid D J, Goss P E, Liu M, Mushiroda T, Chapman J A, Kubo M, Jenkins G D, Batzler A, Shepherd L, Pater J, Wang L, Ellis M J, Stearns V, Rohrer D C, Goetz M P, Pritchard K I, Flockhart D A, Nakamura Y, Weinshilboum R M. Genome-wide associations and functional genomic studies of musculoskeletal adverse events in women receiving aromatase inhibitors. J Clin Oncol. 2010 Nov. 1; 28(31):4674-82. Accessed with permission via dbGAP phs000210.v1.p1
16. Ahmadi, K. R., et al., A single-nucleotide polymorphism tagging set for human drug metabolism and transport. Nature Genetics, 2005. 37(1): p. 84-89.
17. Patient Information Sheet Mecasermin [rDNA origin] (marketed as Increlex). Can be found electronically at the FDA web site: http://www.fda.gov/cder/drug/InfoSheets/patient/mecaserminPIS.htm
18. Gordeladze J O, Reseland J E, Drevon C A. Pharmacological interference with transcriptional control of osteoblasts: a possible role for leptin and fatty acids in maintaining bone strength and body lean mass. Curr Pharm Des 2001; 7(4):275-90
19. Andreassen T T, Oxlund H. The effects of growth hormone on cortical and cancellous bone. J Musculoscel Neuronal Interact 2001; 1:49-58
20. Pollak M N, Schernhammer E S, Hankinson S E. Insulin-like growth factors and neoplasia. Nat Rev Cancer 2004; 4(7):505-18.
21. Canalis E. Skeletal growth factors. In; Marcus R, Feldman D., Kelsey J. Osteoporosis. Academic Press, San Diego, Calif., pp 261-133
22. Coate L, Cuffe S, Horgan A, Hung R J, Christiani D, Liu G. Germline genetic variation, cancer outcome, and pharmacogenetics. J Clin Oncol 2010; 28(26):4029-37
23. Botelho N K, Schneiders F I, Lord S J, Freeman A K, Tyagi S, Nancarrow D J, Hayward N K, Whiteman D C, Lord R V. Gene expression alterations in formalin-fixed, paraffin-embedded Barrett esophagus and esophageal adenocarcinoma tissues. Cancer Biol Ther 2010; 10(2): 172-9.
24. Schwab M, Zanger U M, Marx C, et al. Role of genetic and nongenetic factors for fluorouracil treatment-related severe toxicity: a prospective clinical trial by the German 5-FU Toxicity Study Group. J Clin Oncol 2008; 26(13):2131-8.
25, Tagami M, Kusuhara S, Imai H, Uemura A, Honda S, Tsukahara Y, Negi A. MRP4 knockdown enhances migration, suppresses apoptosis, and produces aggregated morphology in human retinal vascular endothelial cells. Biochem Biophys Res Commun 2010; 400(4): 593-8.
26. Low S K, Kiyotani K, Mushiroda T, Daigo Y, Nakamura Y, Zembutsu H. Association study of genetic polymorphism in ABCC4 with cyclophosphamide-induced adverse drug reactions in breast cancer patients. J Hum Genet. 2009 October; 54(10):564-71
27. Owuor E D, Kong A N. Antioxidants and oxidants regulated signal transduction pathways. Biochem Pharmacol. 2002; 64(5-6):765-70.
28. Fritz D, Stefanovic B. RNA binding protein BRMS3 is expressed in activated hepatic stellate cells and liver fibrosis and increases expression of transcription factor Prx1. J Mol Biol 2007; 371(3):585-595.
29. Aghaloo et al., T. Oral Maxilofac Surg. 2011; 68(5): 959-963.

Various publications are cited herein, the contents of which are hereby incorporated by reference in their entireties.

What is claimed is:

1. A method of treating a human subject suffering from osteoporosis, comprising determining, from a nucleic acid sample from the subject, whether the subject carries single nucleotide polymorphism rs17024608 wherein A is substituted by G, where if the polymorphism is present, the subject is at increased risk for developing bisphosphonate-related osteonecrosis of the jaw relative to a subject that does not carry the polymorphism; and either (i) where the subject carries the polymorphism, treating the subject with an osteoporosis therapy that is an alternative to bisphosphonate treatment and not treating the subject with a bisphosphonate agent or (ii) where the subject does not carry the polymorphism, treating the subject with an osteoporosis therapy that is a bisphosphonate agent.

2. The method of claim 1, where the osteoporosis therapy that is an alternative to bisphosphonate treatment is calcium supplementation.

3. The method of claim 1 where the bisphosphonate agent is selected from the group consisting of alendronate, etidronate, ibadronate, risedronate, pamidronate and zoledronic acid.

4. The method of claim 1 where the bisphosphonate agent is selected from the group consisting of pamidronate and zoledronic acid.

5. The method of claim 1 where the bisphosphonate agent is zoledronic acid.

* * * * *

```
                              SEQUENCE LISTING

<160> NUMBER OF SEQ ID NOS: 86

<210> SEQ ID NO 1
<211> LENGTH: 51
<212> TYPE: DNA
<213> ORGANISM: Homo sapiens

<400> SEQUENCE: 1
gatagaatag aactatttga tgtggrccat gagaatttaa agtatctgc a                51

<210> SEQ ID NO 2
<211> LENGTH: 52
<212> TYPE: DNA
<213> ORGANISM: Homo sapiens

<400> SEQUENCE: 2
aaggcagacg tatggtgcca tgatgaratt gggtcccatg aacacccaa tg               52

<210> SEQ ID NO 3
<211> LENGTH: 52
<212> TYPE: DNA
<213> ORGANISM: Homo sapiens

<400> SEQUENCE: 3
tgagaaatga cagaaaaact atatcaycag cagagaaaac atcttcttgc tg              52

<210> SEQ ID NO 4
<211> LENGTH: 52
<212> TYPE: DNA
<213> ORGANISM: Homo sapiens

<400> SEQUENCE: 4
attgagggca ggcataagac ctcttgkcta tcatcactag gtggctcata aa              52

<210> SEQ ID NO 5
<211> LENGTH: 52
<212> TYPE: DNA
<213> ORGANISM: Homo sapiens

<400> SEQUENCE: 5
tgacctagga aggcatacaa atagttmagt tggcgtcaca ctgtttatgc at              52

<210> SEQ ID NO 6
<211> LENGTH: 52
<212> TYPE: DNA
<213> ORGANISM: Homo sapiens

<400> SEQUENCE: 6
actttcaatt ttctgaagaa atgtatwggg caactacatt aatattcttc ag              52

<210> SEQ ID NO 7
<211> LENGTH: 52
<212> TYPE: DNA
<213> ORGANISM: Homo sapiens

<400> SEQUENCE: 7
ctcatggaaa agatggcaag attgttyagt ttgtgccaga attttcctta at              52

<210> SEQ ID NO 8
<211> LENGTH: 52
<212> TYPE: DNA
```

<210> SEQ ID NO 8
<211> LENGTH: 52
<212> TYPE: DNA
<213> ORGANISM: Homo sapiens

<400> SEQUENCE: 8
gtggtacttg ttccctttta tatcacytaa cataagtata atttcattgc ac    52

<210> SEQ ID NO 9
<211> LENGTH: 52
<212> TYPE: DNA
<213> ORGANISM: Homo sapiens

<400> SEQUENCE: 9
tctatcttac aataattact caatatkttc agcagactct gaaatctgca ct    52

<210> SEQ ID NO 10
<211> LENGTH: 52
<212> TYPE: DNA
<213> ORGANISM: Homo sapiens

<400> SEQUENCE: 10
tcagctgaaa caactgtgtt attcagygta gtgtcttaat tggcagttac at    52

<210> SEQ ID NO 11
<211> LENGTH: 52
<212> TYPE: DNA
<213> ORGANISM: Homo sapiens

<400> SEQUENCE: 11
accatgagaa tttaaaagta tctgcayaaa ttgatgattt ggcatcagat aa    52

<210> SEQ ID NO 12
<211> LENGTH: 52
<212> TYPE: DNA
<213> ORGANISM: Homo sapiens

<400> SEQUENCE: 12
cttaataaat gtcttcaaag ctctcayagg agcccaagca tgtacacagt tg    52

<210> SEQ ID NO 13
<211> LENGTH: 52
<212> TYPE: DNA
<213> ORGANISM: Homo sapiens

<400> SEQUENCE: 13
gctctgccgt ttcttaggaa gttgtgraag atattggtct ttttgtgaat at    52

<210> SEQ ID NO 14
<211> LENGTH: 31
<212> TYPE: DNA
<213> ORGANISM: Homo sapiens

<400> SEQUENCE: 14
ccattaggat aaagaygagt gacctcaaaa a    31

<210> SEQ ID NO 15
<211> LENGTH: 52
<212> TYPE: DNA
<213> ORGANISM: Homo sapiens

<400> SEQUENCE: 15
tagtgggaaa gttttaaaga gaccgtyatt gagtgctttg atatgtttgt tc    52

<210> SEQ ID NO 16
<211> LENGTH: 52

```
<212> TYPE: DNA
<213> ORGANISM: Homo sapiens
<220> FEATURE:
<221> NAME/KEY: misc_feature
<222> LOCATION: (27)..(27)
<223> OTHER INFORMATION: May or may not be present

<400> SEQUENCE: 16
gaagttgtgg aagatattgg tcttttgtg aatatgtatg acactattca tt            52

<210> SEQ ID NO 17
<211> LENGTH: 52
<212> TYPE: DNA
<213> ORGANISM: Homo sapiens

<400> SEQUENCE: 17
ctctcatgga gtctacattc taaggtytca taggaaacac atgtaacttt ac            52

<210> SEQ ID NO 18
<211> LENGTH: 52
<212> TYPE: DNA
<213> ORGANISM: Homo sapiens

<400> SEQUENCE: 18
tgccgtttct taggaagttg tggaagrtat tggtctttt gtgaatatgt at            52

<210> SEQ ID NO 19
<211> LENGTH: 52
<212> TYPE: DNA
<213> ORGANISM: Homo sapiens

<400> SEQUENCE: 19
taatctgtgt taaaacaata tagcatyatc tgctttgaat gcactaggca cc            52

<210> SEQ ID NO 20
<211> LENGTH: 52
<212> TYPE: DNA
<213> ORGANISM: Homo sapiens

<400> SEQUENCE: 20
cccctggaga ataattgata gggtagygaa aaatgtggat atcataaaat at            52

<210> SEQ ID NO 21
<211> LENGTH: 52
<212> TYPE: DNA
<213> ORGANISM: Homo sapiens

<400> SEQUENCE: 21
ttcatctcac taataagagc tacccayccg cctttataca gaggttctca ga            52

<210> SEQ ID NO 22
<211> LENGTH: 52
<212> TYPE: DNA
<213> ORGANISM: Homo sapiens

<400> SEQUENCE: 22
gagtgtaatc ctaacaacaa ctcatgmaag tatttttgaa aagaatactt ga            52

<210> SEQ ID NO 23
<211> LENGTH: 52
<212> TYPE: DNA
<213> ORGANISM: Homo sapiens

<400> SEQUENCE: 23
```

```
gaaagatgag agatattca gaggatragt ggaagaaagg aggggggaaaa ag            52

<210> SEQ ID NO 24
<211> LENGTH: 31
<212> TYPE: DNA
<213> ORGANISM: Homo sapiens

<400> SEQUENCE: 24
ctggagggct tccaayggac tgatctcttt g                                  31

<210> SEQ ID NO 25
<211> LENGTH: 60
<212> TYPE: DNA
<213> ORGANISM: Homo sapiens

<400> SEQUENCE: 25
gagagtgaga actgagtggg ctggggagct katggacttt accctgccat ttcctaaccc   60

<210> SEQ ID NO 26
<211> LENGTH: 31
<212> TYPE: DNA
<213> ORGANISM: Homo sapiens

<400> SEQUENCE: 26
ttctttccat cttcartgaa atattttgcc t                                  31

<210> SEQ ID NO 27
<211> LENGTH: 11
<212> TYPE: DNA
<213> ORGANISM: Homo sapiens

<400> SEQUENCE: 27
tcaggrttaa c                                                        11

<210> SEQ ID NO 28
<211> LENGTH: 31
<212> TYPE: DNA
<213> ORGANISM: Homo sapiens

<400> SEQUENCE: 28
gataacctcc aaagayttgg ttgtaatttt c                                  31

<210> SEQ ID NO 29
<211> LENGTH: 31
<212> TYPE: DNA
<213> ORGANISM: Homo sapiens

<400> SEQUENCE: 29
ttaaaaatca atttgycttc atcacagaca g                                  31

<210> SEQ ID NO 30
<211> LENGTH: 52
<212> TYPE: DNA
<213> ORGANISM: Homo sapiens

<400> SEQUENCE: 30
ttaataaagg gtaagattgg gctatcrtat ttgaattagc agaatcactc ta            52

<210> SEQ ID NO 31
<211> LENGTH: 52
<212> TYPE: DNA
<213> ORGANISM: Homo sapiens

<400> SEQUENCE: 31
```

```
gactcatctg acttagaaat gggtggrtga aaagaatctt cactcactat gt          52
```

<210> SEQ ID NO 32
<211> LENGTH: 52
<212> TYPE: DNA
<213> ORGANISM: Homo sapiens

<400> SEQUENCE: 32

```
ctcgttgttt ttctggcact acaagaygtt ccaggttcat cttatatatt ct          52
```

<210> SEQ ID NO 33
<211> LENGTH: 52
<212> TYPE: DNA
<213> ORGANISM: Homo sapiens

<400> SEQUENCE: 33

```
tattttctaa ctctttctgg tataatrgga acagtcaaga tctgaacaag ag          52
```

<210> SEQ ID NO 34
<211> LENGTH: 52
<212> TYPE: DNA
<213> ORGANISM: Homo sapiens

<400> SEQUENCE: 34

```
agagagtaga attaagtggt ttttcaytgg aattatggag ggagaatgaa at          52
```

<210> SEQ ID NO 35
<211> LENGTH: 52
<212> TYPE: DNA
<213> ORGANISM: Homo sapiens

<400> SEQUENCE: 35

```
aagaatgtaa agcattctct agtcctrttt cctttccttg tttgttttct ct          52
```

<210> SEQ ID NO 36
<211> LENGTH: 52
<212> TYPE: DNA
<213> ORGANISM: Homo sapiens

<400> SEQUENCE: 36

```
aaatgtcacc tttgagtagt gaagttytgg atgattttta ttttcttatt tt          52
```

<210> SEQ ID NO 37
<211> LENGTH: 52
<212> TYPE: DNA
<213> ORGANISM: Homo sapiens

<400> SEQUENCE: 37

```
gctggcttct tcttaatcag aactgcyctt agcttcaaga gaggctggaa aa          52
```

<210> SEQ ID NO 38
<211> LENGTH: 50
<212> TYPE: DNA
<213> ORGANISM: Homo sapiens

<400> SEQUENCE: 38

```
ttagtaatat gcctttaagg tacctcyatc taaactgaac atgctcatta             50
```

<210> SEQ ID NO 39
<211> LENGTH: 52
<212> TYPE: DNA
<213> ORGANISM: Homo sapiens

```
<400> SEQUENCE: 39
tgaaaccaaa ctataaacta cttcttrtct ttgtgagaga attccagggc ac        52

<210> SEQ ID NO 40
<211> LENGTH: 52
<212> TYPE: DNA
<213> ORGANISM: Homo sapiens

<400> SEQUENCE: 40
tttgtatcta atgtttatat tctttaygct tgaaactatt tgaagcattc ta        52

<210> SEQ ID NO 41
<211> LENGTH: 52
<212> TYPE: DNA
<213> ORGANISM: Homo sapiens

<400> SEQUENCE: 41
agccttccca gcttgggtcc tgtttcrgag cccaggcctt gcttcccctt ag        52

<210> SEQ ID NO 42
<211> LENGTH: 52
<212> TYPE: DNA
<213> ORGANISM: Homo sapiens

<400> SEQUENCE: 42
gaatctccaa gttaattttt tcattgytta ccctttatta ctgcatgaag tc        52

<210> SEQ ID NO 43
<211> LENGTH: 52
<212> TYPE: DNA
<213> ORGANISM: Homo sapiens

<400> SEQUENCE: 43 acttttttt ttcaattctg aaatcarctt cttagatcta cttttcctta cc         52

<210> SEQ ID NO 44
<211> LENGTH: 52
<212> TYPE: DNA
<213> ORGANISM: Homo sapiens

<400> SEQUENCE: 44
tgaaaccaaa ctataaacta cttcttrtct ttgtgagaga attccagggc ac        52

<210> SEQ ID NO 45
<211> LENGTH: 52
<212> TYPE: DNA
<213> ORGANISM: Homo sapiens

<400> SEQUENCE: 45
tacaactctc aagaagcaat cttttttwtgg caggaagctg catgagtgat aa       52

<210> SEQ ID NO 46
<211> LENGTH: 52
<212> TYPE: DNA
<213> ORGANISM: Homo sapiens

<400> SEQUENCE: 46
gctggcttct tcttaatcag aactgcyctt agcttcaaga gaggctggaa aa        52

<210> SEQ ID NO 47
<211> LENGTH: 52
<212> TYPE: DNA
<213> ORGANISM: Homo sapiens
```

```
<400> SEQUENCE: 47
cactgatgct aaggcaagag ttatcgrtag cccaagctct ggctagtatc ca        52

<210> SEQ ID NO 48
<211> LENGTH: 52
<212> TYPE: DNA
<213> ORGANISM: Homo sapiens

<400> SEQUENCE: 48
atagaataaa taaggtaaca ggtaatytaa acaaagagaa aaatatctat tt        52

<210> SEQ ID NO 49
<211> LENGTH: 52
<212> TYPE: DNA
<213> ORGANISM: Homo sapiens

<400> SEQUENCE: 49
gggaaatgaa tccctggcag gatggayatt aaccaaacac ctaacacatc ag        52

<210> SEQ ID NO 50
<211> LENGTH: 52
<212> TYPE: DNA
<213> ORGANISM: Homo sapiens

<400> SEQUENCE: 50
gggaatatat ggtattaatg aaagcaytgc tacacctagg taccccatac ct        52

<210> SEQ ID NO 51
<211> LENGTH: 52
<212> TYPE: DNA
<213> ORGANISM: Homo sapiens

<400> SEQUENCE: 51
ttaagttatt gctatcctat ccttctycaa agagcttttc ttctgttttt ta        52

<210> SEQ ID NO 52
<211> LENGTH: 52
<212> TYPE: DNA
<213> ORGANISM: Homo sapiens

<400> SEQUENCE: 52
gtggaaggat ggttaccaga gggtggraag gggagtggag ggttggggga ga        52

<210> SEQ ID NO 53
<211> LENGTH: 52
<212> TYPE: DNA
<213> ORGANISM: Homo sapiens
<220> FEATURE:
<221> NAME/KEY: modified_base
<222> LOCATION: (27)..(27)
<223> OTHER INFORMATION: a, c, t or g

<400> SEQUENCE: 53
aatgataagc ttaagaaaat acaagcntaa gtatggctct taatacgcta ga        52

<210> SEQ ID NO 54
<211> LENGTH: 52
<212> TYPE: DNA
<213> ORGANISM: Homo sapiens

<400> SEQUENCE: 54
gtctcctttt cttcttgtcc cctgctytca gctctgaatg agaaaagttt tg        52
```

<210> SEQ ID NO 55
<211> LENGTH: 52
<212> TYPE: DNA
<213> ORGANISM: Homo sapiens

<400> SEQUENCE: 55
tataaagtca tcctactttc tctttcrtac tttcaaaagt tggtattcag ta          52

<210> SEQ ID NO 56
<211> LENGTH: 52
<212> TYPE: DNA
<213> ORGANISM: Homo sapiens

<400> SEQUENCE: 56
ggcgagaaag acatatgtgg atggaayatt tcagaacaac ttgtatttcc aa          52

<210> SEQ ID NO 57
<211> LENGTH: 52
<212> TYPE: DNA
<213> ORGANISM: Homo sapiens

<400> SEQUENCE: 57
ctacacttgg ggtcccagaa gagctgyccc ctcctgcaca tttccaatgc ag          52

<210> SEQ ID NO 58
<211> LENGTH: 52
<212> TYPE: DNA
<213> ORGANISM: Homo sapiens

<400> SEQUENCE: 58
ttatgaaaag gctgtgaagc tgaagaraaa ctaagaaatg gatattgctg ca          52

<210> SEQ ID NO 59
<211> LENGTH: 52
<212> TYPE: DNA
<213> ORGANISM: Homo sapiens

<400> SEQUENCE: 59
gtggttcatc tcatagcaga cttgctstag aaggtgaaac tcccggattt ta          52

<210> SEQ ID NO 60
<211> LENGTH: 52
<212> TYPE: DNA
<213> ORGANISM: Homo sapiens

<400> SEQUENCE: 60
cactcacact tgtccagagt ttcctcwtgc tttctactct tctgaaatcc tg          52

<210> SEQ ID NO 61
<211> LENGTH: 52
<212> TYPE: DNA
<213> ORGANISM: Homo sapiens

<400> SEQUENCE: 61
tagcttccac aacattccca ggctacraga gcttacagtc cattagcact ga          52

<210> SEQ ID NO 62
<211> LENGTH: 52
<212> TYPE: DNA
<213> ORGANISM: Homo sapiens

<400> SEQUENCE: 62
ttaaatcaca aatgcagtct caatccrgaa aatagatccc atcatatgtg at          52

<210> SEQ ID NO 63
<211> LENGTH: 52
<212> TYPE: DNA
<213> ORGANISM: Homo sapiens

<400> SEQUENCE: 63
tctttctcat atttatgtgc ttccttyagg agctctagta aggcaggtct gg        52

<210> SEQ ID NO 64
<211> LENGTH: 52
<212> TYPE: DNA
<213> ORGANISM: Homo sapiens

<400> SEQUENCE: 64
gccaaggggt gcctgcaggc ccatgckgag ccaccctcag acctccttca gc        52

<210> SEQ ID NO 65
<211> LENGTH: 52
<212> TYPE: DNA
<213> ORGANISM: Homo sapiens

<400> SEQUENCE: 65
aggaggatat ataaccctgg cttgaaraag atggagatag ctacaagaga tg        52

<210> SEQ ID NO 66
<211> LENGTH: 52
<212> TYPE: DNA
<213> ORGANISM: Homo sapiens

<400> SEQUENCE: 66
gttggacgga tactcatctc gtgtaayggt catagaaaga ttctgagtgc tc        52

<210> SEQ ID NO 67
<211> LENGTH: 52
<212> TYPE: DNA
<213> ORGANISM: Homo sapiens

<400> SEQUENCE: 67
ctcatgtacg cagggtgttt ccctagytga catgtctgag gacgtctttc gt        52

<210> SEQ ID NO 68
<211> LENGTH: 52
<212> TYPE: DNA
<213> ORGANISM: Homo sapiens

<400> SEQUENCE: 68
ttccaaaccc ggctttccct catttgrtcc tcaaacaccc catcgggggg cc        52

<210> SEQ ID NO 69
<211> LENGTH: 52
<212> TYPE: DNA
<213> ORGANISM: Homo sapiens

<400> SEQUENCE: 69
tagccattga caaaccctgt agacatraga atttaatatg tgataaagat aa        52

<210> SEQ ID NO 70
<211> LENGTH: 52
<212> TYPE: DNA
<213> ORGANISM: Homo sapiens

<400> SEQUENCE: 70
cacttgtcct gtggactcat gccatgycac cgtagtgctg agtgacgctt aa            52

<210> SEQ ID NO 71
<211> LENGTH: 52
<212> TYPE: DNA
<213> ORGANISM: Homo sapiens

<400> SEQUENCE: 71
ttcatgctaa aaactctgaa taaactmggt tttgatggaa tgtatctcaa aa            52

<210> SEQ ID NO 72
<211> LENGTH: 52
<212> TYPE: DNA
<213> ORGANISM: Homo sapiens

<400> SEQUENCE: 72
tagcaatgca agcatgtttg ccttcakata gctaaatgac tgcgtgattg ct            52

<210> SEQ ID NO 73
<211> LENGTH: 52
<212> TYPE: DNA
<213> ORGANISM: Homo sapiens

<400> SEQUENCE: 73
ttattcctat gcttgttggc tgcatgyatg tcttcttttg aaaagtgtat ct            52

<210> SEQ ID NO 74
<211> LENGTH: 52
<212> TYPE: DNA
<213> ORGANISM: Homo sapiens

<400> SEQUENCE: 74
tggtaataat tacaagaaaa atgtctstac atgttcagta taaatgcaac ct            52

<210> SEQ ID NO 75
<211> LENGTH: 52
<212> TYPE: DNA
<213> ORGANISM: Homo sapiens

<400> SEQUENCE: 75
tggcttcctg ggtgcaacat ccggacygat gtcttttatt gttgttattg tt            52

<210> SEQ ID NO 76
<211> LENGTH: 52
<212> TYPE: DNA
<213> ORGANISM: Homo sapiens

<400> SEQUENCE: 76
tatacacaca catataatta atgctaraag gctatacaca ggaacactat tg            52

<210> SEQ ID NO 77
<211> LENGTH: 52
<212> TYPE: DNA
<213> ORGANISM: Homo sapiens

<400> SEQUENCE: 77
gaggcctcag gaagctttta ctgatgrctg taggcaaagt gagagcaggc ac            52

<210> SEQ ID NO 78
<211> LENGTH: 52
<212> TYPE: DNA
<213> ORGANISM: Homo sapiens

<400> SEQUENCE: 78

```
aaaaaatttc atcttatatg tagtacrtag taatctataa atataaaata ca          52

<210> SEQ ID NO 79
<211> LENGTH: 52
<212> TYPE: DNA
<213> ORGANISM: Homo sapiens

<400> SEQUENCE: 79
atgttgagat agtagcacag gaggccmggg atttatttgg gttatacaca ga          52

<210> SEQ ID NO 80
<211> LENGTH: 52
<212> TYPE: DNA
<213> ORGANISM: Homo sapiens

<400> SEQUENCE: 80
aagagagaat caaaaggcag gtcctcrcag caggcgctgg gacatctgta tc          52

<210> SEQ ID NO 81
<211> LENGTH: 52
<212> TYPE: DNA
<213> ORGANISM: Homo sapiens

<400> SEQUENCE: 81
acaagaaagc aagagctgcc agggccyctt ccagcaggga ggctgaccct gc          52

<210> SEQ ID NO 82
<211> LENGTH: 52
<212> TYPE: DNA
<213> ORGANISM: Homo sapiens

<400> SEQUENCE: 82
aagcttctga ctgttaaggg tgatggwtat gttcattatc ttgacaatgg tg          52

<210> SEQ ID NO 83
<211> LENGTH: 52
<212> TYPE: DNA
<213> ORGANISM: Homo sapiens

<400> SEQUENCE: 83
cctgtgcaaa tgaaatgctc atccccrcaa agaaggaata tggggctggc ag          52

<210> SEQ ID NO 84
<211> LENGTH: 51
<212> TYPE: DNA
<213> ORGANISM: Homo sapiens

<400> SEQUENCE: 84
caccaaacac acatacatac acatttrtag cattttggag ctagaaaagc t           51

<210> SEQ ID NO 85
<211> LENGTH: 52
<212> TYPE: DNA
<213> ORGANISM: Homo sapiens

<400> SEQUENCE: 85
cagcagccac tcctggcaga acccctyctc ccatgccagc caccctcttg ag          52

<210> SEQ ID NO 86
<211> LENGTH: 36360
<212> TYPE: DNA
<213> ORGANISM: Homo sapiens
```

<400> SEQUENCE: 86

```
ccgccatacg ttatgcaacc aacagtaagt gttctcagtc acctgaggct aatatttcta      60
ttatccaagt acaagctttt ggaatgcata gaagctttgg ggtaaagctt ttgttataat     120
atgtaactcg ttcaggcagc catattctcc agataaaaag ctgttcctga aattctacaa     180
aagcatgtac aatagatagc tagagatcaa catagacata gaatcagata agagagagg      240
gtgaaaaagc aagagagtga gagagagaga gagagtgcct ggaaacttta ttagaagaaa     300
tagcaatcaa ccattcaagc tgagtctacc atttcttatg catgaggaat ttctgcttta     360
tgcaggaact cagaactccg gacaattaaa tttattctac aaggaaactc tttgtttccc     420
ttctctttct gatatgcttt tcttctttg gccacagtct gatatgcctt agggacaatt     480
tggagtatca tagacaagtt ttgacttgaa gcaatatatt tcaaatatga aggtagttgt     540
ctgctaatag atgaatttat atagatagat ggcaaggtgt gtaaatattt tcatgttaat     600
taactatagc agttttcttt ttctatagtg gaaattttct ctctgcaaaa tattcaaatt     660
ctcttttta cttgctagat ttcccatttt atggcacaat attacatcaa ttccaagtga     720
aaagtatgac gtattacatt agaatctaga ctgaaggcta atgattgcat ttatctttgc     780
ctaagtcttc cagggtttct agctctatag aagtgcgaga tagagatttc aatagcaaca     840
cactcatgag ggtgtgaggc aggggaaaga gccctagact ggaagttgtg tgacaaggtc     900
tctggtgact cttctgggta tgctctctgt gcatttgttt cctttctga cactatatac     960
ttaatagtgc ttttgtgagg atcaaatgag agatcacatg taaaagacaa tgtaaaaaag    1020
tatacatgct atgcattatt attatcattg tcctcattat tattgaatgt gttcattata    1080
caaggaagaa gcagtgctaa atttaaccc ctttagaaga taaatgtaag taagttagta     1140
tacattaaac accagggagc taaatacgca gacatccatt tcctgaactc agaaaattag    1200
agaatctggc tttcatatct gagcagggtc catttttatt ttttaaataa ggaacttttc    1260
atgttgctcc aaacatttg atagttttt atttaaagaa taaatatat gtagtttacc      1320
acagcagaac tttgtaccat attttgcaaa tccctttatt tactattatt tacacacctt    1380
gagggctttc tgagttcatc tagtctatgt tctataaatc ataccactat gcaacaaatc    1440
caggctacac ttttctgtcc aagtcataag gtaaaattca gtttgtgctg ccaaagcaat    1500
acatagcata gcaaagactg agccaacgga ggaaaaggaa agaagtcctg ccaagttctc    1560
aaaaggagac tttctggaag gaaacaacca ccttctaaaa aatgtgttca tccgtaaagc    1620
actaatacta acttagtcct catactgagt tttaacacca tctctttgtg gccaaaagga    1680
gtgcacatct ggcaaaatct gaatatttta ccagatgtca aactatgtaa gattcttcag    1740
tacttccaga tctattaggg gcagggaaga tggttgtatg ggactttatt tcagctgtca    1800
ctcaggactt ttacaaagct tttcacacac ctccttttcc accccagtac agcttcagcc    1860
tcgtgttcgc atgtattatt tctgtgtgtg tattattagt gtgtgtgtac atgtgtgtgt    1920
gtactttaat ttgtccttt agattttcct tgctgtggct actactcaga gctgatatcg    1980
tatcacctcc catgactaaa ttatgcatcg tgcttgagct taggccacta ggtttaaatg    2040
taatgtttat ggctggggtg gattcctgga aaaatagaag tggctgggcc acacaccact    2100
ttgctatctt ttagatggag aaaagggcaa aacagtatca tggaaacaca gagtttgtac    2160
catcaatcat ttccctgtaa taatcttgtt ggctgtccat attacataag taactttacc    2220
caactggctt taatttttatc atcaaagtga ggttaagtca ccctatgata ctaaaatata    2280
aaaatattca agccatctta gacaacaaat caaaaaacct gaatctgaga agaattaatg    2340
```

```
aggaacttga tgattaacaa catggattct tggttgagct cattaggaca ggaaacccat    2400
tttagcaagg gggtattgag ctatttacat aaactttctg agccacagtt tctcatctgt    2460
aacatggaca taataatacc caaataatta tgttttgttc attaaatgaa ataaggcatt    2520
aaagctctta aaataatttc tggaaaagag cactcaataa attattatta tttaattata    2580
ttagtagact tctcattatg ctttaaatta tcccagtttt atcaaatgag tgttgttata    2640
agcagaaagt tgaaagtaag caactttgtt gagaatcatc tatttctacc acattcatag    2700
tgctaattac cttactttgc taatgagttt ggtggagaaa ctctgtggct ataaacaaga    2760
caaattgctt acattggtac ttatttcact tactttctaa acattcaaca cctaaaactt    2820
aaaaaaaaat gcccattgag aatctccttt tttcagtaac tggagactac cttacaaata    2880
aattcaaggt gtcaaaatct atgtctcaaa tatattgccc ataattccaa tttgcttgca    2940
acttttcttc tctgtcacat tttctctttc ctcactttat gataatttca tgcatgaggt    3000
ttcattgtac aggaatatac ctcccctatc accaagcgtg tacactgatt cctgagttgg    3060
agccagatgt attgcctagg ctagaagccc ttcgggttct ctctcaggct tgacttaaag    3120
ggctctaatg tctcaatctg gtttgtatct gaaaacagtg cttccgtaaa gttctaaagt    3180
agagcgcaat gaccttgatc tctttgctaa ggaggatgaa tgggtaaact ggaggggcaa    3240
caactggtaa gagagaaatg aaatggcaca gagaactaaa gggaacagta aaggcatgaa    3300
agaagaatag aaaacataag catataattt ctaaagtttg ccatttaagt ttgtttcttt    3360
gtacatttaa ttttctaagt aatgtgcttg tagatttaga aaaaaaatac tctgggaaga    3420
aaggatagat gtctctttgc atggattata attctgatgt tttggaaaga aaagagattt    3480
ctgttactgg accctgggaa cttattggat ctcctggaaa gctgtcaaac cccacgtaga    3540
gaatcaagag catttctgtt tgccttttgt tattgttcac ctgaatagac tctgagaaga    3600
cagcactgtt agactaaatt aggaattccc ttttttctga gaagtaaaaa tgctgacttt    3660
gtcaatgtag ttggttattt gcttctgctt ctcagcacag acgtctatac tgcatgctga    3720
aatctcacca ttgcactaac agaattttaa tagttgatgg attgcaccaa ataacctactc   3780 tacagagcag tatgttacat tgcaatgtca tatgaataca cagttgaaat tgctgtgttc    3840
caatacattg gatattttgt tacatctgtt attactgaca aggagaaaag atgataattt    3900
tcaagaggaa gcagagttcc actttcttaa acttttattta agctcatttg aagcataaat    3960
cttctgttct tgatatgggt agtgttatat catctcaagg agaaaggtca gctttcattt    4020
tgacttaatt acaaattggt tatctaatta cagtattcta agaaatgcaa gatgcccttta   4080 ttgaatcaat acatgatttg ttgccatggc aacaaatggc aaaaaagttg caagcaaata    4140
aaaaattata atcgttatga ttaatgaacc ctgagttttc agctaaagag aaaatataaa    4200
cttcttcttt acaaccaggc tgtttaagaa gccccagaat acttaatttg gtcattcttt    4260
gcccttaaac atgtaaggcc taaggcctag ttttagagtt gtgtccttca attttgtagg    4320
tgtgtgtttt gagaaggcat tatcaccaaa tttgccctaa ttactgtaga aaatagtcct    4380
ggctttgcta ccgttaaata taacttcaaa atttttacggt aatttttcaa atataatctc    4440
agcaacttta gtaaaataac tttaaacaat gaaatgcaag gcttataatt caaagaagt    4500 gtatagagta taaaagattt tccacctagg atcccttcat tcatcatttc tattctccgg    4560
aaatacacat tgtaaacaaa atcagatatt tctatccagt caattttata tgcatatgaa    4620
attatatatt tgcatgtgtg taaatgtgta tttttaatat agaaacaata ttactctaca    4680
```

-continued

```
aatgttgtat tatgatttgc tttattttc ctcaataata aaatgttctg gatgtcaata      4740
aatatgagcc atatatagat ctatatcaat tttgctaaca gctccattgt cactactgta     4800
taaatgcacc aaaaggtgta ctttcttgaa aactcaagac agtaatatta caccctagtg    4860
agaaaacgtc tgtcagataa gttgctgaca caaaagatat ttacatttta aaatttgata    4920
tacattattt tcaaattgcc ttttagatag cagttttct ttctccataa cctcaattaa    4980
aagcaggtaa tctcaagttt taaatatttt gttaatgtgg taaatgtctc actcatattt    5040
tattttcatt tctgaatcct atgagttgag ttgattttca cgtgtttatt gactaatttt    5100
gttttcttta tctctgaact tcaagttggt ttgctttgct tagttttctt ttgaggtact    5160
gatcttttct tatttataaa agatcttatt acagttagta agtttatagt gtcatagata    5220
atttaaatat tatctcagtt gactttaaat tttaattgta tatttgtcat gcagatttt    5280 ggtatttatg tattcaaatg tatcagtctt tcttttagaa caagggtcag caaactttt    5340 ccgtaaaaag ccaaacagta aatattttct gttttgtgag ctatatggtc tgtgtcacac    5400
ctactcaatt ctatggttta ttgtgaaagc atccatagac aatacataat gaatgggtgt    5460
gccttgagtt ccaataaaac tatatttaca gaaataggta tggccacatt tgactcacag    5520
cctatatttt gacaacccca gctttagagc atctgtattc catgcaaaat accttaatca    5580
ctatagattt aaaatgccat atgttttctt actatgctta tagtaaattt tgtttaaaaa    5640
tgttgttacc tttgaagttt attttatagc atgagatgag attaagattc aaaatttcat    5700
ttttttgatt ttttttcccc caaacatgga accaattgcc ataacaaatt ttaccaaaga    5760
aaccctctat atttcgtcct ctggcataaa ttttatgcca atatttatca cataataaaa    5820 tcttttatc tttgtatctg ttttccaaat gctcttctgt cctgcttctc tatttccttt     5880
gagcattgct ctattttgac tactataact gacaatacct taatcagagg tgtccaatat    5940
tttggcttcc ctgggccaca ttggaagaaa aattgtctta ggccacacat aacatacact    6000
aaaactaatg atagctgatg agctaaaata aataaataag tcttataata ttttaagaaa    6060
gatcgtgaat ttgtgtgggg tcacattcaa agccgttgtg ggctgcatgc agccagtggg    6120
ccacatgttg gggaaacttg ccttataaac tgataggaaa tgtccacaat attttttca    6180 ttgtttctca aaaattttc tagctatttt acattttcag atgaacttta atgcatttta    6240
tgaagttaaa aatgtactaa aatttcaaat tatatattga cttatgggaa atttaagaat    6300
atgacatatt tacaacattg aattttcta tacaagaaaa agaactttc gtctacccaa     6360 gaattctttt atgtattttg gatcacttaa tagagtatca ggtttccgcc atatgtattc    6420
tatacattgc ttaatgtttt cctggcatct tagtattttt gttattatat gttttagttt    6480
tttgctgtgg ctataacaaa gtagcacaga ctgtgtaatt tataaagaaa ataagtctat    6540
atagctcaca attctggagg atggaaagtc caagagcttg atacaggcag ctggtgaggg    6600
ccatcttgtt atgtcataac atggcagaag acatcacctg gcaagaaggc aaaaacaaga    6660
gagccagaga gagcttcctt ttctaacaaa gctattccca caaatctaat tccatggcaa    6720
cattaatcca ttcatgagga cacagctgac attaatccat tcatgaggac acaacactta    6780
tttctaatgt gtaagttttg taacacatga aataaatatt cttcggcatt gcaattataa    6840 aaatttatt atatttctc attgatcact ttggtgtata aaaatgtata tactaatttt     6900
attcatttaa ttttaaaaat ctattaattg ttcaaaagta ttgctgaaat ttagaatata    6960
tacataagtt aaaaatatgca tataaaatac ccatttcctc ttacccaaag attagtacag    7020
ttaatatcta atgttacatg tttccagatg ttttctgta tttatatcaa tatctaccaa     7080
```

```
cttatctaca tctacaaaca tgcatgcata caatataccc attatatata tcatatgtat    7140
gtgtatatac catttaccaa aatgatatca gtcaaatgac atcacacaat atgtgctatt    7200
ttcagtgaat attttccatt tttcccagtt gagaaatttt ttatcatctc tcatcaaatt    7260
ttcccaattg agcaaaaatg ttatttacac tggtttaccc aatccaggaa gcaatcagtg    7320
accacatatt atatttggtt attgggtcat ttaaggctct tttaatctgg cagtcttttt    7380
tcccttcctg ttcatggtta gctgtcctgc catgtatccc actcttgcaa aatgtttggt    7440
tgattcttca tgatgctgtt tagccttttc ttctatctca tatatgaaac aattttttgta   7500 accagctatc tttctgaatt ccctcattgt tttcaatcga atatttaatt cattctcagc    7560
ttttccaggt catcaaaaat aatataattt tccacctgat tttaaatctt tatatttcat    7620
aattcatttt ctggccaaat ggctttggaa tgtatccttt gacttatttc ttatcataat    7680
ggatatgcca ctatgaatta ttttttaatt taggtgtaga tgttgaactt aatcaaagtt    7740
tttttgaaac tattgatatt attttccttt tgccaatttt attgtattaa tatatttgta   7800
attaattgta tcataatttt taatattttc ctaaggtaga atcattctgc catcaactcc    7860
atttggttat gatatatccc tgttaaaaat atacttccgg attatacttg tgaatagttt    7920
attatcttgg catcagttt tattaataaa attagtaagc tattttttgtc aggtttgaat    7980 attcaattaa caaaggcttt ataaagttaa tttggaataa ttccttttc tctaattgca    8040 gaaacaattt taaatagcat taaaaaaatc tcttttttgga gattataaaa tcttcatacc    8100
caagactatc ttagttttgg ggaagagatg cattttattt accaaatcca gtttaaaaaa    8160
taatctatta ctccagtcag acatgttctc aggaggctaa aactttataa tctatttaag    8220
aatttgttaa ggttggcccg tgtggtgac tcaagcctgt aaccccagca cttggagagg    8280
ccaaggcagg cagattgctt gaactcggga gtttgagacc agcctggggc aacatggcaa    8340
aaccttgtcc ctacaaaaaa tacaaaaaaa ttagccaggc atggtggtgc atgcctatag    8400
tcccagctac ttgggaagct gaggtgggag gattgtttga ggatagaagc tcaaggctac    8460
agtaagccaa gatcacacca ctgtactcca gcctgagcaa caaaacaaga ccttgtctca    8520
aaaaaaaaaa caaacaaaca gaatttgtta ataccatgta tgatcatgat catgaagaac    8580
tctgactgtt gcatagttga tagtcatgtt gctgaatgat caaatcaatt ggattgtgaa    8640
atgccacggt cttaacaaaa ttagcattat cttttgctcc atgactagtt gttgataatt    8700
agatcatagg ccatatagtt cttaagttaa atgtagtaca agtaaaaaat aatcagttgc    8760
caactgccta ataaggaatt tttaggtatg agcaagttgt aaatcaataa tttgtaattt    8820
ttaagaatgt atagagtttt taatgcccctt gattgtcata aaacttgagg aatattttcc    8880
tcacatgctc gcttgattca gtctttcttt cccttagccc ttagctatac caatcattga    8940
ctcctcgtct tataacattg agaaacttgg gttcaatgaa aaaaatcaac aaataataaa    9000
aacaaatatt cttgagcatc aaatatgtgc atgatatttt tctagatatt attggaaatg    9060
gaggagagaa aataagaaat aatttgtcct caagacttga aatataattg tagaaaaaca    9120
ttatatgctc aggataattt aattgaaaag gtacagttga aaatttgtca aaattttagt    9180
aattatataa cctaaaaaat aaagaagcct ctgtgaacag ttaaggacag agaagaacaa    9240
tgacataaag atgaccttaa aggatgggtg atgtttgtgg ggctaaaatg aaaaaagaga    9300 acatttaag tgaaataat acacaaaaag tatgggagga gagtctcaag ttatttcaaa     9360 gggactacg gggggagcaa atagcctgcc ttaagtgaaa tgtttatatt agagaacgag    9420
```

```
ggaaatattt ggttggaaag ttaaattgct acgtattgaa gtacaacttt cacgcagtca   9480
aatctggcag actttcctac acatttttta ttagcttgac aatcccagta ctattgttca   9540
gaatttaagt ttactttgaa aaatgtaaaa cagaaagagt aagttatgtc actgatgtgt   9600
gcgtaaaagt aataatatgc agtggagtaa tgtatgaatc aattataaat agaaaaaaat   9660
aaattctgct acattatgaa atgccattgt gcaaagtctt tgtatataaa gtcattttat   9720
attcctaaat aattttggag gtaatgttta tcttccaagt agagttcctg aaggcttcct   9780
gctgtctgag atccctgcct cctaagcaca ggagtgtcta ggggcagtgg tgagtctaga   9840
atcttttgaa atacaaaaaa tatgctttaa tacatttttt aaattctcag ataatggtgg   9900
ttggaagctg ccaagtgcta ggcaccaaca catctccaga gtacataggg atgcatctat   9960
taatagatgg ccactgtttc tatacccagt aacgtaaaaa ttgtcccaac tgaagtattc  10020
tagctctgtt actgtgggag tatgcggggc atgtgtgtgg tatgtgtgca tgtggcctac  10080
ctttctgcat gtggttttct gttattttac taacaacctt taaaatgaaa gactagctca  10140
agacataatg tatcactttt tagaacagca ggcacagcat tctggacatg acacaattga  10200
cagctgctaa gaagaaaaat ttcaatcata catgatctcc agtgtgtcct tggatagtat  10260
ttagaatttc ttcattactt catcattagt aaagcagagt atcacagctt tgccagttcc  10320
ttcataaaga tgtagatgat gttacttcct taatagctat ttaacatatt aaatataatt  10380
caaatagaaa taatgttaaa tatccaatct attaaattct tatttcctaa agaaagaaaa  10440
tatgcagcta aaataaagtc cttgtcagac tttctagaaa acagcaagtt accagggcga  10500
caatcatata gaggtagggt agatcattta ctttataaat gttaccaggg taacagaaac  10560
tactcgtgga aatcactgaa ggatttagga tgagagtaca gatagaccat ggaactattt  10620
gttctttcat agcacattgg aacaaaatgt ccaaacatat ttaaaacttt taacacttat  10680
gtgaagtatt tgggtattca ttaaatagat gatcagaaac gggttcacat attgagagta  10740
ttctcaaatg tgaagagtac atctcaaatg taaatcaaaa gatattattt ttgatttctt  10800
actgctcagt atgtcattgg gatactttat tttactctga attttgactt tgctagatta  10860
gttctagaga acctagttat ttctacctag gtgctatgtc tgcaatttag gatcatggtt  10920
aatggtgttg attagcatga ggcttgagtt ttataggtca accaattagg gtgtaggagg  10980
gagggaagtg gttaatggag agaaagggaa aaactataca tatacatata tatgtatacg  11040
tatatgtata aattttcat gtgtgtgttt gtgtatggcg tgtacggatt aatcaggttt  11100
gcttaaagaa ttatggagtt tagagttaga ttttcaaaa tgataacaca aatacaagta  11160
aaatgccttt aaacttttct actgcctaag aagaagctta ccaaagatag gaattaaacg  11220
tacattttc tccctgtttt agaacaattg gtttccctcc caataagact ctgtcagaaa  11280
acaaataatt ctaatatgtt catctatggt taacagttaa ggtatgtgca aagtctataa  11340
gcagtaaaga ggaggaagtt actcactgtg gagggagtag aggaataaga acaaggcttc  11400
acagaggagg taactcctga acttggtttt gaaaactaaa aggagttttt tagaccaaca  11460
agtgttgggt gtcaggcagg aagggtgctc tgagcaaagt gatcagtaga ttgtaggcag  11520
ggttttggtc ctattcacca tgtgctgcag ctggtgaaca tctaagagaa agcaaggtat  11580
ttttacaggc taccaggtgc ctctaacact ggggcatatg catgacattt gtgtgccctt  11640
caacagttct gccacagaag gtatcactta atcatgatta gggctgttgt cctatattcc  11700
attaaacatg gcatcttctc ctagagttcc gtttgcattt ctaggcaaag cctcctcacc  11760
aatatccgat gtgcccttc acaagttctc cactcagagt tgagtgtaat atgcagagaa  11820
```

```
tgttattgat attacttggg tatcataaag taatcattat agcctctgca caaggctaat  11880
tagtcctaat tatctgaata ccccaggtga aagtgagatt tctactcccc tcagaacccc  11940
aagaatgcgt agtgtctcat catttgactg tcaacaaatg cttcgttgct aagttattca  12000
aacaataaag taagatgata gagattctaa gaaaaaatac cagaacttat atgtctacat  12060
gagtttcttt tttctatgtg atgaaattac tttgggaggc cttttccatt gatgccatct  12120
tagactagga cattttaaaa atttattctt tgggaataat tttcagagat aatttattaa  12180
tcatacaagt aaaacaagtt catcaggtta tattcacatg atagaaaaat ggagaaacac  12240
atacataata gctagataga tagatagata gataaataga tgatagaatg ggtggataga  12300
tgatgaatga atggatggag ggaaggatgg atgcagggat gcggatggat gaatggatgg  12360
atgggtggtc agacagacag aatataggta atagatatcc tgggacatga cactagttct  12420
tctttcccaa ctacagtata atttattat ttgagagttt attccatata gttcgcaata  12480
tttctcccgt tctattttgt tctaaataaa tatttgataa taagttacac tttatagact  12540
atttctgcat tggcaaatat taagacacaa gcttccaggt gccgttagac aaggatactg  12600
acaaaggttt ctgagaaaat taaagacgtg catcttctct gaaatcaaac ccaacttatt  12660
agggaaaatg atgctaatat taaatttgtc tttgtaagtt tgatcattaa atattgtcat  12720
tgtcagtaag gaggtgtgtt aaaaacaatt taggaaaatt tctcttatgt tcataatgta  12780
gtattctaat tccttttcag ttgcagattt gtttatatca gctgaaacaa ctgtgttatt  12840
cagcgtagtg tcttaattgg cagttacatc tgtagagaga acattttct tgtggacatt  12900 tcttttatta actctcaata aaagccaagc acatgttaac tttcaatttt ctgaagaaat  12960
gtatagggca actacattaa tattcttcag gtatgtaagt ttcttataac ctatcttgat  13020
ataagaatga ctcagtaaat ccaattggct gacatgtggc ttatttggtg tttatttagt  13080
ctgagccagg atgttattaa atttatacca tctgatttat agtttcacct aggtacaggc  13140
tattttacct ctcatggaaa agatggcaag attgttcagt ttgtgccaga attttcctta  13200
ataaatgtct tcaaagctct cacaggagcc caagcatgta cacagttggg atctagtagt  13260
tctgtgctgt tgagtgcttg agaggcaaat ttcatctaaa atattgaggg caggcataag  13320
acctcttggc tatcatcact aggtggctca taaagtactc atgattttaa cagtactaga  13380
ctctgatgca cttgccaaga tgaatcaggt gtaaaatgta ctccgtggca gcaaacgaaa  13440
ctgatagaat agaactattt gatgtggacc atgagaattt aaaagtatct gcataaattg  13500
atgatttggc atcagataaa gctgatatca aaccattcta tcttacaata attactcaat  13560
atgttcagca gactctgaaa tctgcacttg agaaatgaca gaaaaactat atcatcagca  13620
gagaaaacat cttcttgctg acctaggaag gcatacaaat agttcagttg gcgtcacact  13680
gtttatgcat aatattttac aaattagggt ggtacttgtt cccttttata tcacttaaca  13740
taagtataat ttcattgcac ataactgagg agaaatagta gaaacaagct gagaaaactg  13800
aaagcaaatt ccaagaaaga ggattagtcc tcatctatgt taaaaagaac attgtgctct  13860
tggctttatt ttcttattta gcatagagaa aatcaagcta attatcaact tgggttctga  13920
ataataacct taaaacttct attgagaaga gaaacctttt atcaaagagt tattcttaaa  13980
cggttcttaa tcaatacaca ttagaaccat ttctgcataa caatgttgta tattaaaaat  14040
caattcttac tttccgataa aggctttat cttgtcttgt atctctaagt attttcaatc  14100
aatactgaaa aaatcattat gcttccaagt ttgtgttaca tgatacatgt ctaaatactc  14160
```

```
agattctgat atcacactcc aaaataatct aactttctga gatgcatata tgaaatttat    14220
ttcaaggaag tgtttatatt atacatggca tgaactgatg aatgattgat ggatactaca    14280
tacacattac tgtccatata tgctgaaagc tgacctccat tatagatatt atttaaccaa    14340
aagactgaca tatacatata atacaaatgt gtgtttatat gaggttattc agagttacat    14400
ttaaagactg aacactgttg agatttgtgg tattaattag taaggaagag aatatggtgg    14460
atgcatgggt caaaactgac tcaggaaatt tcagcctagg tggctaggta gaaagtgggg    14520
tccttaaact gaattaggat gtgtaagaga aggcataagt tgaggatcag ggatatatag    14580
ttccttttgg gcatgttgac ttttcaaggc cagataaaga ttttcaatat gtacctccaa    14640
atacaggttt gccacccaag aagggtagta ataaacttat gagtcattta ttcctgctgg    14700
agagaataga tgagatttct agcaattcgc tcacttttca tagtaattac catgcttgat    14760
ctatgcaata gctagtgttg tgcatacgct gaggttacct taaatttact agtcttatat    14820
gtactaaatt aaatgcttgc atatgcccct tacaagcaag attgtttagc aacccaatta    14880 tgcttttttct tatacctata ctgttatggc taattatgta ttgtattaca tatgtctttt    14940
tgaattaatc aaatgtatat gcacttgatg tttcctctta gggaactgac cacagtgata    15000
agttaggaaa atagagatac ttcaaattag aagaaatctt aggagccccc aatgaagtct    15060
agcagttgat gtaaaggttt cagaaattgt cctgtgtatc catgaaaagc tgtttcattt    15120
ccattttgca aacatttcag gaacttttt tttattaaat tgtatttctt ccatagccac    15180
tagcccagct agtggaagaa caacaaaatt ggaaaagcac agcaacaagc ctctgcctag    15240
taaaaaccaa gaaagcaata aacctttgcc aagcctataa gaaaaattta aaagtccacc    15300
gtttatttat cttgttgttt agatatatct gtctcattgt taagtcattg tgaatgcagg    15360
gatttataaa ccctcacacta ttatcactgg agggttccca ctgcttttag aatagagtgt    15420
tcctaaaaaa aaaaaaatcc atttctttta ctttattgac aagaatagat tatttcaggc    15480
tttgctggaa aatcccatct ttggcctttg gggctttaaa ccgtgttttt ctctaacgtt    15540
ctggttgatg ctggtaatga gaaccagttt tactgatcat agaagtatga gctcagagtg    15600
actcactaat tccaatgtgt ttccaatggc caacttgaaa aagctacata gggggatgtg    15660
agagctaaat tactgaagac catcatgttt tcctgtgggg ttttttccatg ccctgaatat    15720 gttatacatg cttttttgttg gtgttttctt ctctgttcta tttgacattt taaagagcag    15780
aagtttaaag taagtttctt aagaatccgt aacagtatgc ccgtatctcc agacaaatgt    15840
ttacaaattg gattgtggct caaagattta actttccttc atgtcttttt ctaaatacaa    15900
agttcaaacc gaaattgtca agagtgagga ttcattgaca gacaatcagc aggaggtcct    15960
tttagtggaa tattacctgt gatacaaaag gattaaacat ttcaaatata aacctttaat    16020
ctgtgctatc taattactga catctgaacc agtatcaagg aatttgtcac tttttcactt    16080
ttgtaattct aacaaagaaa agaagcaaga aacgtaattc tgcatctgga aaaaacttct    16140
aatgcaaaag catgtagctt tagtcttttc tcttgagatg gactaggata tgttccctgt    16200
atttctgatt tgtaaagatt cagcaaggca gctctgttac tgcaatcacc cttgcttatg    16260
aagttatgta gacagtccca tgtaaatcag aatggtccaa ccatttgatc ctgtccatttt    16320 ctattacaca tggtcaggca tatgatgaga aatgttctgg ctaacacaat ttcatcttat    16380
aactgtccta gaaaatgaaa taaattgtta cagcattggt ttcctagcag agccaaaatt    16440
atgcaaggag gaaagccctt ctactttttcc tcatatccct gtactctctc tgataaatct    16500
ttctctcttt cccctctcc atttacttttt ggtgctatac agattcaatt tattagacaa    16560
```

```
ttactaaatt acctcatatt attgcttaaa gtgtatcttc tcttctttaa tttgttaagt    16620
ttaataatct ccagtgaata tccattaaag agcatatgct ttttccccca ttttgaattg    16680
ttaaaagtca ttagaactag gattttgagc caatctgaaa tcagctagat attccttgta    16740
ttgctttttt tagaaaactt acttattgac tgttcagggg aaggacatat ttgtcctaaa    16800
gcaggctgtt aattatcatg aaaacttacc tattggctgt tcaggggaag cacatatttg    16860
tcctaaagca ggctcttaat tatcacatca gtctagccaa tattgtgatg gaatactgaa    16920
agtaaaggag aaccaaaaat atgtgggttg tatttccaga aaaatatatg ttataagaga    16980
atacgaaaca tgtggattgt atttccagaa aaaatgtat gtgtatttga aaattaaaga    17040
ttccttaggg gaagaaaaac ttgttttaaa ttttattaat ctcaaggtat ttaaaaatcc    17100
tctgaaagaa ttttaaaggc tgcaaattat aattatcatg taattaatta attcctgaaa    17160 tgttttttagc agaatcaaga acatttctgt tgcctggacc ttggaagaat gacagcaatg    17220
aaaaagttca tattatttgc cagtgttttt cccttaacac tgaaaatgtt aaattgctct    17280
atagttagtg acttattgga aaaacgaaac cagagtcatt cattcctcta ttcattcaac    17340
atacattttt tgggtgtctg ctatgtgcca ggcactgcca ttctatattc agttagaata    17400 caaaccaaa ccaaaaaaag atcctctctt catggaatgt atcttccagc aggggaaaaa    17460
taatttaaaa actaaaaatg ctatggcaaa tgatgttaaa tatttggagc cagattttgg    17520
taaaaatagc aagcaggtgt aatttgtctt ttagaaccc agccattatt ttcaacatct    17580
tttcttccca cttggcgatg tccttccttc aagacgctta gatgttccaa aaggtcattc    17640
tttctctctt ttgcttttc atttaaacaa catttaaaga gaacccacta tgtaccagat    17700
atgtgctgca ccatattcag agatttaatg cagtataaat tatgtatagt ccctgtcttt    17760
atgaaacttc cagtgtattg gggaagagag aaatcaaatc agtattttaa ggaataagaa    17820
attaaactgg ccatacattc tattaaagaa agattcatgg gactctaatc tcatgcatgt    17880
gtgtgtgtgt gcatgcattt ggtgggattc tcttagagag ggtcatggga ggcagaaaac    17940
aaccgtcaac tcccactaaa ctaatagtgg atgcttctcc caaaacctct cctgaaaaat    18000
ttgatctggt tattagcatc ttggggtaaa tgaagttatc agtagactta agtgtgtgca    18060
atatttttcc tattacttg taacaaaacg tttgtgaacc ttctagaaaa ttccaggcat    18120
cagcaagaag ttcattggtc ttttaggttt ggagtcttct atgctttgga ataatgtcct    18180
ccttattcag attacagaga agtccttcac tctgcatttt catgaggcaa ttatataata    18240
ttgtatatac tatcacaaaa gattaacctg aatataacag gataatgtat ttatggatga    18300
aggaagtgaa gctcagagag gttaattgtc atcactaata tcacacaagt tggtggcaga    18360
gctgggacag gtatgttca attcagttaa caccaactct atttcattat atctggcttg    18420 attttttca ttaaattttg atatgtcagg ttatataatt taacctagag taaatcaagt    18480
tggcagatta ataaaaaatt attattggat tcttctgtat atgaaagaca aaatattagt    18540
atgttatcta tgtcctttaa tgccaatcac attagcatat gaagtaagat attttttaat    18600
attttagcaa tcctatcatt atatcttaag tggaaaggag ttttatgatt tagctaaaag    18660
ctttgatttt gacagacttg ttcatccaaa tactatcata atttaattct ttgtgtccta    18720
aggttagtta aaacctttga tctgacaggc acatgcatcc aaatgtaccg taatttaatt    18780 cttttttgtct caaagttatg ttatgttggg tgatatgtct gaggtaaata tgccttattt    18840
ttaatgttca taatcactga ataagaccca ccttaatgtt ataaatattg tagcgctatt    18900
```

```
tcaggttatc agattaatga tactgtttgc actttataaa agtagatta gataactatg    18960 agaaaattct atgtaagtat ctaaaactat atgctaacat tcttttcaat ttctacacgt    19020
aagatagttt attgttgcag catataatta attttgagca ttatacaaca tttttattta    19080
attttttaag atgagacttt ttttcaaaac cctacatatt aagtctaaaa gatcaaagaa    19140
ctctgaatca aacccaaatt gaatagtttc ttctaaagta ataatatttt gtcattttcc    19200
ttatattaga tattatctac ttgtaaaact aaaagttat aaaaacaagc aaaaagcttt    19260 atctttttc tttttatata tgcttgaatt attttaaaa tgagaaaaca attttaata     19320 aaggtggaac atttcctact cttttaaaga gttttcctg attaaatttt aaaactactt    19380
aggaaatttt gcttataatc ctgcatttat gtaatggcat tgagaataat ttgccaaaca    19440
cagaccttat aatactacag aaacaaatcc agagagcttt actgaccagc tactgactca    19500
ctaaatgaaa gaaaaagacc attcccattg aaaaataata tcaatattga attatccatc    19560
catggcatgg gggaatacag catctcttcc aggaagtcag agatggacag gtaaaatgaa    19620
gagccagaaa aagaatttct cataaaagaa agtagagaaa ttaagctttc ctggaggaga    19680
aatgcagctg ttcgagctgt ggaatttcaa tgcatgcaga cctcacatct atctcatata    19740
taggtgtgta tacactcgct tcatgtgaac tttgtgaagt caatcattgc tccatttgct    19800
aatcccagtt tcaattttg tcagctgtcc ctctatattt tcagtgtaaa tccctgtctc    19860
tttgtaatta taaccaaaac atacatgtgt ttaatcacct ctctatcttg acaattttt    19920 gttttaatac ttgggatgcc ttcatggtgt aggcctaggg aatcctgcct tgaactacat    19980
tcaaggggca ggaattctag ctgcggattc catttccctg taaaattatg cagccctggc    20040
tgcataatgc tgtcactgcc tgaagcagct gctcctgctg ctttcagcat tgtacattgt    20100
caacttttct gtcacttcat tcacaaactt tgctcccaca ttgttcacat aatcatctct    20160
ttgcttcttc ctacacccag attttaagga aaataattat gaaataattt ggtagatata    20220
atatgatttt agagtagtaa ctccagaact ctttagaaaa gccagttgtt cccttattga    20280
tctctctact tttttttaa cgtacttagg aaaaaattgt cgcatgacta tttaccgcag    20340
gtctgactca agggaaaggt catgcatggc agtaataaga agcaagatcc tcacagacat    20400
gctgaaaatt agccacatgg ggttataatc aaaccagatc aagaaaggtg actgagacca    20460
aataaaatga aatgtgaatt gtcattcact tttgctggta agttttgaaa tttgaaattg    20520
accagcaaat ttcctactcc tcttgtgtct ataaactgaa aaactgggaa gttcatttat    20580
tctttgacta ctagtaattt tgtagtatga gtaaattgga aagtatgatt actgttcttc    20640
acaatgtaaa ggtttaaaag aatgccaaac taagcactgc attttattgt tgttttccaa    20700
agccacaggt aaataaaaag ttttctgttt ttctgaaatt tttgcatact actactttca    20760
tccaaaaaac aatgtcctaa atagatgatt taaccatgtg agttcacact atagctgtgt    20820
cactaggatg gggtgaaatc atcatttcat atttggatat atccttggaa tataattttt    20880
tttaactttg acaactaatt tcctgattcg ttaaagtccc taatgaatat acataaaata    20940
gttaacttaa atacctcaga taggcaggtc atggtggctg atgcctgtaa tcccagcact    21000
ttggaaggtg gaggcaggca gatctcgagg tcaggagatc gagaccatcc tggctaacat    21060
ggcgaaaccc cgtctctact aaaaatacaa aaaattagcc aggtgtggtg gcacgtggtc    21120
tcaaaaaaaa aaaaaaaaaa acctcagata tgattataaa ccagtgaagc ttaatatttt    21180
ttaattaagt ttgaattgtg tacatttggg ggtgccgtgt aaaaaataca ttttaaaagg    21240
aaggtcttat accgaggcca ttggatatta atatttgttg ggtctagcct atgaagaaat    21300
```

```
catgaatta taatttgact ttttgttttg gtttgctgtt gttgttttga gatggagttt    21360
cactcttgtt gctcaggctg gagtgcagtg gcgtgatctc agctcactgt aacctctccc    21420
tcccaggttc aagtgattct cctgcctcag cctcccaagt agctgggatt acaggcgccc    21480
gccaccacgc ctggctaatt ttttgttttt ttaatagaga cagggtttct ccatgttgac    21540
caggctggtc aggaactcct gacctcaagt gatctgcctg cctcagcctc ccaaactgct    21600
gggattacag acatcgagcc gcagcacctg gtttagtttt ttttaaccct ttataaaata    21660
cccactatag tcagaatagc cactcagaat atgtgggtta gctgaatttg ctatcccatt    21720
gccatacaaa ttctaaaagc tatcaactga cagactgttt ggcagggggg tggggggggct    21780
gggggtgcag caaaaatagt caggaggaat gacacaataa aatattacca atcaattaac    21840
cagtgagttg acaactggcc ttgatcagag ctaaggagaa agagggctct ccctataatg    21900
agctgtgatt aacaacagga attaccgaaa tgtaattata gccaactctt cagagatgag    21960
ccatccatgc cttgagactt cagggtctca gtaaagatag aggtattttt gttcttgatt    22020
actaagataa caattgagcc atgttttag atgcaatccg gtgtgtctac aagccttcat    22080
catattttag agttatttcc ttcctacagt atgtttttca gcttgatact cagtgatctc    22140
aggcttattc ctggggaccc agagcctcct gctgaagcaa acatccagg cttgctcaac    22200
atagacagtc cctaacttaa cagtgggaga tgcaagtctt gtggctcaac tgtgactcta    22260
ggagttgagt ggtagtagca tcacccagtg aaaatttcag actaaaaaaa agacagaaaa    22320
tgacatggca tctccaataa tgtttacttt tgtggaaat tgtaatctcc ttgattactt    22380
tatattgcat ttgtgaaact tactctatta tagcttgtta aagttattta actgtaattt    22440
atctctcagt tatttcacag caagatataa cagaggccgg gcacggtggc tcacgcctgt    22500
aatcccagca ctttgggagg ccgaggcggg tggatcatga ggtcaggaga tcgagaccat    22560
cctggctaac aaggtgaaac cccgtctcta ctaaaaatac aaaaaattag ccgggcgcgg    22620
tggcgggcgc ctgtagtccc agctactcgg gaggctgagg caggagaatg gcgtgaaccc    22680
gggaagcgga gctttcagtg agccgagatt gcgccactgc agtccgcagt ccggcctggg    22740
cgacagagcg agactccgtc tcaaaaaaaa aaaaaaaaaa aaagaaaaaa gatagaaact    22800
cagcattcgt gaatggatga attaatgaat attctttatt ctaaacactg tacagtacca    22860
aaatatcttt taaaaagtta tgaaggctct aacattgcag acggtttggc atatatacta    22920
taatttgagt acccccctcag tatttcaagt tgacacaatt cttactacta aaagtattgc    22980
tttatcaatt tcaagccagc taagatagac ttctttaaaa acagatcaat ttttgtttct    23040
aaaaatatat cctaatatca gggtattatt ctaccacaga gaattcacat tgattgtcta    23100
tccatttaaa acaatatagt tatagtcttt tcacagtatt tcaaagactt ggataagctg    23160
gcggtgtaaa catttcctcg tgggaacttt ataaaatgaa aagaaaataa atgattgatg    23220
catactcaaa ctaattgaag tggtactgag tcaaccagat gttttcacct gaatcatgcc    23280
cacagatgct attgcttcat tatcccttaa tctagggatt acctccattg gctaactcga    23340
tgacctgtga gggtttcaaa taagattgcc tctcccttgt aacatacatc ataaagagag    23400
cttgtttaga ggcagcctac ctccgccctg aacatgtttt caaggaagtg atcagggctg    23460
tttgttttc ttgctgttgg atgtggtctt cagtgaagtc acaggaatgg aatgagagtg    23520
gccacagttg acaatggagc tatttccaca gctggctgca aagagtgggc agtccatcac    23580
agataaacta gcacatgggg atagatgata taaaacatct gtcacaatag ggataagcaa    23640
```

```
aaacaacgtg cctttgaaga ttgtgtttta atgatgaggt gggggttct gtctctataa    23700 taggaatgaa agatgtgttg ttggtgggca gatggcttca ggcttgctct tgcatgaaat    23760
aaagcaaaag tatgtgttaa aaatctctga cagttgtcaa gtcacctgat tttgctgacc    23820
gttcatttcc ttgcctatcc catgtgtaat ctatgagaaa agaaaggag tgctaggaaa     23880 aaataatggc agaaaaaaaa aactggttct gaataatttt cttttggata actttaatac    23940
atcagtataa ttttaactgg aggctgagag gtcagaaaac gtgttttgc aataagtttc     24000 tttaatatat ttgcatcccc atgtttttt ttatagaagt tttgtaaggt aatataaaaa     24060
tgctatgtca ccaaggccac ataatgataa atatttcaaa tgtgaatacc aattagtaga    24120
cataaagtcc tatttgttcc tgttaaagga gcagtgagga aaaataaaga catcttaata    24180 aactatttt gatgtaatta taatagtttg gtttcccacc ccatctgcct ttgaaaataa      24240
attaaaaaca ataaaattca catacagttt tatttcatat agttgctata gaaaagaaa      24300 tctttgcaac agacaaactg attgcaaata aatgccgaat attcttgcac aatacaattc    24360
tatatatacc ctgttacatg accaaagggt accactgtca ctgctgtccc ccaaaccatt    24420
ccactctgct ctggtaagga aatggttgcc attgctgcac actgaaattt tgctactttt    24480
gccacaaccc caccggaaaa atggatgtca cattccttgc tcatttatta ttttaatctg    24540
tctttcaact ctaattccct tgcaggtgct tttgattagc agaagtcaca aatctatatc    24600
tagcagcaaa agggtgtagg aaatgttttt agaagggttt tcttttcttt tttctttttt    24660 ctttttttc aattctacat tgaagaggta ggattcacac tgggggaaac taatgacatc      24720
tgaagagagt attaaaaaat aaatttctac atccatgaat ggcagaggta caccacaaga    24780
agcaactgga ctggtcaaaa taagagatct taaagaaaga gcagtgccag gcatggtggc    24840
tcacgcctgt aatcccagca ctttgggagg ccaggggcg gatcacctga ggtcgggagt      24900
tcaagaccat cctgatcaac atggaaaaac tccgtctcta ctaaaatgc aaaattagcc      24960 aggtgtggtg gtgcatgcct ataatcccag ctactcaaga ggctgaggca ggagaatcgc    25020
ttgaacctgg gaggcggaga ttgcagtgag ccaagatcac atcattgcat tccagcctgg    25080
gcaacaagag cgaaactcca tctcaggaaa aaagaaaaa aaaaaaaga gagagagaga      25140 gaacagattt aaaggaattt gtgatgttct gacaagactt gactcctgac tgagttttat    25200
ggctgatgag ggagaaggaa acgatcaaga tgacttagga gtttctttgt tattctgaga    25260
atcgagcaga gaagaaagaa tactctgaga atgaaagagg aagacagcat tcagagcggg    25320
acatagtagt tttgaggtac atgggattcg gtcagtagtt ggaaatttgg atcatgaatt    25380
cagaagaaac accaaggcaa gaaagacttt tttaaaactt taattttaa actaattata     25440 gcacttttga ttaatcaagt cttaacaagc gggaatattt tggaatttta cttctaacac    25500
cttattttta tggtatgtat attgagctaa ccaaaatatt tcgctgctgt ctcttactat    25560
tctatgcggc ataccatc tcttctaatg cttggctgtc atagctattt ctaactcact       25620
ggttaagcag atgacgttat ttggaaagaa tggaggtttc agtgtgaagg ttgccatgaa    25680
aatatgtcat aggaaagaa agggaattt tttgttaaag gagatttat gggtaaaggc        25740 agaaatcgta tggagatgat tgaggaacta tactaaatat cagtggctgt catttataac    25800
aaggagttat attaatatta ctaatattat tccaagctat ctggctctca agcaagaaca    25860
aacaaaggac ttaacaaaat gattgagagt caaaccaaga atcttttag aagcaatgta     25920 atagaaaatt cactcagagc cctggcagac caaatgcaga gctaagcttt ccaaagttta    25980
tcgtgaatat aactcacctg gggcaggctc taatttagtg gggctggggt tcacctgaga    26040
```

```
ttctgtacta agctccctga tgatagtatc cagtcccagg ccatacgtta agaaacaagg   26100
tagtagagtt taagaacatt ctattaaact aaaaaaaatg ttaaaattaa tcatatagta   26160
ttactgctta ggagaaatgg caataaaatc taagcggaat aaaacatgta actaagtttc   26220
ttgcacaaat cctgaaacaa ataggacact gaaggataac aagataaagc tgtcttttat   26280
ctcatctgga cagttttaaa tatattaatt gaaatcttga aggcctcaga atgtaacttg   26340
tttggatgct aatatataag ttttaacctt agaatatgtc tgttacacca ggacatattt   26400
tatctcagca ttagaccaca gaacatgtca tcaatagggt atatactgag tttgaagcat   26460
gttagcaata ataatactaa tagaaagtgt gctttaaaag gagtaaatta gttctttaat   26520
agggtcgtga cttcacacct gtatccttag atctagttaa gtttccagcc ctaaccaggc   26580
aaattcctaa aaatatctta aaggagaaaa atattctctg agggaccaca aaataaagtg   26640 cttttttgcag caaattgcag gacaaggaat agctactttc ttagtaatag ccaaaaattg   26700
aggtgccttg tgcatatattt aggcaacttg cactataaac aatggccata agtaagataa   26760
caggcagcta tttctcttga tcgcccctgt ggtttgagca atgattttcc aggcccattt   26820
gccaatagga tcttacaaga ccttgaaaag gatttgcaag caggtctttc agtctatttg   26880
tcagtaagga gaagttttta atgagaagtt ttatgacagc tcacagtcct gagtcctagt   26940
taaacccaga taaacatttt accagacaaa agatgaggtc cataaatatt cagacgtctt   27000
ctgggaaccc tgtttgcctt atcatttgga agaaggctgg cctgagtact gcatccgatg   27060
tgtgcttgaa acttctgtaa gttgaaaatg tgtttggagg tatacaaagt gattgctgta   27120
caaatgaata aagcatttct tatcacatga caaggtttga caagaatctc aggcagatat   27180
atggctacta aaacagttca tggcatagca aagtcctaat ttaaaaaacc ttaacctaca   27240
tttgtggcag tacacattgg ctgtaatatg tacagaacat cttgcagcat ttaactgagc   27300
ataaataatt cttccataga atggaaatca tgtcgtgaac tccaatgtta aacttccttg   27360 ggtgggggtgt ggctctcaga agccctggga ttttcatact aaataatgag aaggtcaagc   27420
tggcagtggt cagactgaga tactgtcaaa gaaaagcaga ggaagtgtat gaatggatct   27480
tttacgtcca tcttttttggc cagagaatgc ttctggtatt tccattgaat cttcttgtcc   27540
agtttgagca aggagctgct gttattgttt cacataccat taaagtcatc agagacctgc   27600
tggtgagcaa gtgccattca ctcactcagt ccattagcac cactaactaa gcatctgttt   27660
tatgacagac actgtgctgg gctcagaacc attaaaaaag aaatatataa ggtattgcta   27720
atgataccag tgaacttagg attcagggaa gaaataaagt ttgatcatga tcaaagtgtg   27780
tgcaaaatgt tatgggagaa gagaggagca agtgaccggt agcctgggtc agtcatagga   27840
gttattcccc agaatttagt atttgataag aattttagaa gacacatata aactgctgta   27900
gaagcctagc gttgcaggcc aagacagcaa gggtaagagg taagacggac aagagaatga   27960
tgaggaatac agtgtggtgg aaagagaggc ttcatgtgca tgggctgggg atcaggctag   28020
aaaggtaaat tgaaagctgt gtgatcctcg tagattatgt gtgctatgct aacaaggcca   28080
tcccagacct acctgtagaa gcctcttttt gacagagata atgctgaaac agagtagaaa   28140
gcacatgctc ttgggcagcc ctacaactca ttcactctaa ctggtttctg aataagacaa   28200
gcaggaatag aaaaatgtct tgtcctgtca ctgaactgtc ctatctactc ttacactcct   28260
ccaacacatt taatgtagaa tagccattga cttaacagta ccagtgtctt aaaaaggaca   28320
tttccactat gaaaaactaa cgcagctcta ggttgcactt tgggaaagga ggtcatttaa   28380
```

```
cactgtttcc cttataaccc cacttagaac aaaaaataag gagaaactgg tctgctcctc    28440
ttcaaatttt atatatatat atatatatat atatatatat acacacacac acacacacac    28500
acacatatat atgtatatat gcatacatat acatattgtt tttaaggtag aaaaaattag    28560
gaactaatct caatatttca aatataattt tttattatga aatatatttg gtgggtagag    28620
atcaatggtt ttctttctaa aaaaagtata gaaggagctg aaatatattt gattaatcaa    28680 ttcatttttta agtgtcatag ctttatagtc ttttgtcttt gatttttttt gtcttgtgct    28740 gttttgatt cctttaaata aattttggag tgtgcaatac atctgtatag gaaagctata    28800
taccatgggg gccctgcaaa gcaaagacta aggactatgg ttatgccact aattttttca    28860
cacaaatagt ctcatttttt cacattatct acaccacaac acatgtattt ttatgtaaac    28920
tacagcagtt tacatgtgtc ctctaaaatt cttatcaaat accacattct ggggaataac    28980
tcctatgaat gaaccagact actggtcact tgctcctctc ttctcccata acatatttga    29040
accaggctac tggtcacttg ctcctctctt ctctcataac atatttgaac caggctactg    29100
gtcacttgct cctctcttct cccataacat atttgtgagt ggtagacacc cccagctgaa    29160
agctactcat tagttatgcg attggaatca gaagctgatg aacacaagtt caccctttgt    29220
cattgaagct ctaaggtcct tctgaagtgg cctgggatct ttctctaaac aattaatatt    29280
tccattgact cagcagttat gatctcctta agtagaaaaa taagaggaaa aaatatagta    29340
acccatctgt gtaagaaatt tataatctta agatcaattc tgtaatcaag tgtacaagtt    29400
taatgacaaa ataattaagt gtcctattgc atattcagtc aacaaaatcc ctttgaccgt    29460
agagtcctca aaatctcaaa ttttcaactc tccctcaata atgcaatata tttaaaagcc    29520
actttgctct attaggattc taaagaagct actgaaaaca ccaaaagcta ctgataaact    29580
tgtttctgta gttttaggca caaacgtcta aaggattaaa ataaagcatt attgagaatc    29640
ctaattatct atgtacctgc tttggtaaga aatacttcaa tatgacatat ttactttata    29700
ttctcattca aaatgacact attatattaa taggtactta accaataatt gaaaccatta    29760
ttcacagttg aataggcgta gtacataatt aggattcttt taaagggatt tccatggcta    29820
aaactaattt ggcttagtg tctattaata ttataacttt aaaaaaaaat acttccagtt    29880
actagttact gaatcaaaaa tcaacttgaa attaaaagtg tgattaagag tacaaggaaa    29940
aaaatgctat gtttataatt aatagatatt ctgttattgg gaaatctatg tacatgtaca    30000
tatctcttct acctttatca tatagcagtg gaaaatgtct tacttctaaa cattataccc    30060
ctagcccata gctatatatc tccatatagt agtccaaata tcatgccaat tagtctaatc    30120
ctgtccaagc ataggaaaga gaaacccagc tctagtttgc cccatttcca aaataaatag    30180
caaaataagt tagcactcaa aaataatgat aaagccattg gaagtcatgt aatagtcctg    30240
ttttctttca ttgcacaatt atggaatttg ggaaattggt gtatattata accataatct    30300
tgccatagat ctaaaatgtg ctattagttg tcgggaacag actgtagatg aatactttgt    30360
gtcacttttc tttctttctt ttttttttt tttttttga gatggagtct cgctctgtct    30420
cccaggctgg agtgcagtgg catgatcttg gctcactgca agctccgcct cccgggttca    30480
cgccattctc ctgcctcagc ctccgaagta gctgggacta caggcgccta ccaccacgcc    30540
tggctaattt tttctatttt ttagtagaga cggggtttca ccgtgttagc caggatggtc    30600
tcgatctcct gacctcgtga tccgcccgcc tcggcctccc aaagtgctgg gattacaggc    30660
gtgagccact gcgcccggcc tactttgtgt catttttcta gttactgcct ttcaaattct    30720
tcctcacttt gtataaatgg agcttatgga tatatgtata tatggaccag ggtttctgaa    30780
```

```
ccctagcact aatcctgggt ttgctggata attatttgtc gtggggaact gttctctgtg    30840
ttgcaggatg tatagcaaca tcaataacca ctaccccta ggtgctaata gcacacctcg     30900
gcagttatga taaccaaaaa tgttaccaga cattgcaaaa tcactcctgg ttgagaacaa    30960
atgaaatatg tacatataca aatacttttt attctaatat atatatatat atttatatgt    31020
ctcatatagc attagtcaaa ctttttcat caagcaaatc ttggatttca tctttaaggg     31080
gatggtggtt gaagatgtca ttaatgcgca tgtgtgagtt gaactatggt tttaaaactg    31140
aactgcccct tgggagaaca agttttctca agaattttgt aatgatccat tttaacgagc    31200
aatctcaaaa taacatttct aactaactac tttttgatta gaagttttat tctttcatca    31260
ttctttcggt gaactcttat aaagcatata ttatatacct cacactataa acagcactat    31320
agacactaga cagtggtgaa caaaacaaca taatttcaac cctttcagaa taaacaatca    31380
aaatgagaaa tattagtaaa tatttacagt ttgtcattga actgaaaaat gagtggtact    31440
gatatataaa attaatttac aaaaactgtt ttgagtactt actgcatgca attcctattt    31500
atagagatta caaaagttgt ataaacataa tgtcttccct cttgaaagat gtaacgtgga    31560
aagaaacaag tagacaataa taaggggaa ggaggtatta agtgctaaag tgaagttcta     31620
ggggcagtgt ggcttctggc ttaccatgta attcatcatt tcccatacct ccagcatttg    31680
tcaaatcctt ccaaaatgct tacaaagtta aaggctacca cctttgccac atcttttgaa    31740
tttcaaacat aattttttaa agttggactg cactactacg ttggttggaa atttatcaag    31800
gtagataagg attaatgatt gtttctaaga attagagaca tttcttactc cttttgtttc    31860
ttctccccac aaaagccttt cttaaaccct gaaccctcat caaaacaaaa caaaacaaaa    31920
caaaacagtt gacatcaaca aatgaaagaa attagacatc cctacatata ctacaagaca    31980
aggaatgttg catgctaata ctgcagaaca ctgcatttgg acagctattc ctcaagctac    32040
cttcatgcca tttatattat gagatctctg ttgctattag gtatttgttc taggaatatt    32100
aaaaactggc aaaaatcaga catgaataaa agaataatga aatagtgact taaaaccacc    32160 ttttttaaaat tcatatatag ttttgtgtga ataactatag gcaatcgtat aatacaaatc    32220
acagacattt tgacttgagg catttagata agacagcaga aaaaaaggga tgctgttttt    32280
ttaattttca cttatccaaa taattttatt tttgttttc catttctatg agttcaaatg      32340
caaggctact aagattccaa atatgaagga ttcccaatgt gttataatag aagccaaact    32400
gatcaaattg aagcatgtca ggtcatcaca cttattcagt gattatatgg tgtgattatt    32460
cagataatat ttctaggtca gcccatcaaa aatgcaggct tagcccctt gaatgttttt      32520 aacaagatat aatgtgatta tcacataaaa gaccatggcc tgtaaaaaga ctggattcaa    32580
acaaataaat gagaaacagc gtacataaaa taaagccact tgtttgcctg taagaactgt    32640
aacactggct ttatacgata gcagttttta gacagagcat acttcttaaa ctttagagta    32700
tatcagaatc acctggagag cttgttaaaa tacagatttc aaggcctaat cccagagagt    32760
ctaatttttg tctactgctg ctactgatcc acaaaccata gttggggtgg cactgaccta    32820
gaatactatc acaggaatat taatgcagct agttcttctt attgtggttc atcttctggg    32880
attaatatag gtgctaaaac agctatgtgt gctctagatg gtagagaagc cacacatgct    32940
tttccctgat ttgccaatgg ttttgtattt cagttgggaa attaaaatat tgaactttca    33000
aagacttcaa atttctttca aacattggca gaaggttaac aacacagatg cttttctggc    33060
cttaggtcag atatatttac gccacacatg atgatctttg gaaactttac ccaaattact    33120
```

```
gttgaaaatt gtttatttca gaactagggc aaccagatcc acccttttgtc tcttgagtgg   33180 gagcagcttt gttttgcaaa ggcagtggct aaaaaggacc agacctttcc atcagctgtt   33240
tggtcattgt atttttagt ggaattatag cattgtacaa tattttttctt tgcagcccaa   33300 acattgagca aagccagaca tccagagatg ctaaaatgaa aaatctgttt cttcttgctt   33360
tgccacttgc caggtgaact ctgtcagaca ccacatccta tacatctcaa gtaaacaaaa   33420
ttatgcttaa tgtgttggca acatctgtca caaacactct tcagcctatg cttaaaatat   33480
attaagttgg agtggatttg acagtgtatt taataagtca aagttacggt tgtggatact   33540
ggctttgcca tgctaaccat aaggcttttc ttttcttctt ttgtatttat ttattttatgt   33600 catatacaat acaaaagaga ttctgtagtt ttaaataagc aaagtggctg gcaaactccc   33660
cctttgctgt aggtaaccaa cactaaacct ctctaagttg tctgtcccag acaaagtatc   33720
attaagaaaa ttcatttctc ccaggagttc ctattagtta cttccagtttt actccctgac   33780 tgtacatttc ttccattccc ttaagattaa aaaatttgta ttcttaataa tttgtaggat   33840
tgttttcact gaatgttttt attgaatgca aacaagactc tagattctta catatccttc   33900
cccaagaatc cttatttttat tttttatttta tgtgcaataa ctgatctgct tagaaagaac   33960
tgttcattta tgtgcagtaa ctggtctcct tacattattt tccactctgt gcctagtgtt   34020
gctatttaca attccaatta atgataaatc ccttcttact ttccctttg attgtcaggt   34080 ttctggttta tacacagaag caacactcac tctatgacat ctgtaatcaa atgagtcccc   34140
aaatactgct ttcaatgaaa agattctgaa agagaccaga caattcttcc aaaattaatt   34200
ccaagtgcag gcattcgatc cttctcatca tgcatgaatt ttgattgttc tgtcacatgc   34260
tcacctacct catctgcata ttgccttttaa aaaaaacaca ccctggggga atgagacaac   34320
ctccagggta ttgagaagaa agtatcctta ccaaacgcag tttggttttt atctctgatt   34380
tacatgaatg atccttttttg tggctagagc aagctgttta gaattgaggg gtttctggga   34440
ttgtgacagt ttagctgcat gttggaatgt ctaagggcaa atattctaaa aagataacct   34500
gtcttgagtt caagaagaga atcgaagtct tgcagctgct aagcattaga atgttgtcaa   34560
agtaccactt tttggttgaa aaaaaaaaaat gcttcaggac ttccatctta actctgaggt   34620
tattctataa tttatcccta ggtgatttaa gaagaacccct tgttcttctt aaagtgttta   34680
cttctggtct ggcacaacaa atacctgaaa tgaaggccag taagtatttt ttaaaaaagg   34740
aaaacaataa agatggtttt gttaaaaaga ttcaggcagc agaaagaaaa gtgatgtgtc   34800
tctgaattat aattaagtaa aagcttatct tatgtttctc atttaagagg catcctgatg   34860
aatgacaatg cacagaagca tcgagaaatt caaacaacac aaatgcacaa ttgtgtatat   34920
ttacaagcta cagacctta aaataacaga catgttttct gattgattcc tactgaaaag   34980
cctaaatgtc tttgtgaaca aagctggccc tgtatatcaa gcatttccaa atatttggct   35040
caatttctat tatctctgaa aattaatggg gaggagccca cagagaaggc agagtgatag   35100
cctgatcttt ttcacagata tagtcaggaa gttgaatttc gataatacca ggaagaattg   35160
cttagtttga gcaaaagcat tttaggaaac gcgcagtggg taattagttt gggtgccgag   35220
atctggccat ctacatgcat ctgtccagtg agaaaaataa tgtttaggga ataatttat   35280 tcagatacat aatcatttga tcataactga gtatttaaat gggttgttat aaaaatatgtt   35340 tctacttttta tcacaatctt taaataaaca ttgaaattat atactctcaa agattccatc   35400
caattcaagc tttttaagtt tgttttttaa aaatattttt ccttctccaa gttaattact   35460
gcaaggaaag tagcagggta gagaaagaga aatggaagga taaaatgact tagctccatt   35520
```

-continued

```
cttcactcac catatgacac tttgcatatg gatggaagtt ttttaaaatg tctgtaattt    35580
cttttatccc caacaatgat aataaatcaa aagacatatt ctagacatcc acttttctta    35640
acatctgatt taaaagttga cacttttatt tttaaaaaaa aattgtggat ggacataaaa    35700
atttgaccag ctctaacaga gtttggtatt ctgtcttgtg tctaaaatat agatagatag    35760
aaaacaggtc aaaaggttag gaggaaaaca aatgggaaat agtaatttcg atttttagat    35820
tatcaatgat agattttaat atgtccttca aagagatcca gttcagaaac ccatgtgggc    35880
cagcattatc cctcttagtg gtagattgta ttggggtgac taagaattat gtatgtatta    35940
ataagtaata gataaatgac ataaaccaag tcttatcaaa taacaagaaa attagagaat    36000
ttccactaat gttcatatgt ttcagtcaga gaagtttata tttagaacag tgggcaagag    36060
gatatagatg attttcaata cattctacct caaaaaatga aaatgtaagt gacatatttt    36120
agacacatca caggtaaatt acctcagaag aaaggaagat gttaatgcca tctattcaga    36180
caagcacaaa atgacatgaa tggacataaa aattatatac agttgaattt agccttttta    36240
gtaaaaaagt aaaaacattt gatgttcaca catttacaat ttacagtgtt tatttgtaag    36300
aagtctcctt ccttgtagga tatattttca aatggacatt gtatatgctt gtagggtgct    36360
```